(12) United States Patent
Boyden et al.

(10) Patent No.: US 10,683,510 B2
(45) Date of Patent: Jun. 16, 2020

(54) ENGINEERING GENETIC CIRCUIT INTERACTIONS WITHIN AND BETWEEN SYNTHETIC MINIMAL CELLS AND USE THEREOF

(71) Applicant: Massachusetts Institute of Technology, Cambridge, MA (US)

(72) Inventors: Edward S. Boyden, Cambridge, MA (US); Katarzyna P. Adamala, Cambridge, MA (US); Daniel A. Martin-Alarcon, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/430,502

(22) Filed: Feb. 12, 2017

(65) Prior Publication Data

US 2017/0233748 A1 Aug. 17, 2017

Related U.S. Application Data

(60) Provisional application No. 62/294,586, filed on Feb. 12, 2016, provisional application No. 62/408,239, filed on Oct. 14, 2016.

(51) Int. Cl.
*C12N 15/63* (2006.01)
(52) U.S. Cl.
CPC .................................... *C12N 15/63* (2013.01)
(58) Field of Classification Search
None
See application file for complete search history.

(56) References Cited

PUBLICATIONS

Stano et al., "Semi-synthetic minimal cells as a tool for biochemical ICT" 109 BioSystems 24-34 (2012).*
Luisi et al., Approaches to semi-synthetic minimal cells: a review 93 Naturwissenschaften 1-13 (2006).*
Adamala et al., "Engineering genetic circuit interactions within and between synthetic minimal cells" 9 Nature Chemistry 431-439 (2017) ePub Nov. 14, 2016.*
Adamala, K. et al., "Competition between model protocells driven by an encapsulated catalyst." (2013) Nat. Chem. 5, 495-501.
Adamala, K. et al., "Construction of a liposome dialyzer for the preparation of high-value, small-volume liposome formulations." (2015) Nat. Protoc. 10, 927-938.
Brea, R. J. et al., "Towards Self-Assembled Hybrid Artificial Cells: Novel Bottom-Up Approaches to Functional Synthetic Membranes." (2015) Chem. A Eur. J. vol. 21, 1-8.
Brodel, A.K. & Kubick, S. "Developing cell-free protein synthesis systems: a focus on mammalian cells." (2014) Pharm. Bioprocess. 2, 339-348.
Caschera, F. & Noireaux, V. "Integration of biological parts toward the synthesis of a minimal cell." (2014) Curr. Opin. Chem. Biol. 22, 85-91.
Caschera, F. & Noireaux, V. "A cost-effective polyphosphate-based metabolism fuels an all *E. coli* cell-free expression system." (2015) Metab. Eng. 27 29-37.
Crabb, D. W. et al., "A Method for Increasing the Sensitivity of Chloramphenicol Acetyltransferase Assays in Extracts of Transfected Cultured Cell.s" (1987) Anal. Biochem. 163, 88-92.
De Souza, T. P., et al., "Spontaneous Encapsulation and Concentration of Biological Macromolecules in Liposomes: An Intriguing Phenomenon and Its Relevance in Origins of Life." (2014) J. Mol. Evol. 79, 179-192.
Hakkila, K., et al., "Reporter Genes lucFF, luxCDABE, gfp, and dsred Have Different Characteristics in Whole-Cell Bacterial Sensors." (2002) Anal. Biochem. 301, 235-242.
Hanczyc, M. M. et al., "Experimental Models of Primitive Cellular Compartments: Encapsulation, Growth, and Division." (2003) Science 302, 618-22.
Ingles-Prieto, A., et al., "Light-assisted small-molecule screening against protein kinases." (2015) Nat. Chem. Biol. 11, 952-954.
Jousma, H. et al., "Characterization of liposomes. The influence of extrusion of multilamellar vesicles through polycarbonate membranes on particle size, particle size distribution and number of bilayers." (1987) Int. J. Pharm. 35, 263-274.
Lewis, B. & Engelman, D.M. "Lipid Bilayer Thickness Varies Linearly with Acyl Chain Length in Fluid Phosphatidylcholine Vesicles." (1983) J. Mol. Biol 166, 211-217.
Meyenberg, K. et al., "SNARE derived peptide mimic inducing membrane fusion." (2011) Chem. Commun. 47, 9405-9407.
Mikami, S. et al., "An efficient mammalian cell-free translation system supplemented with translation factors." (2006) Protein Expr. & Purif. 46, 348-357.
Mikami, S. et al., "A human cell-derived in vitro coupled transcription/translatoin system optimized for production of recombinant proteins." Protein Expr. Purif. 62, 190-198 (2008).
Molla, A. et al., "Cell-Free, De Novo Synthesis of Poliovirus." (1991) Science 254 (5038), 1647.
Naylor, L.H., "Reporter Gene Technology: The Future Looks Bright." (1999) Biochem. Pharmacol. 58, 749-757.
Purnick, P. E. M., & Weiss, R. "The second wave of synthetic biology: from modules to systems." (2009) Nat. Rev. Mol., Cell Biol. 10, 410-422.
Ruiz-Mirazo, K. et al., "Prebiotic Systems Chemistry: New Perspectives for the Origins of Life." (2014) Chem. Rev. 114, 285-366.
Selgrade, D.F., et al., "Protein Scaffold-Activated Protein Trans-Splicing in Mammalian Cells." (2013) J. Am. Chem Soc. 135(20):7713-9.
Shin, J. et al., "An *E. coli* Cell-Free Expression Toolbox: Application to Synthetic Gene Circuits and Artificial Cells." (2012) ACS Synth. Biol. 1, 29-41.
Stano, P. & Luisi, P.L. "Semi-synthetic minimal cells: origin and recent developments." (2013) Curr Opin Biotechnol. 24:633-638.
Stefureac, R. et al., "Transport of a-Helical Peptides through a-Hemolysin and Aerolysin Pores." (2006) Biochemistry 45, 9172-9179.

(Continued)

*Primary Examiner* — Nancy J Leith
(74) *Attorney, Agent, or Firm* — Pierce Atwood LLP

(57) ABSTRACT

The invention, in some aspects relates to compositions comprising synthetic minimal cells (SMCs) and use of SMCs, pluralities of SMCs in relation to engineering genetic circuit interactions.

23 Claims, 33 Drawing Sheets
Specification includes a Sequence Listing.

(56) References Cited

PUBLICATIONS

Sun, Z.Z. et al., "Protocols for Implementing an *Escherichia coli* Based TX-TL Cell-Free Expression System for Synthetic Biology." (2013) J. Vis. Exp., 79, e50762, 1-15.
Szostak, J. W. et al., "Synthesizing Life." (2001) Nature, 409, 387-390.
Tan C. et al. "Molecular crowding shapes gene expression in synthetic cellular nanosystems." (2013) Nat. Nanotechnol. 8, 602-8.
Theobald, D. L., "A formal test of the theory of universal common ancestry." (2010) Nature, 465, 219-222.
Weber, L. A. et al., "A Cell Free System from HeLa Cells Active in Initiation of Protein Synthesis." (1975) Biochemistry, 14, 24, 5315-5321.

* cited by examiner

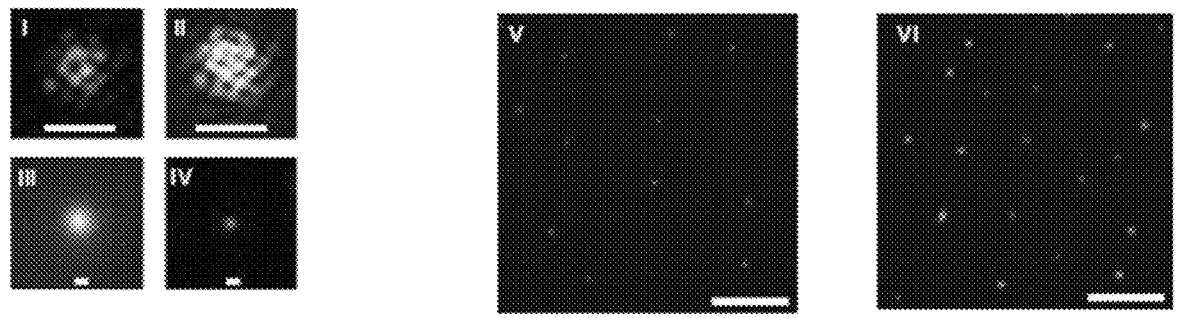
Fig. 2A
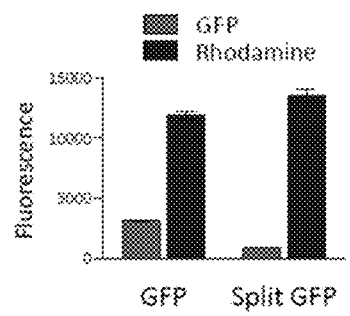
Fig. 2B
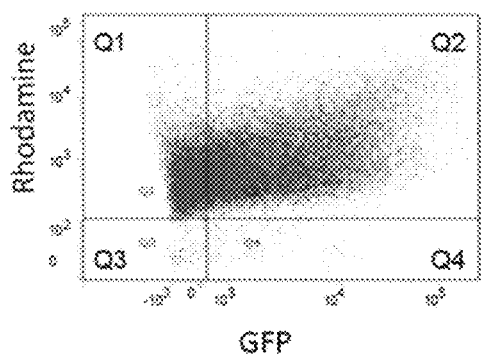 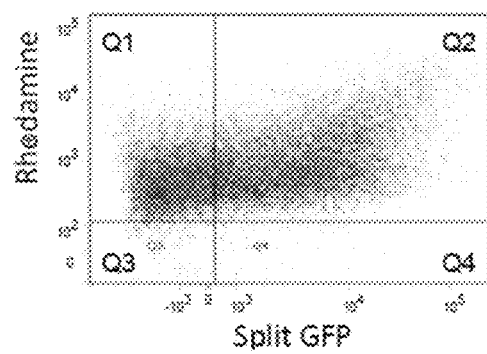
Fig. 2C                               Fig. 2D

     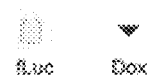
Fig. 3A
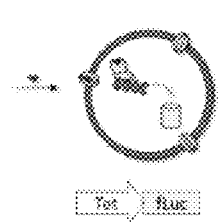 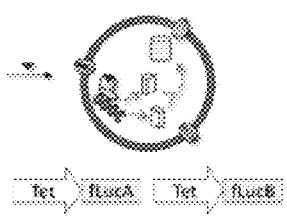 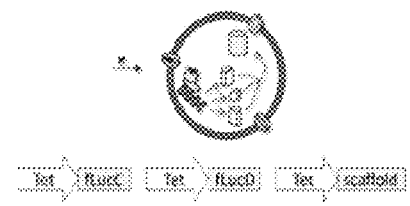
Fig. 3B  Fig. 3C  Fig. 3D
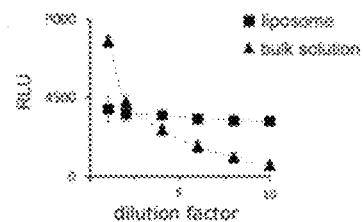  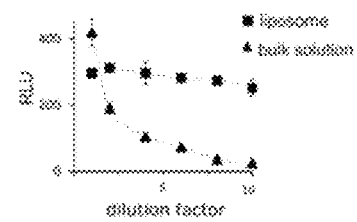
Fig. 3E  Fig. 3F  Fig. 3G
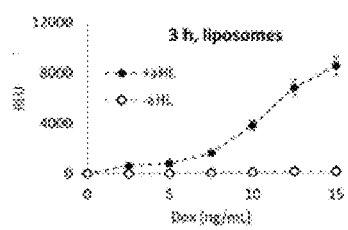 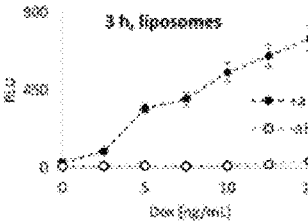 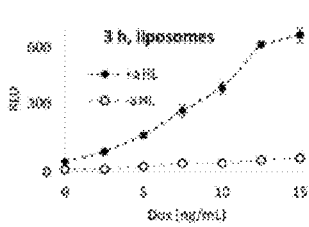
Fig. 3H  Fig. 3I  Fig. 3J
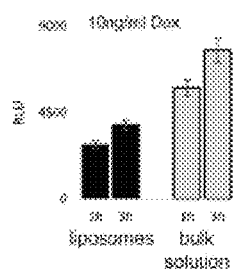 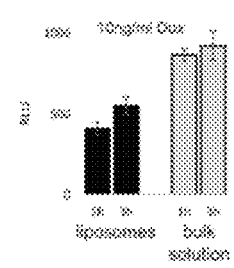 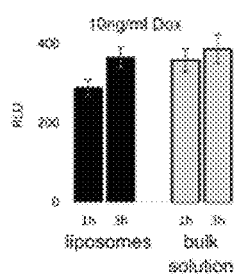
Fig. 3K  Fig. 3L  Fig. 3M

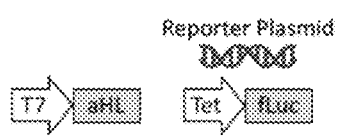 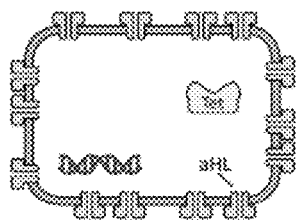 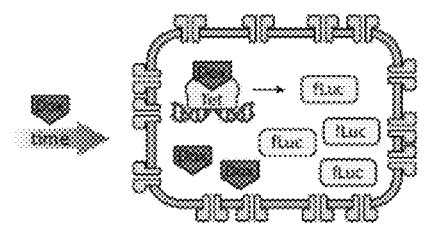
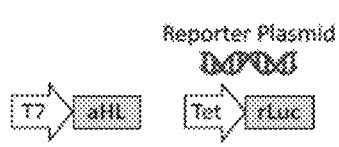 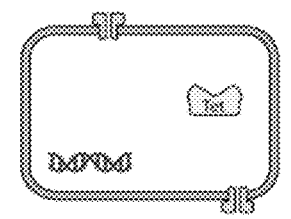 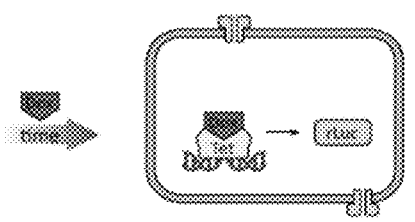
Fig. 4A
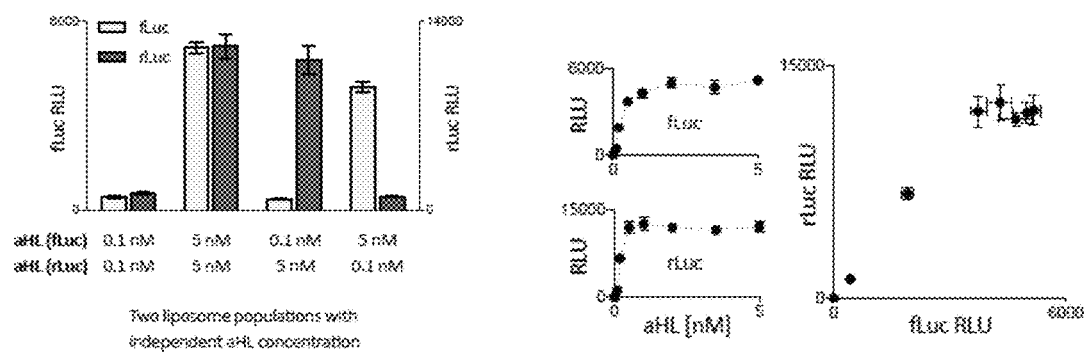
Fig. 4B            Fig. 4C
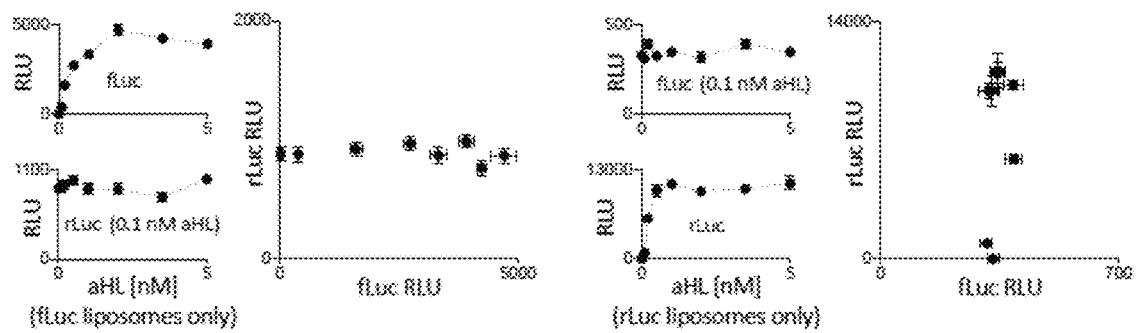
Fig. 4D            Fig. 4E

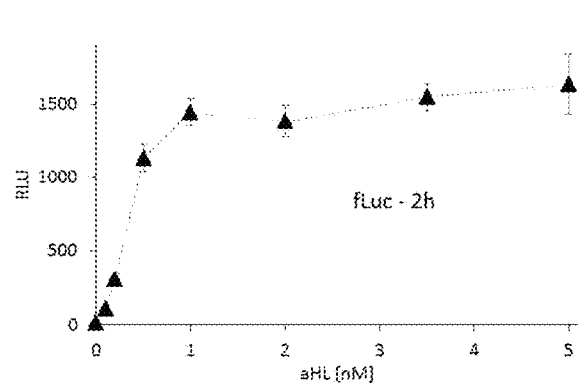 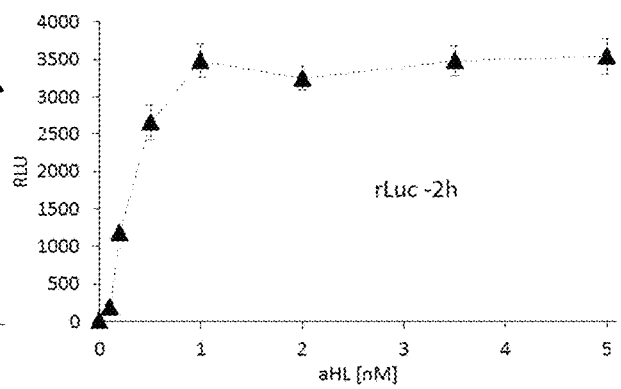
Fig. 16A　　　　　　　　　　　　　　Fig. 16B
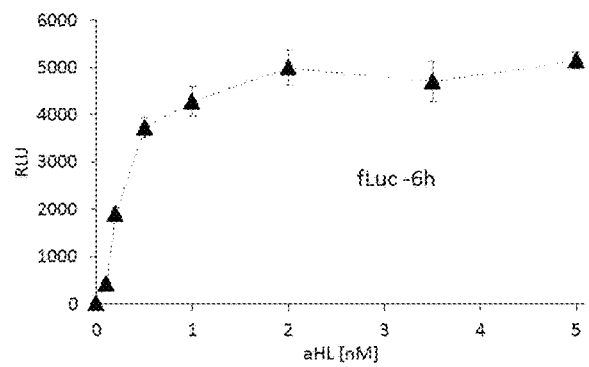 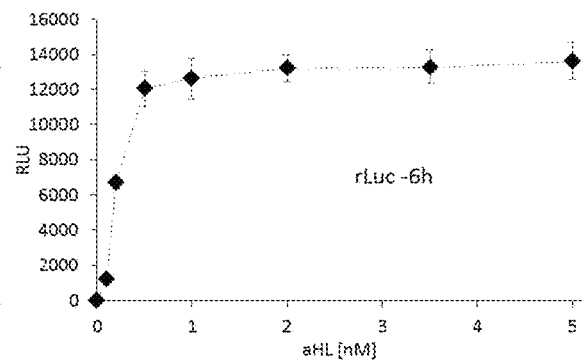
Fig. 17A　　　　　　　　　　　　　　Fig. 17B

| sample | 1 | 2 | 3 | 4 | 5 | 6 |
|---|---|---|---|---|---|---|
| probe | SNARE A | SNARE B | SNARE A | SNARE A | SNARE B | SNARE B |
| positive target | SNARE B | SNARE A | SNARE A | no SNARE | SNARE B | no SNARE |
| Sample | 7 | 8 | 9 | 10 | 11 | 12 |
| Probe | SNARE A | SNARE B | SNARE A | SNARE A | SNARE B | SNARE B |
| negative target | SNARE B | SNARE A | SNARE A | no SNARE | SNARE B | no SNARE |

SEQUENCE LISTING

```
<160> NUMBER OF SEQ ID NOS: 2

<210> SEQ ID NO 1
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 1
gcgagctagg aaacaccaaa gatgatattt gctcgc                              36

<210> SEQ ID NO 2
<211> LENGTH: 36
<212> TYPE: DNA
<213> ORGANISM: Artificial Sequence
<220> FEATURE:
<223> OTHER INFORMATION: Synthetic Oligonucleotide that has FAM at 5'
      end and DABCYL at 3' end

<400> SEQUENCE: 2
gcgagctagg aaacaccaaa gatgatattt gctcgc                              36
```

ENGINEERING GENETIC CIRCUIT INTERACTIONS WITHIN AND BETWEEN SYNTHETIC MINIMAL CELLS AND USE THEREOF

RELATED APPLICATIONS

This application claims benefit under 35 U.S.C. § 119(e) of U.S. Provisional application No. 62/294,586 filed Feb. 12, 2016 and U.S. Provisional application No. 62/408,239 filed Oct. 14, 2016, the entire disclosure and contents of each are incorporated by reference herein in their entirety.

GOVERNMENT INTEREST

This invention was made with government support under Grant Nos. U01 MH106011, R01 NS075421, and NS087724 awarded by the National Institutes of Health. The Government has certain rights in the invention.

FIELD OF THE INVENTION

The invention, in some aspects, relates to compositions and methods relating to engineering genetic circuit interactions.

BACKGROUND OF THE INVENTION

Chemical systems capable of performing biochemical reactions in the absence of live cells have been used in research and industry to study and model biological processes. Organisms from all three domains of life have been used to obtain transcription/translation (also referred to as "TX/TL") extracts for cell-free production of biochemical products from genetic codes. Encapsulating cell-free TX/TL extracts into liposomes have been used to make functional proteins using encapsulated systems reconstituted from recombinant cell-free translation factors, as well as cell-free extracts from bacterial and eukaryotic cells. Work on liposomal encapsulation methods has been focused on expressing single genes, with the goal of synthesizing a single gene product, and within a homogenous population of liposomes.

SUMMARY OF THE INVENTION

In one aspect of the invention, a synthetic minimal cell (SMC) that includes at least a portion of at least one multi-gene genetic circuit is provided. In some embodiments, the SMC includes at least one multi-gene genetic circuit. In some embodiments, the SMC includes a portion of the at least one multi-gene genetic circuit and a second SMC includes a second portion of the at least one multi-gene genetic circuit. In some embodiments, the multi-gene genetic circuit comprises 2, 3, 4, or more gene components. In certain embodiments, the portion of the multi-gene genetic circuit comprises 1, 2, 3, 4 or more gene components. In some embodiments, contacting the SMC with an externally delivered agent modulates an activity of at least one gene component of the genetic circuit. In some embodiments, an activity of a first gene component of the SMC modulates an activity of one or more additional gene components of at least one of: (1) the multi-gene genetic circuit of the SMC and (2) a multi-gene genetic circuit of another SMC. In certain embodiments, the multi-gene genetic circuit of (2) is different than the multi-gene genetic circuit of (1). In some embodiments, an activity of the multi-gene circuits comprises expression of 1, 2, 3, 4, or more polypeptides encoded by the gene components. In some embodiments, an expressed polypeptide is an optogenetic (light-activated) polypeptide. In some embodiments, the agent is a small molecule and optionally is soluble. In certain embodiments, the agent is selected from theophylline (Theo) and arabinose (Ara). In some embodiments, an activity of a first multi-gene genetic circuit modulates an activity of at least one additional multi-gene genetic circuit, and optionally activates a cascade of activity of 1, 2, 3, 4, or more additional gene components of the multi-gene genetic circuit in the SMC or in at least one additional SMC. In some embodiments, the SMC comprises one or more of bacterial transcription/translation (TX/TL) components and mammalian TX/TL components. In some embodiments, the SMC comprises one or more expression vectors comprising one or more of the gene components. In some embodiments, the expression vector comprises one or more of: a promoter sequence and a polynucleotide sequence encoding a polypeptide. In certain embodiments, the polynucleotide sequence encodes at least one of a membrane channel polypeptide and a detectable label polypeptide. In some embodiments the polynucleotide sequence encodes at least one of an ion pump polypeptide and a detectable label polypeptide. In certain embodiments, a membrane channel polypeptide is a light-activated polypeptide and an ion pump polypeptide is a light activated polypeptide. In some embodiments, the SMC comprises a fusion-inducing polypeptide in association with the SMC's exterior surface. In certain embodiments, the fusion-inducing polypeptide is a SNARE polypeptide or a SNARE polypeptide mimic. In some embodiments, the SMC is fused to at least a second SMC comprising at least one independently selected multi-gene genetic circuit. In some embodiments, the SMC and the second SMCs comprise the independently selected multi-gene genetic circuit. In certain embodiments, the SMC does not comprise the independently selected multi-gene genetic circuit of the second SMC.

According to another aspect of the invention, compositions that include a plurality SMCs independently selected from any embodiment of the aforementioned SMCs, are provided, wherein the multi-gene genetic circuits of the SCMs are independently selected. In some embodiments, the multi-gene genetic circuit of the SMCs comprises 1, 2, 3, 4, or more independently selected gene components. In certain embodiments, the SMCs in the plurality comprise the same multi-gene genetic circuit. In some embodiments, the SMCs in the plurality comprise independently selected multi-gene genetic circuits. In some embodiments, contacting an SMC of the plurality of SMCs with an externally delivered agent modulates an activity of at least one gene component of the genetic circuit of the contacted SMC. In some embodiments, at least one of the SMCs in the plurality of SMCs is fused to another of the SMCs in the plurality of SMCs. In certain embodiments, one or more multi-gene genetic circuits in two or more SMCs of the plurality are active in parallel. In some embodiments, an activity of one or more multi-gene genetic circuits in a first SMC of the plurality is modulated by at least one of: (1) an activity of a multi-gene genetic circuit in the first SMC of the plurality; and (2) an activity of a multi-gene genetic circuit in a second SMC of the plurality. In some embodiments, two or more of the plurality of SMCs operate in conjunction with each other as a network. In certain embodiments, operating in conjunction with each other comprises being in chemical communication with each other. In some embodiments, an activity of the multi-gene genetic circuit comprises expression of 1, 2, 3, 4, or more polypeptides. In some embodiments, an expressed polypeptide is an optogenetic (light-activated) polypeptide. In some embodiments, an activity of one or more of the multi-gene genetic circuits is modulated by an agent. In certain embodiments, the agent is at least one of: (1) a small molecule and (2) soluble. In some embodiments, the agent is selected from theophylline (Theo) and arabinose (Ara). In some embodiments, an activity of a first gene component of an SMC of the plurality modulates an activity of one or more additional gene components of at least one of: (1) the multi-gene genetic circuit of the SMC and (2) a multi-gene genetic circuit of another SMC of the plurality. In some embodiments, the multi-gene genetic circuit of (2) is different than the multi-gene genetic circuit of (1). In certain embodiments, an activity of a first multi-gene genetic circuit modulates an activity of at least one additional multi-gene genetic circuit, and optionally activates a cascade of activity of 1, 2, 3, 4, or more additional gene components of the first multi-gene genetic circuit in the SMC or in at least one additional SMC in the plurality. In some embodiments, one or more of the plurality of SMCs comprises one or more of: bacterial transcription/translation (TX/TL) components and mammalian TX/TL components. In some embodiments, one or more of the plurality of SMCs comprises one or more independently selected expression vectors. In certain embodiments, the expression vector comprises one or more of: a promoter sequence and a polypeptide-encoding polynucleotide sequence. In some embodiments, the polynucleotide sequence encodes at least one of: a membrane channel polypeptide and a detectable label polypeptide. In some embodiments, at least a portion SMCs in the plurality of SMCs comprise a fusion-inducing polypeptide in association with the SMCs' exterior surface. In certain embodiments, the fusion-inducing polypeptide is a SNARE polypeptide or a SNARE polypeptide mimic. In some embodiments, the SNARE polypeptide or SNARE polypeptide mimic associated with the exterior surface of the SMCs in a first portion of the plurality of SMCs that comprise a fusion-inducing polypeptide, is complementary to the SNARE polypeptide or SNARE polypeptide mimic associated with the exterior surface of the SMCs in a second portion of the plurality of SMCs. In some embodiments, an activity of a first multi-gene genetic circuit in one or more SMCs of the plurality of SMCs activates at least one additional multi-gene genetic circuit in one or more SMCs of the plurality of SMCs. In certain embodiments, an activity of a multi-gene genetic circuit in an SMC of the plurality of SMCs results in a cascade of multi-gene genetic circuit activation in one or more SMCs of the plurality of SMCs. In some embodiments, an activity of a first multi-gene genetic circuit in a first SMC of the plurality of SMCs activates 1, 2, 3, 4, or more additional multi-gene genetic circuits in one or more of: (1) the first SMC and (2) a second SMC. In some embodiments, the additional multi-gene genetic circuit is selected from: (1) a genetic circuit that is the same as the first multi-gene genetic circuit and (2) a multi-gene genetic circuit that is different than the first multi-gene genetic circuit. In some embodiments, contacting at least one SMC of the plurality of SMCs with an externally delivered agent modulates an activity of at least one of the multi-gene genetic circuits of the contacted SMC. In certain embodiments, an activity of a multi-gene genetic circuit of an SMC of the plurality of SMCs results in contacting one or more multi-gene genetic circuits of the SMC with an agent that modulates an activity of the one or more multi-gene genetic circuits.

According to yet another aspect of the invention, methods of producing a compound of interest are provided, the methods including (a) preparing a plurality of SMCs of any embodiment of an aforementioned plurality of SMCs, wherein the plurality of SMCs synthesize a compound of interest; (b) determining the presence of the synthesized compound of interest in the SMC; and (c) collecting the determined compound of interest from the SMC. In some embodiments, the method also includes altering the environment of the plurality of SMCs and determining an effect of the alteration on one or more SMCs of the plurality. In some embodiments, the compound of interest comprises a polypeptide.

According to yet another aspect of the invention, methods of modeling a biological process are provided, the methods including preparing a plurality of SMCs of any embodiment of an aforementioned plurality of SMCs, and assessing one or more characteristics of the plurality of SMCs. In certain embodiments, the method also includes altering the activity of one or more of the multi-gene genetic circuits and assessing the effect of the alteration on a characteristic of the plurality of SMCs. In some embodiments, a characteristic of the plurality of SMCs comprises one or more of: the interaction between one or more of the SMCs; an activity of one or more multi-gene genetic circuits; communication between two or more of the SMCs; and activity cascades in the SMCs.

According to yet another aspect of the invention, methods of identifying an effect of a candidate compound on activity of a multi-gene genetic circuit are provided, the methods including: (a) preparing one or more SMCs independently selected from any embodiment of the aforementioned SMCs; (b) contacting the prepared SMC(s) with a candidate compound; c) identifying a change in activity in one or more of the multi-gene genetic circuits in the SMC(s) contacted with the candidate compound; and (d) comparing the identified activity change to the activity in a control SMC not contacted with the candidate compound, wherein a change in the activity in the contacted SMC compared to the control SMC indicates an effect of the candidate compound on the test SMC.

According to yet another aspect of the invention, methods of assessing a modulating effect of an activity of a first SMC on an activity of a second SMC are provided. The methods include: (a) preparing two or more SMCs independently selected from any embodiment of the aforementioned SMCs, wherein the multi-gene genetic circuits in the two or more SMCs are independently selected; (b) activating a multi-gene genetic circuit in at least one of the SMCs; (c) determining the presence or absence of a modulation of an activity of a multi-gene genetic circuit in an SMC not activated in step (b); and (d) assessing the modulating effect of the activity of the SMC activated in step (b) on the activity of the multi-gene genetic circuit of the SMC not activated in step (b).

BRIEF DESCRIPTION OF THE DRAWINGS

FIG. 1A illustrates that synthetic minimal cells (synells) are semipermeable compartments made from a phospholipid bilayer membrane and various contents. The membrane can display a variety of proteins, including channel-forming proteins such as alpha-hemolysin (aHL). The phospholipid membranes of synells are permeable to molecules such as theophylline (Theo) and arabinose (Ara), and are permeable to others like β-D-1-thiogalactopyranoside (IPTG) and doxycycline (Dox) when aHL channels are present; these molecules can be used for triggering activity within synells. Synells can encapsulate cell lysates with transcriptional and/or translational activity, as well as DNA vectors encoding genes. Embodiments of various novel competencies of synells that, together, can be used to create complex, modular genetic circuits are demonstrated herein. FIG. 1B illustrates that synells can contain genetic circuits in which all the components and operations take place within the same liposome. FIG. 1C illustrates that two genetic circuits can work independently in separate liposome populations. FIG. 1D illustrates that genetic circuits within two different liposome populations can interact. FIG. 1E illustrates that genetic circuits can run in parallel in separate compartmentalized reactions; if those reactions are encapsulated by liposomes carrying fusogenic peptides such as SNAREs, the reaction products can be joined together in a hierarchical fashion.

FIG. 2A-D provides photomicroscopy images, a graph and blots illustrating molecular confinement of multicomponent genetic cascades. FIG. 2A provides images of liposomes expressing GFP. Sub-panels I-IV: structured illumination microscopy (SIM) images of representative liposomes expressing GFP and membrane-labeled with rhodamine. Every SIM image (panels labeled I, II, III, IV) represents a separate liposome; all liposomes were imaged on the same day and all liposomes came from the same sample, prepared 24 h before imaging. All SIM images in this figure are at the same scale; the large scale bars in panels I and II are 1 µm, the small scale bars in panels III and IV are 200 nm. Sub-panels V-VI: widefield epifluorescent images of liposomes expressing GFP. The liposomes for this imaging sample were extruded through a 2 µm filter and dialyzed with a 1 µm membrane; panel V shows sample after 6 h incubation and panel VI shows an aliquot of the same sample after 24 h incubation. The scale bars on panels V and VI are 10 µm. FIG. 2B-D are results illustrating fraction of synells expressing GFP and split GFP, measured by flow cytometry (for control flow cytometry experiments, see FIG. 27). FIG. 2B is a graph of bulk expression of GFP and fluorescence measured on the sample prior to the flow cytometry experiments. FIG. 2C shows analysis of samples expressing GFP; 68.4% of liposomes produced measurable green signal. FIG. 2D shows analysis of samples expressing split GFP; 61.8% of liposomes produced measurable green signal.

FIG. 3A-M shows results of molecular crowding of multicomponent genetic cascades. FIG. 3A provides a schematic image of synthetic minimal cells that were created. All liposomes of FIG. 3A-M initially contained mammalian transcription-translation (TX/TL) extract and constitutively expressed the alpha-hemolysin (aHL) and mammalian Tet protein. FIG. 3B-D show schematic images of genetic cascades involving one-, two-, or three-part luciferase protein assemblies. Expressed under doxycycline-inducible Tet promoters were whole firefly luciferase (fLuc) (FIG. 3B), the two halves (here denoted fLucA and fLucB) of split fLuc bearing split inteins and mutually binding coiled coils (FIG. 3C), and two halves (here denoted fLucC and fLucD) of split fLuc bearing split inteins and coiled coils that bind to a third common template (denoted "scaffold") (FIG. 3D). FIG. 3E-G are graphs that show effects of dilution on fLuc expression in liposomes vs. bulk solution, for the fLuc assemblies described in FIG. 3B-D (see FIG. 11 for experiments under the control of a constitutive P70 promoter). Dotted lines connect dots, and are not fits, throughout this figure. FIG. 3H-J are graphs that show end-point expression of luciferase measured at the 3 h time point, for 7 different concentrations of doxycycline (Dox). See FIG. 12 for corresponding 1 h end-point expression data, and FIGS. 13-15 for the same reactions in bulk solution. FIG. 3K-M provides graphs comparing liposomal vs. bulk solution expression of luciferase, at 2 different time points and for 10 ng/mL of Dox. The 2 plasmids in FIG. 3L and 3 plasmids in FIG. 3M were mixed at equimolar ratios, with total DNA concentration held constant. All data points are an average of 4 replicates; error bars indicate S. E. M.

FIG. 4A-E provides schematic diagrams and graphs illustrating insulation of genetic circuits operating in parallel liposome populations. FIG. 4A is a schematic of liposome populations designed to contain similar genetic components but to respond differently to the same environmental concentration of the non-membrane-permeable small molecule activator doxycycline (Dox), by expressing different amounts of the alpha-hemolysin channel protein (aHL). These liposomes contain a measured amount of the plasmid for constitutively expressed aHL, and of a plasmid driving either firefly luciferase (fLuc) or Renilla luciferase (rLuc) from the Tet inducible promoter (the luciferase plasmids were always held at the same concentration). Throughout this figure, the two populations were incubated together in the solution containing Dox and harvested after 6 h (see FIGS. 16 and 17 for rLuc and fLuc expression as a function of aHL plasmid concentration, after 2 h and 6 h, respectively). FIG. 4B is a graphs showing that each liposome contains either 0.1 nM or 5 nM of the aHL plasmid. FIG. 4C provides graphs showing Luciferase expression in symmetrical populations, where the amount of aHL DNA is the same across the two populations; the amount of fLuc and rLuc expression is graphed with respect to aHL plasmid concentration and to each other. FIG. 4D-E provide graphs showing Luciferase expression in asymmetrical populations. FIG. 4D shows Luciferase expression when Renilla liposomes have a constant aHL plasmid concentration (0.1 nM) but the concentration of that plasmid is varied in the firefly liposomes. Expression of rLuc and fLuc are graphed against the plasmid concentration in firefly liposomes and against each other. FIG. 4E shows Luciferase expression as in d, but with constant aHL plasmid concentration in firefly liposomes and variable concentration in Renilla liposomes. Error bars indicate S. E. M. n=4 replicates.

FIG. 5A shows a scheme for mixing two populations of liposomes at different ratios of their components while maintaining a constant lipid concentration of 10 mM (the same scheme was used throughout this figure and FIG. 6). Each population contains the same amount of liposomes, but the liposome occupancy can vary between 0 (all liposomes are empty) and 1 (the maximum fraction of the liposomes contain reagents). FIG. 5B-D illustrates results of externally activated two-part circuits, with bacterial TX/TL. FIG. 5B provides a scheme of interacting populations, denoted sensor and reporter. Sensor liposomes contain the alpha-hemolysin gene and are filled with IPTG; reporter liposomes contain machinery for firefly luciferase expression. During activation, arabinose (Ara) diffuses through the sensor liposome membrane and induces aHL expression, which releases IPTG, which induces fLuc expression in the reporter. FIG. 5C provides a scheme of expression of fLuc for varying ratios of occupancy (as in FIG. 5A), for the sensor and reporter liposomes with indicated contents. This panel represents the time point 6 h (for complete time series see FIG. 30). For this circuit without arabinose see FIG. 19. FIG. 5D is a graph showing expression of fLuc for a circuit in which the reporter liposomes contain DNA for a multicomponent genetic cascade, as indicated. This panel represents the 6 h time point (for complete time series, see FIG. 31. For this circuit without arabinose, see FIG. 21). FIG. 5E-F provides graphs showing externally activated two-part circuits, containing both bacterial and mammalian TX/TL components. In FIG. 5E sensor vesicles contain the Theo-triggered aHL gene and Dox; reporter liposomes contain constitutively expressed aHL and Tet, and Dox/Tet-driven fLuc. During activation, Theo diffuses through the membrane of the activator liposomes and induces aHL expression, which creates pores that release Dox from the activator. Dox induces fLuc expression in the reporter liposomes. FIG. 5F shows results of expression of fLuc, for varying ratios of sensor and reporter liposomes (this panel represents 6 h time point; for complete time series see FIG. 32. For this circuit without Theo, see FIG. 23). Error bars indicate S. E. M. n=4 replicates.

FIG. 6A shows a general scheme for SNARE-mediated liposome fusion. Two populations of liposomes, population A and population B, were created and decorated with complementary SNARE protein mimics in their outer leaflet. The photomicrographic images to the right, in sub-panels I through IX, are maximum-intensity projections of structured illumination microscopy (SIM) z-stacks of liposomes membrane-labeled with rhodamine, bearing complementary SNARE pairs, and fused for 4 hours. All images from panels I through IX represent separate fields of view. Scale bars, 5 All liposomes in this figure, except FIG. 6F, contained bacterial TX/TL components. FIG. 6B-F provides results from five different instantiations of the liposome fusion concept, exploring several ways to distribute genetic circuits across fusable liposomes, with two different populations of liposomes at three occupancy levels for each case. FIG. 6B shows results from mixing of constitutively expressed T7 RNA polymerase with firefly Luciferase under T7 promoter. FIG. 6C shows results from mixing of a non-membrane-permeable small molecule activator IPTG with its inducible promoter, driving fLuc production. FIG. 6D shows results from mixing of a constitutively expressed membrane channel with an inducible promoter driving fLuc production, in the background of the small molecule that induces the promoter (IPTG). FIG. 6E shows results from mixing liposomes with genes encoding split protein. FIG. 6F shows results from mixing liposomes containing mammalian transcription (HeLa) and translation (HeLa) system, producing fLuc. For all five systems in FIG. 6B-F, experiments on the large graph are with one of a matching pair of SNARE on each population, the top of the two small panels is both liposomes with the same SNARE, and the bottom one neither population had any SNAREs. In both small graphs of FIG. 6B-F, the y-axis is in logarithmic scale to show the near-zero values for non-fusing liposomes. Switching which liposome contained which SNARE had no effect on the results (FIG. 24), whereas the absence of SNARE proteins or the presence of identical SNAREs on both populations hindered fusions (small graphs on FIG. 6B-F). Error bars indicate S. E. M. n=4 replicates.

FIG. 7A is a schematic diagram of synthetic minimal cells that were created. The liposomes used in studies illustrated in FIG. 7A-E were built with bacterial transcription/translation (TX/TL) components; and contained the gene for T7 RNA Polymerase (T7RNAP) under an inducible element—either the Theo aptamer, which responds to theophylline (Theo), or the PBAD promoter, which responds to arabinose (Ara)—and also contained the gene for firefly luciferase (fLuc) under a T7 promoter. A small molecule activator (Theo or Ara) drives T7RNAP expression, which in turn drives fLuc expression. FIGS. 7B & C are graphs showing the theophylline-triggered genetic cascade. FIG. 7B demonstrates fLuc expression over time, with and without 2 mM Theo; each of the two plasmids is present at 5 nM. FIG. 7C illustrates final fLuc expression at different concentrations of each plasmid, all measured after 10 h of expression. FIGS. 7D & E are graphs showing the arabinose-triggered genetic cascade. FIG. 7D shows fLuc expression over time, with and without 10 mM Ara; each of the two plasmids is present at 5 nM. FIG. 7E illustrates final fLuc expression at different concentration of each plasmid, all measured after 10 h of expression. All data points are an average of 4 replicates; error bars indicate S. E. M.

FIG. 8A provides a schematic diagram of synthetic minimal cells created. Two liposome populations were designed to contain similar genetic components but to respond differently to the same environmental concentration of the non-membrane-permeable small molecule activator doxycycline (Dox), by expressing different amounts of the alpha-hemolysin channel protein (aHL). The liposomes used in FIG. 8A-E all contained mammalian transcription/translation (TX/TL) extract, a measured amount of the plasmid for constitutively expressed aHL, and a plasmid driving either firefly luciferase (fLuc) or Renilla luciferase (rLuc) from the mammalian Tet inducible promoter (the luciferase plasmids were always present at the same concentration). Throughout this figure, the two liposome populations were always incubated together in the same solution containing Dox and harvested after a set time (see FIGS. 16 and 17 for rLuc and fLuc expression data at different aHL plasmid concentrations, for two different time points). FIG. 8B is a graph showing expression of rLuc and fLuc for the two populations of SMCs. Each liposome contains either 0.1 nM or 5 nM of the aHL plasmid. FIG. 8C are graphs showing luciferase expression in symmetrical populations, where the amount of aHL DNA is the same across the two populations. FIG. 8C shows the amount of fLuc and rLuc expression, graphed with respect to aHL plasmid concentration and to each other. FIGS. 8D & E are graphs illustrating luciferase expression in asymmetrical populations. FIG. 8D shows results from luciferase expression when firefly liposomes have a constant aHL plasmid concentration of 0.1 nM but the concentration of that plasmid is varied in the Renilla liposomes. Expression of rLuc and fLuc are graphed against the plasmid concentration in firefly liposomes and against each other. FIG. 8E shows results from luciferase expression as in FIG. 8D, but for cases of constant aHL plasmid concentration in Renilla liposomes and variable concentration in Firefly liposomes. All data points are an average of 4 replicates; error bars indicate S. E. M.

FIG. 9A is a schematic diagram showing a general scheme for mixing two distinct populations of liposomes at different ratios of their components while maintaining a constant lipid concentration of 10 mM (the same scheme was used throughout this figure and FIG. 10). Each population always contained the same amount of liposome, but the liposome occupancy could vary between 0 (all liposomes are empty) and 1 (all liposomes contain synthetic biology reagents). FIG. 9B-D shows schematic diagrams and graphs illustrating externally activated two-part circuits, constructed with bacterial transcription/translation (TX/TL) components. FIG. 9B shows a general scheme containing two interacting liposomes, denoted sensor and reporter liposomes. Sensor liposomes contain the alpha-hemolysin gene and are filled with IPTG; reporter liposomes contain the machinery for firefly luciferase (fLuc) expression. During activation, arabinose (Ara) diffuses through the membrane of the sensor liposomes and induces aHL expression, which creates pores that release IPTG from the sensor liposomes. IPTG, in turn, induces fLuc expression in the reporter liposomes. FIG. 9C shows graphs of expression of fLuc for varying ratios of occupancy (as in FIG. 9A), for the sensor and reporter liposomes with contents as indicated. The bars in FIG. 9C represent the final time point of 6 hours; for the complete time series, see FIG. 18. For the end-point expression of the same circuit without arabinose triggering, see FIG. 19. FIG. 9D shows graphs of expression of fLuc for a similar circuit in which the reporter vesicles contain DNA for a multicomponent genetic cascade, as indicated. Bars in FIG. 4D represent the final time point of 6 hours; for the complete time series, see FIG. 20. For the end-point expression of the same circuit without arabinose triggering, see FIG. 21). FIGS. 9E & F show results of externally activated two-part circuits, constructed with both bacterial and mammalian TX/TL components. FIG. 9E is a schematic diagram showing mixture of two populations of liposomes used in experiments of FIG. 9F: sensor (bacterial) and reporter (mammalian). Sensor vesicles contain the Theo-triggered aHL gene and contain Dox; reporter liposomes contain constitutively expressed aHL and Tet, and Dox/Tet-driven fLuc. During activation, Theo diffuses through the membrane of the activator liposomes and induces aHL expression, which creates pores that release Dox from the activator liposomes. Dox, in turn, induces fLuc expression in the reporter liposomes. FIG. 9F is a graph showing expression of fLuc for varying ratios of sensor and reporter liposomes (bars in FIG. 9F represent the final time point of 6 hours; for the complete time series, see FIG. 22. For the end-point expression of the same circuit without Theo, see FIG. 23). All data points are an average of 4 replicates; error bars indicate S. E. M.

FIG. 10A provides a schematic of a general scheme for SNARE-mediated liposome fusion. Two populations of liposomes, A and B, were created and decorated with complementary SNARE protein mimics in their outer leaflet. Fusion of the liposomes is mediated by complementary SNARE protein mimics. All liposomes used in FIG. 10 studies contained bacterial transcription/translation (TX/TL) components. FIG. 10B-E shows schematic diagrams and graphs of results from studies in which four different instantiations of this scheme were tested. Several ways to distribute genetic circuits across fusable liposomes were examined. For each case two different populations of liposomes were combined at three occupancy levels, resulting in nine combinations (for description of the liposome occupancy concept, see FIG. 9A). FIG. 10B shows results of studies of mixing of constitutively expressed T7 RNA polymerase (T7RNAP) with a target payload, namely firefly Luciferase (fLuc) driven by its promoter. FIG. 10C shows results of studies that included mixing of a membrane-impermeable small molecule activator with its inducible promoter, driving fLuc. FIG. 10D shows results of studies that included mixing of a constitutively expressed membrane channel with an inducible promoter driving fLuc, in the background of the small molecule that induces the promoter (IPTG). FIG. 10E shows results of studies that included mixing of two halves of a split protein, fLucA and fLucB (as defined in FIG. 3). For all 4 systems in FIGS. 10B-E, the large graph shows experiments where each population of liposomes bears one of a matching pair of SNARE proteins. The top one of the two small panels shows experiments where both liposomes contained the same SNARE protein (which should not bind), and the bottom one of the two small panels shows experiments where neither population of liposomes had any SNARE proteins. In both small graphs of each FIG. 10B-E, the Y-axis is in logarithmic scale to show the near-zero values for non-fusing liposomes. For all four systems in this figure, switching which liposome contained which SNARE had no effect on the results (FIG. 24), whereas the absence of SNARE proteins or the presence of identical SNARES on both liposome populations completely hindered fusions (small graphs in FIG. 10B-E). All data points on the large graphs are an average of 4 replicates; error bars indicate S. E. M.

FIG. 11A-C provides graphs showing effects of dilution on flue expression in liposomes and un-encapsulated reactions. Expression of one-, two-, and three-peptide systems is under control of P70 promoter, without small molecule activation. FIG. 11A is a graph of results from a one-part luciferase system (as in FIG. 3B). FIG. 11B is a graph of results from a two-part split luciferase system (as in FIG. 3C). FIG. 11C is a graph of results from a three-part scaffolded split luciferase system (as in FIG. 3D).

FIG. 12A is a graph of results from a one-part luciferase system (as in FIG. 3B). FIG. 12B is a graph of results from a two-part split luciferase system (as in FIG. 3C). FIG. 12C is a graph of results from a three-part scaffolded split luciferase system (as in FIG. 3D).

FIG. 13A shows expression result at one hour and FIG. 13B shows results at 3 hours. The Y-axis is relative light units (RLU) and the X-axis is concentration of Dox in the solution.

FIG. 14A shows expression result at one hour and FIG. 14B shows results at 3 hours. The Y-axis is relative light units (RLU) and the X-axis is the concentration of Dox in the solution.

FIG. 15A shows expression result at one hour and FIG. 15B shows results at 3 hours. The Y-axis is relative light units (RLU) and the X-axis is the concentration of Dox in the solution.

FIG. 16A-B provides graphs showing results of expression of fLuc (FIG. 16A) and rLuc (FIG. 16B) at 2 h end-point, from liposomes with different concentration of aHL plasmid. The Y-axis is relative light units (RLU) and the X-axis is the concentration of aHL in the solution.

FIG. 17A-B provides graphs showing results of expression of fLuc (FIG. 17A) and rLuc (FIG. 17B) at 6 h end-point, from liposomes with different concentration of aHL plasmid. The Y-axis is relative light units (RLU) and the X-axis is the concentration of aHL in the solution.

FIG. 24A shows results of creating a cascading genetic circuit: T7RNAP under the P70 promoter (SNARE_B) mixed with fLuc under T7 promoter (SNARE_A). FIG. 24B shows results of delivering a small molecule activator: fLuc under lac promoter (SNARE_B) mixed with IPTG-filled liposomes (SNARE_A). FIG. 24C shows results of creating a protein reconstitution system: fLucA (SNARE_B) mixed with fLucB (SNARE_A). FIG. 24D shows results of enabling small molecule activation: liposomes expressing aHL (SNARE_B) mixed with fLuc under lac promoter (SNARE_A), IPTG added to the external solution.

FIG. 25A shows results for firefly luciferin-firefly luciferase substrate; FIG. 25B shows coelenterazine—renilla luciferase substrate; FIG. 25C shows results for furimazine—NANOLUC® luciferase substrate; FIG. 25D shows results for X-gal-beta-galactosidase substrate; FIG. 25E shows results for chloroamphenicol acetyltransferase substrate; and FIG. 25F shows results for CCF2-beta-lactamase substrate.

FIG. 27A shows results from a control red fluorescence sample: liposomes membrane-labeled with LISSAMINE™ Rhodamine B, without the GFP plasmid. The y-axis is fluorescence in the red (rhodamine) channel and the x-axis is fluorescence in the green (GFP) channel. FIG. 27B shows results from a control green fluorescence sample: liposomes with T7-GFP plasmid; axes are as in FIG. 27A. Reaction conditions and plasmid concentrations are the same as in FIG. 2. The cytometry analysis was performed on FACSCANTO™ II Flow Cytometry System, and the data analysis was performed using FACSDIVA™ 8.0 Software. The dots on the cytometry data on this figure and in FIG. 2 represent counted events; the black dots represent events below the scattering threshold P1 (the threshold was set by the operator to eliminate events smaller than the typical size of dust in the sample); the same threshold applied to all datasets. FIG. 27C shows an example of the scattering threshold size range; the y-axis is side scatter SSC-H and the x-axis is forward scatter FSC-H.

FIG. 38A provides confocal microscopy images of liposome expressing alpha hemolysin-mClover protein fusion, with liposome membrane labeled with red dye (rhodamine functionalized with a lipid tail, LISSAMINE™ rhodamine B). Giant unilamellar vesicles were prepared according to previously described methods (see Kamat, N. P. et al. (2015) Angew. Chemie—Int. Ed. 54, 11735-11739), and non-encapsulated TL/TL mixture was removed by dialysis as described in Examples, Materials and Methods. The scale bar is 5 µm. FIG. 38B shows incorporation of alpha hemolysin protein in the bilayer membrane of the phospholipid liposome is measured by FRET (Fluorescence Resonance Energy Transfer). The membrane is labeled with two FRET pair dyes: LISSAMINE™ Rhodamine B 1,2-Dihexadecanoyl-sn-Glycero-3-Phosphoethanolamine, Triethylammonium Salt and NBD-PE N-(7 Nitrobenz-2-Oxa-1,3-Diazol-4-yl)-1,2-Dihexadecanoyl-sn-Glycero-3-Phosphoethanolamine, Triethylammonium Salt. The alpha hemolysin was constituently expressed inside liposomes using a bacterial TX/TL system and the bacterial P70 promoter (squares); as a control a soluble, non-membrane associated protein (firefly luciferase) was expressed under the same conditions (circles).

DETAILED DESCRIPTION

Figure 1A:
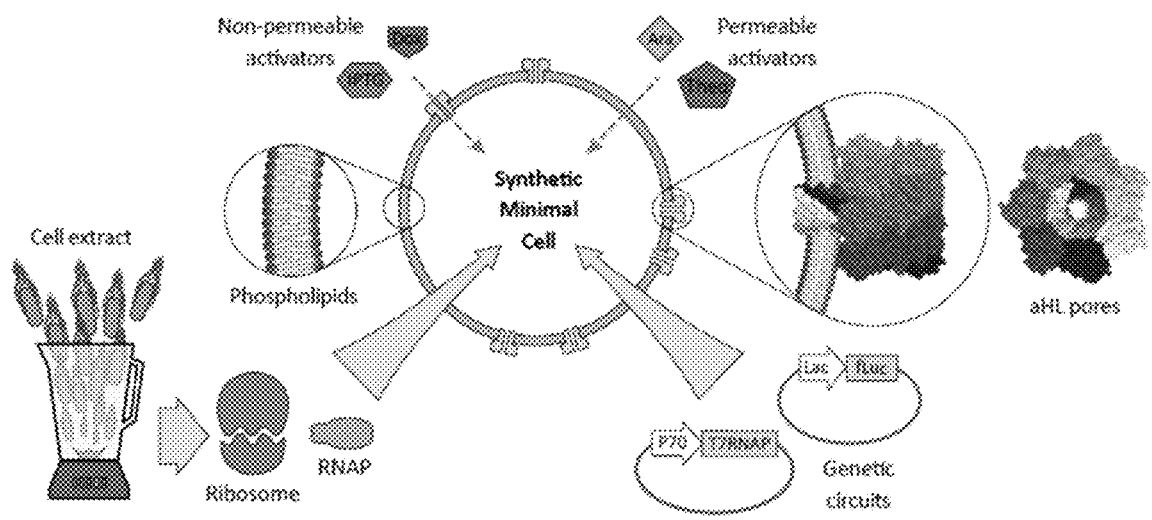
FIG. 1A-E provides schematic diagrams showing an overview of embodiments of genetic circuit interactions within and between synthetic minimal cells (synells).

Liposome encapsulation of synthetic minimal cells (SMCs) enables chemical reactions to proceed in well-isolated, molecularly crowded environments. The invention, in some aspects, includes liposomal SMCs as well as their use, wherein the liposome SMCs include compartmentalized genetic circuits or cascades. As used herein the term "genetic circuit" refers to a set of chemicals, one part of which triggers the initiation, modulation or otherwise alters generation of a gene product, which then can directly or indirectly initiate, modulate, or otherwise alter the generation of another gene product encoded for by another part of the genetic circuit. The use of genetic circuits permits scaling of production (a non-limiting example of which is gene expression for polypeptide production) and permits low, moderate, and/or high levels of complexity in the production process, which may be determined by the engineering of the SMCs and genetic circuits of the invention. Certain SMCs of the invention are prepared such that they contain genetic cascades that can be triggered, modulated, reduced, or induced by one or more of an internal stimulus and an external chemical stimulus. Some aspects of the invention include preparation and/or use of populations of SMCs that are able to operate genetic cascades in parallel to one another and/or to jointly regulate their cascades via exchanged small molecule messengers. The terms: "liposome", "synell", and "synthetic minimal cell" (SMC) are used interchangeably herein in reference to liposome bioreactors performing some of the biochemical functions of the living cell, most notably transcription and translation for the expression of proteins.

Methods and compositions of the invention, in some aspects, permit modularity of multi-component genetic circuits and cascades in synthetic biology. By encapsulating genetic circuits and cascades within synells and orchestrating the synells to either operate in parallel, communicate with one another, or fuse with one another in a controlled way, methods of the invention can be used to create and utilize genetic cascades that take advantage of the modularity enabled by liposomal compartmentalization. Thus, in some aspects of the invention, methods are provided that enable genetic cascades to proceed in well-isolated environments while permitting the desired degree of control and communication. Synells of the invention may be used singly, in combination with other synells, in networks of other synells, or in other conformations with other synells that also support complex chemical reactions that benefit from both the high-fidelity isolation of multiple reactions from one another, as well as controlled communication and regulatory signal exchange between those reactions.

Compositions have now been prepared that permit maximization of the modularity of their design to enable the integration of different reaction networks and to optimize their scalability and flexibility. One aspect of the invention includes methods of encapsulation of genetic circuits and reaction cascades within liposomes thereby permitting chemical reactions to proceed in well-isolated environments. It has now been demonstrate that it is possible to engineer genetic circuit-containing synells to contain multiple-part genetic cascades, and that these cascades can be controlled by external signals as well as inter-liposomal communication without cross-talk. Methods of the invention have now been demonstrated that result in liposomes containing different cascades to be fused in a controlled way so that the products of incompatible reactions can be brought together. In some aspect of the invention, compositions are provided that include one or more synells. Methods of the invention, in some embodiments include use of such synells to enable more modular creation of synthetic biology cascades, an essential step towards their programmability.

Certain aspects of the invention include a synthetic minimal cell (SMC) that includes at least a portion of at least one multi-gene genetic circuit. A portion of a multi-gene genetic circuit may be part of a multi-gene genetic circuit that is present in one SMC and part of the multi-gene genetic circuit that is present in another SMC. In certain aspects of the invention, less than a full multi-gene genetic circuit may be present in an SMC of the invention and the remainder of the full multi-gene circuit may be present in one additional SMC. In another non-limiting example, in certain aspects of the invention, less than a full multi-gene genetic circuit (also referred to herein as "a portion") may be present in an SMC of the invention and another part of the multi-gene genetic circuit may be present in one additional SMC, and a further part of the multi-gene genetic circuit may be present in another additional SMC, etc. Thus, a multi-gene genetic circuit of the invention may include genes that are expressed in different SMCs of the invention, for example, an SMC of the invention may include one or more genes of a multi-gene genetic circuit and a second SMC of the invention may include one or more independently selected genes of the same multi-gene genetic circuit and one of the SMCs may express a polypeptide that directly or indirectly induces expression of a polypeptide in another SMC. Thus, two or more SMCs may be part of the same multi-gene genetic circuit. In certain aspects of the invention, an SMC may include all of the genes that make up a multi-gene genetic circuit. A multi-gene genetic circuit may include 2, 3, 4, or more genes, which are also referred to herein as "gene components" of the multi-gene genetic circuit.

Some aspects of the invention include methods of preparing SMCs of the invention, and methods of their use. As used herein the term "multi-gene genetic circuit" means two or more genes that interact either directly or indirectly with each other. For example, a polypeptide expressed by a gene in a vector in an SMC of the invention may trigger, modulate, reduce, or induce expression of one or more of a second, third, fourth, fifth or more genes in the SMC and/or in another SMC. The presence of a circuit indicates that expression activity of one gene modulates expression of another gene in one or more of the same or another SMC of the invention.

Expression of a gene of a multi-gene genetic circuit is also referred to as an "activity" of the gene. Contacting an SMC of the invention with an agent may modulate (increase or decrease) an activity of a gene that is part of a multi-gene genetic circuit. In certain instances, an agent that modulates activity of a gene is an exogenous agent that is contacted with the SMC. An exogenous agent may be added to the external environment of an SMC from a source external to the SMC's environment, or may be produced or released by another SMC that is present in the SMC's environment. In some instances, an agent that modulates activity of a gene is an endogenous agent that is expressed within an SMC and the expressed agent modulates an activity of another gene in that SMC. In certain aspects of the invention, a gene that is part of multi-gene genetic circuit may express a polypeptide in an SMC and the polypeptide alters the internal environment of the SMC, thus modulating expression of another gene component of the multi-gene genetic circuit in the SMC. For example, though not intended to be limiting, a gene in an SMC may encode a channel protein that is expressed in the SMC and permits entry of an agent such as a small molecule, etc. that modulates (for example, increases or decreases) expression of another gene in the multi-gene genetic circuit of the SMC. As used herein the term "externally delivered" used in relation to an agent, means an agent that is an exogenous agent. In some aspects of the invention, the agent is a small molecule and in certain embodiments, the agent is soluble. Non-limiting examples of modulating agents, which in some embodiments of the invention are referred to as "activators", are arabinose (Ara) and theophylline (Theo).

As used herein, the terms "increases" or "increase" in reference to expression of a polypeptide means raising a level of expression from zero to any amount above zero or raising the level of expression from an existing level to a higher level of expression. As used herein, the terms "decreasing" or "decrease" in reference to expression of a polypeptide means lowering a level of expression from an amount to an amount that is lower, which may be, but need not be a level of zero expression.

Certain aspects of the invention include SMCs having one or more functional characteristics, non-limiting examples of which include: expression of one or more polypeptides; triggering expression of one or more polypeptides internal to the SMC; triggering expression of one or more polypeptides external to the SMC, for example in one or more additional SMCs; modulation of an activity of a polypeptide internal to the SMC to reduce expression of its encoded polypeptide; modulation of an activity of a polypeptide present in another SMC to reduce expression of its encoded polypeptide; communication with one or more additional SMCs or with other elements external to the SMC; etc. In some aspects of the invention, modulating an activity comprises increasing the activity and in certain embodiments of the invention modulating an activity comprises the decreasing activity. Additional examples of functional characteristics that may be present in SMCs of the invention are described herein.

Certain aspects of the invention include SMCs that have one or more structural characteristics, non-limiting examples of which include: liposomal encapsulation; inclusion of one, two, three, four, or more expression vectors; an internal environment suitable for transcription and translation of one or more genes; one, two, three, four, or more genes that can be triggered or induced to express their encoded polypeptide or modulated to reduce expression of their encoded polypeptide; one or more expression vectors that encode fusion proteins; encoded detectable labels; decoration of the external liposomal surface with one or more of a detectable label, a fusion molecule, a delivery molecule, etc. Additional examples of structural characteristics that may be present in SMCs of the invention are described herein. Some aspects of the invention also include methods of preparing SMCs of the invention, and methods of their use.

SMCs and methods of their use as encompassed by the invention allow SMCs containing genetic circuits to be regulated externally, to communicate with each other, and to work together in networks. A non-limiting example of a benefit of an SMC of the invention is in its use to provide modularity in synthetic biology procedures and methods. An additional non-limiting example of methods of use of SMCs of the invention is in basic-science studies of the origins of life. Additional methods for which SMCs of the invention may be used will be recognized by those skilled in the art. Certain aspects of the invention comprise encapsulating cell-free transcription/translation (also referred to as "TXITL") extracts into liposomes to create bioreactors, which are referred to herein as SMCs. Means to prepare single gene artificial and synthetic cells and liposomes, and the use of cell-free TX/TL extracts in artificial cells and liposomes are known in the art, see for example: Zemella, A. et al., (2015) ChemBiochem Vol. 16, Issue 17:2420-2431; Forster, A. C. & Church, G. M, (2006) Mol. Syst. Boil 2,45; Brea, R. J. et al., (2015) Chem. A Eur. J. Vol. 21, Issue 36:12564-12570; Luisi, P. L. et al., (2006) Naturwissenchaften 93, 1-13; Stano, P. & Luisi, P. L. Curr Opin Biotechnol. (2013) 24:633-638; Tan, C. et al. (2013) Nat. Nanotechnol. 8, 602-8; de Souza, T. P. et al. (2012) Orig. Life Evol. Biosph. 42, 421-428; de souza, T. P., et al., (2014) J. Mol. Evol. 79, 179-192; and Caschera, f. & Noireauz, V. (2014) Curr. Opin. Chem. Biol. 22, 85-91, each of which is incorporated herein by reference in its entirety. SMCs of the invention which include multiple genes can be prepared using methods presented herein in conjunction with routine procedures known in the art. Methods and components for liposomal encapsulation are known in the art and can be used in the preparation of SMCs of the invention.

SMCs of the invention can be used to make functional proteins using encapsulated systems reconstituted from recombinant cell-free translation factors and/or cell-free extracts from bacterial and/or eukaryotic cells. Unlike previous liposomal SMCs, which were used to express single genes and to synthesize a single gene product within a homogenous population of liposomes, certain embodiments of the present invention include SMCs that comprise multi-component genetic circuits, for example two, three, four, five, or more different genes that synthesize two, three, four, five or more different gene products, respectively. In addition, certain embodiments of the invention include preparation and use of SMCs that include multi-component circuits that can operate across multiple well-compartmentalized SMCs. The invention, in some aspects, includes strategies for constructing and utilizing such networks of SMC-based genetic circuits, thus expanding the control and amplification capacities of SMCs. Engineered networks of SMCs of the invention can be used to support complex chemical reactions that benefit from both the high-fidelity isolation of multiple reactions from one another, as well as controlled communication and regulatory signal exchange between those reactions.

Cascade circuits of the invention, in which the product of one gene triggers the production of the next, are useful for a variety of reasons for signal amplification (i.e., a relatively small input signal can trigger a high output), for modularity (e.g., a variety of sensors can be connected to a given output), and to enable multi-node control at various points within the network (as in the configuration of natural signaling and metabolic pathways in cells), where many reagents must be regulated in timing and concentration, for efficient synthesis. In some aspects of the invention, two or more SMCs that operate in conjunction with each other are also referred to herein as a "network" of SMCs. As used herein the term "network" used in conjunction with SMCs means two or more SMCs that interact with each other and can function as a system. A non-limiting example of a means by which two or more SMCs interact is chemical communication between SMCs. For example, though not intended to be limiting, as at least part of a network of SMCs, a first SMC releases an agent that contacts a second SMC and acts as a signal that triggers an action in the second SMC. Further to the foregoing example, in some aspects of the invention, after receiving the signal from a first SMC, a second SMC then release a signal that triggers an action in one or more of the first SMC, a third, fourth, or other SMC. In some embodiments of the invention, communication between two SMCs is one-directional communication and in certain embodiments of the invention communication between two SMCs is bi-directional communication.

As used herein in reference to gene expression, the term "cascade" means triggering (also referred to herein as "inducing") two or more events by an agent. In certain aspects of the invention, a triggered event may be expression of a polypeptide in one or more SMCs. For example, though not intended to be limiting, a small molecule may contact an SMC of the invention and trigger expression of one or more polypeptides from genes contained in the SMC. The one or more polypeptides may in turn induce expression of one or more additional polypeptides within the SMC or within a second SMC or a plurality of SMCs. In some aspects of the invention, a cascade amplifies expression of at least one polypeptide in at least one of a first SMC, a second SMC, or a plurality of SMCs. In another non-limiting example of a cascade, a polypeptide comprising a membrane channel or membrane pump may be expressed in an SMC of the invention and following that expression, the channel permits passage (entry and/or exit) of agents such as small molecules, polypeptides, ions, etc. into or out of the SMC. The agents may then trigger additional expression in the SMC or in a second or a plurality of SMCs that are contacted by the agent(s) that passed through the expressed channel. Non-limiting examples of polypeptides comprising membrane channels and polypeptides that comprise membrane pumps are light-activated ion channels and light-activated ion pumps, respectively. Light-activated ion channels polypeptides and light-activated ion pump polypeptides suitable for use in methods and compositions of the invention are known in the art. Methods suitable to prepare and use expression vectors, polynucleotide sequences, promoters, delivery agents, labeling agents, etc. to express polypeptides in SMCs of the invention are known in the art.

In addition to preparing and using multi-component genetic circuits that are encapsulated within liposomes, the invention in some aspects also includes created systems in which specific circuit elements are compartmentalized within different sets of liposomes within the same external solution. Such compartmentalization can serve key purposes not typically utilized in conventional synthetic biology: for example, in circumstances when a product of one genetic cascade is toxic to one or more parts of a second cascade, or in methods of tuning two genetic cascades that require dramatically different concentrations of a co-factor there are numerous examples throughout chemistry of reactions being run under specialized, and thus necessarily isolated, reaction conditions. Certain embodiments of liposome circuits of the invention (e.g., SMC-based circuits) can operate in parallel with other liposomal circuits of the invention without crosstalk between the circuits. Thus, certain aspects of the invention include populations of SMCs liposomes that respond differently to the same external activator and use of such SMCs.

In some aspects the invention includes multiple genetic circuits prepared in separate populations of liposomes, wherein communication modalities between the populations are present. In this way, compositions of the invention include entire compartmentalized genetic circuits—which allows the circuits to be separated (also referred to as being "isolated" from others) for reasons of control fidelity, toxicity, or reagent tunability—and to connect one or more compartmentalized circuits of the invention to other compartmentalized circuits. This aspect of the invention permits modularity between genetic circuits by physically separating circuit elements into different liposomes.

Although certain reactions are possible using well-compartmentalized environments of SMCs of certain aspects of the invention, some embodiments of SMCs of the invention can be used to bring together two or more genetic cascades into one environment at a particular time. For example, SMCs of the invention can be used in situations where two precursors require synthesis in different milieus, but then ultimately must be reacted to one another. As another non-limiting example, one or more proteins can be expressed at high yield in a bacterial expression system using an SMC of the invention, and the protein may receive post-translational modifications from eukaryotic cell lysate.

The terms "liposomes" and "synthetic minimal cells" are used interchangeably herein. As used herein a synthetic minimal cell is a liposome bioreactor that under suitable conditions is able to perform some of the biochemical functions of a living cell, most notably transcription and translation for the expression of proteins. SMCs of the invention may be prepared using methods described herein in conjunction with known methods for vector preparation, gene selection, recombinant techniques, expression conditions, etc. known in the art.

An SMC of the invention may comprise one or more expression vectors, also referred to as expression constructs. As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. Vectors capable of directing the expression of genes to which they are operatively linked are referred to herein as "expression vectors".

A non-limiting example of an expression vector used in SMCs and methods of the invention may be a plasmid or virus that includes one or more elements such as a gene of interest, an enhancer, a promoter, etc. In certain aspects of the invention, a promoter may be an inducible promoter. An expression vector introduces one or more genes of interest into an SMC of the invention. Under appropriate conditions, (as a non-limiting example—when triggered or induced) the presence of expression vector results in expression of at least one polypeptide of interest in the SMC. A vector useful in methods and SMCs of the invention may include regulatory sequences such as one or more of an enhancer region and a promoter region that participate in effective transcription of a gene of interest also included in the vector.

In certain aspects of the invention, non-limiting examples of a polypeptide of interest may be: a membrane channel polypeptide (also referred to herein as a "pore"), a membrane pump polypeptide, a detectable label, an agonist polypeptide, an antagonist polypeptide, a therapeutic polypeptide, a polypeptide that triggers expression of a second polypeptide, etc. In some embodiments of the invention a channel polypeptide or a membrane pump polypeptide may be light-activated polypeptides, which are also referred to as optogenetic polypeptides. As used herein, the term "channel" refers to a membrane channel protein that permits transport of agents across a cell membrane. As used herein, the term "agent" used in reference to a channel, may be a small molecule, an ion, a polypeptide, etc. Crossing through a membrane channel may occur via active or passive transport. Membrane channels and agents that cross membrane channels are routinely prepared and utilized in the art and means for their preparation and use will be understood by the skilled artisan and their use is routinely practiced in the relevant arts. In certain embodiments of the invention SMCs may be useful to prepare and collect quantities of a polypeptide for use in therapeutic methods. A therapeutic polypeptide can be expressed using an SMC of the invention that includes an expression vector comprising the gene encoding the polypeptide. In certain instances, quantities of a therapeutic or other polypeptide can be prepared using SMCs of the invention in quantities sufficient for collecting the polypeptide for further study, purification, administration, etc. A polynucleotide sequence of a gene included in an expression vector in an SMC of the invention may be a wild-type, recombinant, or mutant polynucleotide sequence. A polypeptide expressed in SMCs by the gene may have an amino acid sequence of a wild-type, mutant, or recombinant polypeptide. Examples of polypeptides and their encoding genes that may be utilized in methods and SMCs of the invention are described herein, and it will be understood that the examples are not limiting and that SMCs of the invention can be engineered to express numerous types of polypeptides.

Non-limiting examples of molecules that may be included in SMCs of the invention are vectors and their encoded polypeptides. Examples of encoded polypeptides that may expressed in SMCs of the invention include, but are not limited to: channel polypeptides, pore polypeptides, opsin polypeptides, detectable label polypeptides, trafficking polypeptides, signal polypeptides, export polypeptides, etc.

Non-limiting examples of detectable label polypeptides, that may be expressed in an SMC of the invention include: green fluorescent protein (GFP); enhanced green fluorescent protein (EGFP), red fluorescent protein (RFP); yellow fluorescent protein (YFP), tdTomato, mCherry, DsRed, cyan fluorescent protein (CFP); far red fluorescent proteins, etc.

Non-limiting examples of promoters that may be included in SMCs of the invention are mammalian and bacterial promotors such as, but not limited to, Lac, T7, P70, human ubiquitin C (UBC), PBAD, promoters and functional variants thereof. Methods to select and include promoters in vectors are well known in the art.

Methods for selecting and using trafficking sequences, signal sequences, export sequences, promoters, etc. in vectors for expression as fusion proteins are known in the art, see for example: Chow, X. et al., Nature 463, 98-102 (2010), Gradinaru, V. et al., Brain Cell Biol. 36, 129-139 (2009); and Kugler, S. et al., Gene Therapy 10, 337-347, (2003). The content of each of the above references is incorporated herein by reference in its entirety. Those skilled in the art will be able to use routine methods to prepare vectors encoding trafficking, signal sequences, export sequences, etc. for use in certain embodiments of SMCs of the invention.

Expression vectors and methods of their use for expression of numerous different types of polypeptides are well known in the art. Non-limiting examples of suitable expression vectors and methods for their use are provided herein. A skilled artisan will understand how to design and use expression vectors in methods and SMCs of the invention using routine procedures in conjunction with the disclosure provided herein.

As used herein, the term "plurality" used in reference to SMCs of the invention, means: at least 2, 3, 4, 5, 6, 7, 8, 9, 10, 50, 100, 1000, 10,000 or more SMCs. In some aspects of the invention, each SMC in a plurality of SMCs includes the same one or more: expression vectors, genes of interest, and may be induced to express one or more genes by the same agents as the other SMCs in the plurality of SMCs. In certain aspects of the invention each SMC in a plurality of SMCs may include one or more different: expression vectors, genes of interest, internal environment than one or more other SMCs in the plurality and may be induced to express one or more genes by at least one different agent than induces expression of a gene of interest in one or more of the other SMCs in the plurality of SMCs. Thus, in some aspects of the invention a plurality of SMCs may be homogeneous and in certain aspects of the invention a plurality of SMCs may be heterogeneous.

In certain aspects of the invention, an SMC (also referred to as a liposome) of the invention, can be programmed to be fused together with another SMC. Liposome fusion can be implemented using any suitable fusion system, including but not limited to a system utilizing SNARE/coiled-coil hybrid proteins, which can be generated in complementary pairs that are specific in their fusion properties [see for example: Meyenberg, K. et al., Chem. Commun. 47, 9405 (2011) and Robson Marsden, H. et al., Biomater. Sci. 1, 1046 (2013), each of which is incorporated by reference herein in its entirety]. In the non-limiting SNARE fusion system example, complementary fusion elements can be packaged into separate populations of SNARE-fusable SMCs of the invention and the SMCs can be fused together. In certain embodiments of the invention, fusion elements are present on the exterior surface of an MSC. In some aspects of the invention, complementary fusion elements are present on the exterior surfaces of two or more MSCs in a population of MSCs. The fraction of occupied SMC within each population can be independently calibrated making it possible to tune the overall production of the final output, as well as the degree of modulation by environment. In some aspects of the invention, SMCs undergoing SNARE-mediated fusion may form large aggregates made from multiple starter SMCs.

Use of SMCs of the Invention

SMCs and pluralities of SMCs of the invention may be used in various methods including, but not limited to: assessing expression network activity, synthesizing one or more polypeptides of interest, examining gene interactions, testing and assessing effects of conditions and agents on gene expression, etc. In certain aspects of the invention, a plurality of SMCs that express a protein of interest can be prepared and the polypeptide of interest synthesized in the SMCs can be collected. The effect on gene expression that results from altering the internal and/or external environment of an SMC can also be examined using methods of the invention. The environment may be altered by contacting an SMC with an agent, including in an SMC a gene that when expressed alters the internal environment of the SMC, etc.

In certain aspects of the invention, SMCs can be prepared and used to model a biological process. This may be done by preparing a plurality of SMCs and assessing one or more characteristics of the plurality of SMCs such as internal and external interactions, density effects, etc. In some studies of biological processes, one or more activities of one or more of multi-gene genetic circuits can be altered using agents, temperature, density, etc. and the effects such as interactions between genes within an SMC, communication between SMCs, interactions between genes in different SMCs, etc. can be monitored, measured, and assessed.

Some aspects of the invention include using SMCs to assess whether expression of a first gene in a first SMC has a modulating effect of expression of a gene in second SMC. Thus, interactions and communication between SMCs can be assessed. A non-limiting example of such a method includes preparing two SMCs having independently selected genes in one or more multi-gene genetic circuits; expressing a first gene in the first SMC; determining the presence or absence of a modulation of expression of the same or a different gene in the second SMC.

Additional uses for SMCs of the invention include, but are not limited to testing the effect of one or more candidate compounds on an activity of a multi-gene genetic circuit, the method comprising, contacting an SMC with candidate compound; and comparing an activity of a gene of a multi-gene genetic circuit of the SMC with the activity in a control SMC that was not contacted with the candidate compound. A change between the activity in the contacted SMC compared to the control SMC indicates an effect of the candidate compound on the test SMC. A control SMC in such an example may be an SMC that includes the gene components of the SMC that is contacted with the candidate compound, but that is not itself contacted. The SMCs can be monitored for the presence or absence of a change that occurs in the contacted conditions versus the control conditions. For example, change may be an increase (or decrease) in expression of a gene in the multi-gene genetic circuit of the SMC that is contacted versus the non-contacted control. Art-known methods can be used in conjunction with methods described herein to assess changes in contacted versus non-contacted multi-gene genetic circuits in SMCs of the invention.

EXAMPLES

Example 1

Studies were performed to assess whether characteristics of liposomal compartmentalization such as robustness to external dilution (e.g., when administered into external environments for use as sensors, or if diluted during processes related to the administration or removal of external factors), and facilitated reaction efficacy due to molecular crowding (because confining reactants within a liposome facilitates their interaction due to the small volume) can help support multi-component genetic circuits as well as chemical reactions of higher order.

Figure 1B:
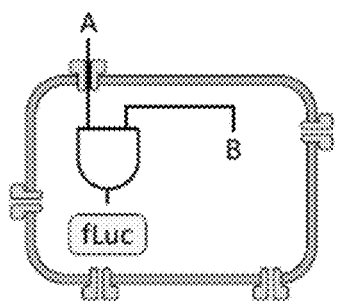
Figure 1C:
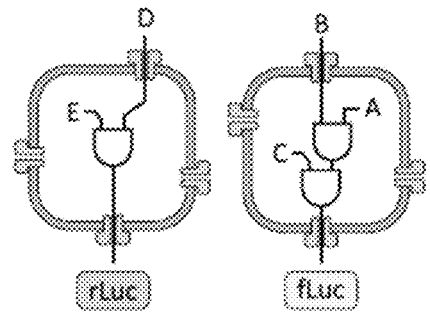
Figure 1D:
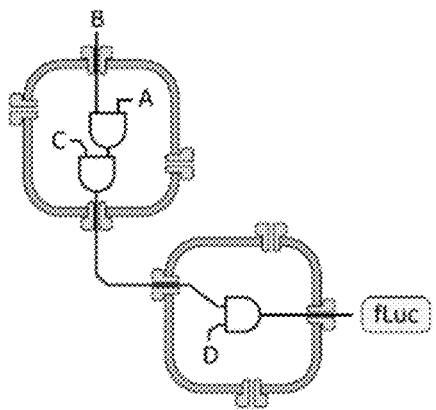
Figure 1E:
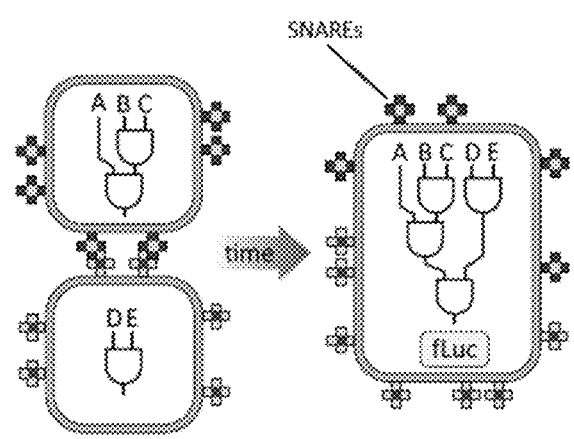

Studies have now been performed to assess a key issue in synthetic biology: the modularity of multi-component genetic circuits and cascades. The results have now shown that by encapsulating genetic circuits and cascades within synells (FIGS. 1A and B) and orchestrating the synells to either operate in parallel (FIG. 1C), communicate with one another (FIG. 1D), or fuse with one another in a controlled way (FIG. 1E), it is now possible to create and utilize genetic cascades that take advantage of the modularity enabled by liposomal compartmentalization. The strategy of the experiments described below herein, have enabled genetic cascades to proceed in well-isolated environments while permitting the desired degree of control and communication. Examples of certain design strategies for constructing and utilizing such synell networks are provided herein, thus expanding the utility of liposome technology and improving the modularity of synthetic biology. Synell networks may support complex chemical reactions that would benefit from both the high-fidelity isolation of multiple reactions from one another, as well as controlled communication and regulatory signal exchange between those reactions. Shown herein, for example, are studies and results demonstrating successful controlled fusion of two populations of synells that contain mammalian transcriptional and mammalian translational machinery, respectively, which are normally incompatible when combined in the same compartment. Methods of the invention permit can be used in some instances for successful fusions that were not previously possible.

Materials & Methods:

Sources of materials and product characterization

The vectors used in the experiments described herein were synthesized in-house, from oligonucleotide gBlocks from IDT (IDT DNA, Coralville, Iowa, US) or DNA oligo building blocks from Epoch (Epoch Life Science Inc., Sugar Land, Tex., US). The sequence of all plasmids was confirmed by Sanger Sequencing by Eton Bioscience Inc. (San Diego, Calif., US) or Quintara Bio (Boston, Mass., US). Unless otherwise stated, small molecules, activators and buffer components, were purchased either form Sigma Aldrich (St. Louis, Mo., US) or Thermo Fisher (Waltham, Mass., US) and were used without further purification. All antibiotics used for cloning and TL/TL preparation were purchased from GoldBio (Olivette, Mo., US) and used without further purification. All experiments were performed in buffers prepared using RNAse free water from Ambion (sold by Thermo Fisher). The lipids used for liposome formation were purchased from Avanti Polar Lipids (Alabaster, Ala., US) and were used without further purification. The enzyme products obtained in cell-free reactions were characterized with commercially available detection kits: Renilla, NANOLUC® and Firefly luciferases using products from Promega (Madison, Wis., US); Beta-lactamase, Chloramphenicol acetyltransferase and Beta-galactosidase using product from Thermo Fisher (Waltham, Mass., US).

Liposome Preparation

Liposomes were prepared according to methods described in Lentini, R. et al., (2014) Nat. Commun. 5, 4012 and Spencer, A. C. et al., (2013) J. Vis. Exp. 1-7. In particular, a chloroform solution of 20 mg (26 μmol) of POPC (Avanti Polar Lipids) and 20 mg (52 mmol) of cholesterol (Avanti Polar Lipids) was evaporated into a thin film using a round bottom flask. 4 mL of DEPC-treated nuclease-free water was added to the flask and vigorously vortexed for ~3 minutes. The liposome solution (~6.5 mM) was then homogenized with a hand-held homogenizer (IKA) for ~1 minute. The mixture was divided into 1504 aliquots (~1 μmol of lipid each) and lyophilized until dry.

The final experimental liposome solution was prepared by hydrating aliquots of lyophilized lipids with buffer containing the cell-free TX/TL extract, DNA, and small molecule activators for each experiment, to the final volume of 50 μL per reaction (~20 mM liposomes). Liposomes were extruded through a 1 μM polycarbonate track-etched membrane (Whatman). The unencapsulated solutes were removed from liposomes through dialysis using a liposome dialyzer as described previously in Adamala, K. et al., (2015) Nat. Protoc. 10, 927-938, with 0.5 mL volume slide-a-lyzer chamber and a 0.1 μM pore size internal polycarbonate track-etched membrane (Whatman). The dialysis was performed at 4° C. The samples were dialyzed 5 times against Dialysis Buffer (50 mM HEPES, pH=7.6, 100 mM KCl, 10 mM $MgCl_2$ and ~10 mM empty and unlabeled POPC-cholesterol liposomes), with a buffer change every 10 minutes and 3 additional buffer changes every 20 minutes.

Cloning of Expression Constructs:

The UBC (human ubiquitin C promoter, GenBank: D63791.1), P70 (OR2-OR1-Pr) [see: Shin, J. et al., J. Biol. Eng. 4, 8 (2010)], and Lac (Llac-0-1) [see: Lutz, R. et al., (1997) Nucleic Acids Res. 25, 1203-1210] promoter constructs were used in a modified pCI vector (Promega). The original promoter region of the vector was replaced by the appropriate promoter to make the constructs as described herein. [See: Lutz, R. et al., (2007) Nucleic Acids Res. 25, 1203-1210]. For bacterial expression, the previously described transcription terminator T500 was added at the end of each ORF. The original UTR was also removed and replaced with the previously described UTR1 [Shin, J. et al., (2010) J. Biol. Eng. 4, 8]. The mammalian Tet constructs were built into Tet-On 3G bi-directional vector (Clontech) by cloning the genes into MCS1. The araBAD constructs were built using a PBAD vector [Guzman, L M. et al., (1995) J. Bacteriol. 177, 4121-30] (Thermo). PBAD-hisB was used, removing the His-tag and the enterokinase recognition site prior to inserting the genes used in investigations described herein.

Flow Cytometry with GFP and Split GFP

Fluorescence signal from these GFP liposomes was measured after 12 h of incubation for the experiments in FIGS. 2B-D. Membranes (red fluorescence) were labeled with LISSAMINE™ Rhodamine B 1,2-Dihexadecanoyl-sn-Glycero-3-Phosphoethanolamine Triethylammonium Salt (rhodamine DHPE), used at 0.2 molar percentage of the POPC concentration. GFP was expressed from a plasmid with the T7 promoter. The halves of split GFP were fused to complementary coiled coils and expressed from two different plasmids (both with the T7 promoter). Flow cytometry analysis: events in two fluorescent channels were analyzed: GFP and red fluorescence. Each dataset consists of minimum 19,000 events. FIG. 2C shows an analysis of liposomes expressing GFP and FIG. 2D shows an analysis of liposomes expressing split GFP. The percentage of liposomes expressing protein was calculated as the percentage of events in the quadrant positive in both green and red channels (Q2 on both plots). The flow cytometer was not calibrated using size standards, therefore all information about the size of the particles in the experiment are approximate. For the detailed size measurements of the liposomes in this work see FIG. 26 from the DLS experiments. The flow cytometry analysis was performed on FACSCANTO™ II Flow Cytometry System, and the data analysis was performed using BD FAC-SDIVA™ 8.0 Software.

Firefly Luciferase Assays:

Firefly luciferase (fLuc) activity was assayed using the STEADY-GLO® Luciferase Assay System (Promega). The protein analysis was performed according to the manufacturer's instructions. The cell lysis protocol was replaced with a modified procedure for lysing liposome-encapsulated expression reactions. The 50 µL liposome reactions were quenched by 10 µL of Quench Mix containing 0.3% v/v Triton-X100 (to disrupt vesicles), TURBO™ DNAse (Thermo; final concentration ~2 U/60 µL; 1 µL used), TURBO™ DNAse buffer (final concentration 0.5×, 2.5 µL 10× stock used), RNase Cocktail Enzyme Mix (Thermo, mixture of RNAse A and RNAse T1, 3 µL per 60 µL reaction). The samples were incubated with the Quench Mix for 15 min at 37° C. The resulting sample was used directly with the STEADY-GLO® luciferase assay, according to the manufacturer's instructions. The result is given in RLU—relative light units with 10 s integration time.

Enzyme Activity Assays

Renilla, NANOLUC® luciferase, Beta-lactamase, Beta-galactosidase and Chloramphenicol acetyltransferase activity were assayed using commercially available kits, according to the manufacturer's instructions. Detailed procedures are provided herein.

Renilla Luciferase Assays:

Renilla luciferase (rLuc) activity was assayed using the Renilla Luciferase Assay System (Promega). Liposome reactions were stopped using Quench Mix according to the procedure described in the Firefly luciferase assays section above. The resulting sample was used directly with the Renilla luciferase assay, according to the manufacturer's instructions. The result is given in RLU—relative light units with 10 s integration time.

NANOLUC® Luciferase Assays:

NANOLUC® luciferase activity was assayed using the NANO-GLO® Luciferase Assay System (Promega). Liposome reactions were stopped using Quench Mix according to the procedure described in the Firefly luciferase assays section above. The resulting sample was used directly with the NANO-GLO® luciferase assay, according to the manufacturer's instructions.

Beta-Lactamase Assays:

Beta-lactamase activity was assayed using the LyticBLAzer-FRET B/G assay kit (Thermo Fisher Scientific). Liposome reactions were stopped using Quench Mix according to the procedure described in the Firefly luciferase assays section above. The resulting sample was used directly with the beta-lactamase assay, according to the manufacturer's instructions.

Beta-Galactosidase Assays:

Beta-galactosidase activity was assayed using the β-Gal Assay Kit (Thermo Fisher Scientific). Liposome reactions were stopped using Quench Mix according to the procedure described in the Firefly luciferase assays section above. The resulting sample was used directly with the beta-galactosidase assay, according to the manufacturer's instructions.

Chloroamphenicol Acetyltransferase Assays:

Chloroamphenicol acetyltransferase activity was assayed using the FAST CAT® Green (Deoxy) Chloramphenicol Acetyltransferase Assay Kit (Thermo Fisher Scientific). Liposome reactions were stopped using Quench Mix according to the procedure described in the Firefly luciferase assays section above. Samples were then heated to 65° C. for 10 minutes, to inactivate endogenous acetylating enzymes. [See: Crabb, D. W. et al., (1978) Anal. Biochem. 163, 88-92]. The resulting samples were used directly with the FAST CAT® assay according to the manufacturer's instructions. GR ACS Silica Gel Grade 12 28-200 Mesh plates (EMD Millipore) were used for product analysis. After visualization, the product and substrate spots were scraped from the plate and mixed with 0.35 mL of methanol per spot. The samples were centrifuged for 1 min, a 200 µL aliquot of each methanol solution was removed, and the fluorescence of both substrate and product was quantified (excitation 490 mm, emission 525 mm).

E. coli Cell-Free TX/TL Extract:

The E. coli cell-free extract was prepared according to the Noireaux lab protocol, from Rosetta 2 BL21 cells (Novagen). [See: Shin, J. et al., (2010) J. Biol. Eng. 4, 8. and Sun, Z. Z. et al., (2013) J. Vis. Exp. 1-15]. The entire extract preparation was prepared in a cold room (4° C.).

HeLa Cell-Free Extract:

The HeLa cell-free extract was prepared according to the methods described in Mikami, S. et al., (2006) Protein Expr. Purif. 46, 348-57. The entire extract preparation was prepared in a cold room (4° C.). For the mammalian in vitro transcription, the HeLa cell-free nuclear fraction transcription system HELASCRIBE® Nuclear Extract (Promega) was used according to Manufacturer's instructions.

SNARE Protein Mimics:

SNARE protein mimics were chemically synthesized by solid phase protein synthesis (Genscript). SNARE-A was a fusion of the E3 coiled-coil motif and the trans-membrane region of the VAMP2 protein (residues 85-116). SNARE-B was a fusion of the K3 coiled-coil motif with a trans-membrane region from syntaxin-1A protein (residues 258-288), as previously described by Meyenberg, K. et al., (2011) Chem. Commun. 47, 9405. The SNARE peptide-to-lipid molar ratio used in all experiments was 1:500.

It was observed that liposomes undergoing SNARE-mediated fusion will form large aggregates made from multiple starter liposomes [see: Myenberg, K., et al. (2011) Chem. Commun. 47: 9405-9407 and Robson Marsden, H., et al. (2013) Biomater. Sci. 1:1046-1054]. This does not affect the results shown in FIG. 6, but is likely to reduce the molecular confinement effects observed in FIG. 3.

Methods, Results, & Discussion

In one example, cell-free transcription/translation (TX/TL) reactions that produce firefly luciferase (fLuc) from one, two, or three protein components were tested both in bulk solution and in synthetic minimal cells (SMCs). In this experiment, HeLa cell extract [Weber, L. A. et al., Biochemistry 14, 5315-5321 (1975); Molla, A. et al., Science 254 (5038), 1647-51 (1991); Mikami, S et al., Protein Expr. Purif. 46, 348-57 (2006); and Mikami, S et al., Protein Expr. Purif. 62, 190-198 (2008)] was used to constitutively express the Tet protein to mediate small molecule induction of transcription of the one, two, or three fLuc components, as well as alpha-hemolysin (aHL), which serves as a pore to admit doxycycline (Dox) to trigger Tet function [Noireaux, V. et al., Proc. Natl. Acad. Sci. U.S.A 101, 17669-17674 (2004); Stefureac, R. et al., Biochemistry 45, 9172-9179 (2006); and Gouaux, E. et al., Protein Sci. 6(12), 2631-5 (1997)] (FIG. 3A). All experiments shown in FIG. 3 start with liposomes containing mammalian transcription-translation (TX/TL) extract and constitutively expressing the alpha-hemolysin (aHL) and mammalian Tet protein. The one-component luciferase was conventional monolithic fLuc (FIG. 3B); the two-component system (to explore $2^{nd}$-order reactions) comprised the two halves of split firefly luciferase, each attached to a coiled coil and a split intein fragment to bring the halves together and covalently bridge them (FIG. 3C) [Selgrade, D. F. et al., J. Am. Chem. Soc. 135(20), 7713-9 (2013)]; and the three-component system involved the halves of split firefly luciferase bearing coiled-coils and split inteins, with the coiled-coils targeting a third protein, a scaffold (FIG. 3D) [Selgrade, D. F. et al., J. Am. Chem. Soc'y 135(20), 7713-9 (2013)].

For all three orders of luciferase-producing reactions, the effect of dilution on fLuc expression was weaker for liposomes than for bulk solution (FIGS. 3E-3G; P<0.0001 for interaction between factors of encapsulation and dilution factor; ANOVA with factors of encapsulation and dilution factor; see Tables 1A and B, 2A and B, and 3A and B for full statistics). Note that for all tables herein the following abbreviations apply: "Difference" is "Diff."; "Not significant" is "ns"; "Confidence interval" is "CI"; "Number of parameters" is "Nparm"; "degrees of freedom" is "DF"; "Significant" is "*"; and "More significant" is "****".

Table 1

TABLE 1A

Statistics for FIG. 3E: 2-way ANOVA with factors of "Dilution Factor" and "Encapsulation".

| Source of Variation | % of total variation | P value | P value summary | Significant? |
|---|---|---|---|---|
| Interaction | 29.8 | <0.0001 | **** | Yes |
| Dilution Factor | 57.94 | <0.0001 | **** | Yes |
| Encapsulation | 3.859 | 0.0002 | *** | Yes |

TABLE 1B

Dunnett's multiple comparisons test after the ANOVA.

| | Mean Diff. | 95% CI of diff. | Significant? | Summary | Adjusted P Value |
|---|---|---|---|---|---|
| Liposome | | | | | |
| 2 vs. 1 | −500.6 | −1552 to 551.2 | No | ns | 0.6003 |
| 4 vs. 1 | −496 | −1548 to 555.9 | No | ns | 0.6084 |
| 6 vs. 1 | −1005 | −2057 to 46.55 | No | ns | 0.0652 |
| 8 vs. 1 | −1106 | −2158 to −54.09 | Yes | * | 0.0364 |
| 10 vs. 1 | −913.1 | −1965 to 138.7 | No | ns | 0.1071 |
| Solution | | | | | |
| 2 vs. 1 | −2631 | −3683 to −1579 | Yes | **** | <0.0001 |
| 4 vs. 1 | −3916 | −4968 to −2865 | Yes | **** | <0.0001 |
| 6 vs. 1 | −5429 | −6481 to −4378 | Yes | **** | <0.0001 |
| 8 vs. 1 | −5917 | −6969 to −4866 | Yes | **** | <0.0001 |
| 10 vs. 1 | −6358 | −7409 to −5306 | Yes | **** | <0.0001 |

Table 2

TABLE 2A

Statistics for FIG. 3F: 2-way ANOVA with factors of "Dilution Factor" and "Encapsulation".

| Source of Variation | % of total variation | P value | P value summary | Significant? |
|---|---|---|---|---|
| Interaction | 38.48 | <0.0001 | **** | Yes |
| Dilution Factor | 50.55 | <0.0001 | **** | Yes |
| Encapsulation | 1.665 | 0.0156 | * | Yes |

TABLE 2B

Dunnett's multiple comparisons test after the ANOVA.

| | Mean Diff. | 95% CI of diff. | Significant? | Summary | Adjusted P Value |
|---|---|---|---|---|---|
| Liposome | | | | | |
| 2 vs. 1 | −27.26 | −177.3 to 122.8 | No | Ns | 0.9854 |
| 4 vs. 1 | −42.54 | −192.6 to 107.5 | No | Ns | 0.9129 |
| 6 vs. 1 | −26.02 | −176.1 to 124.1 | No | Ns | 0.9881 |
| 8 vs. 1 | −29.94 | −180.0 to 120.1 | No | Ns | 0.9781 |
| 10 vs. 1 | −97.95 | −248.0 to 52.13 | No | Ns | 0.31 |
| Solution | | | | | |
| 2 vs. 1 | −385.3 | −535.4 to −235.2 | Yes | **** | <0.0001 |
| 4 vs. 1 | −582.8 | −732.9 to −432.8 | Yes | **** | <0.0001 |
| 6 vs. 1 | −753.1 | −903.2 to −603.0 | Yes | **** | <0.0001 |

TABLE 2B-continued

Dunnett's multiple comparisons test after the ANOVA.

| | Mean Diff. | 95% CI of diff. | Significant? | Summary | Adjusted P Value |
|---|---|---|---|---|---|
| 8 vs. 1 | −827.7 | −977.7 to −677.6 | Yes | **** | <0.0001 |
| 10 vs. 1 | −878.8 | −1029 to −728.7 | Yes | **** | <0.0001 |

Table 3

TABLE 3A

Statistics for FIG. 3G: 2-way ANOVA with factors of "Dilution Factor" and "Encapsulation".

| Source of Variation | % of total variation | P value | P value summary | Significant? |
|---|---|---|---|---|
| Interaction | 25.06 | <0.0001 | **** | Yes |
| Dilution Factor | 34.95 | <0.0001 | **** | Yes |
| Encapsulation | 33.06 | <0.0001 | **** | Yes |

TABLE 3B

Dunnett's multiple comparisons test after the ANOVA.

| | Mean Diff. | 95% CI of diff. | Significant? | Summary | Adjusted P Value |
|---|---|---|---|---|---|
| Liposome | | | | | |
| 2 vs. 1 | 15.96 | −54.75 to 86.66 | No | Ns | 0.9637 |
| 4 vs. 1 | 0.3899 | −70.32 to 71.10 | No | Ns | >0.9999 |
| 6 vs. 1 | −14.33 | −85.03 to 56.38 | No | Ns | 0.9767 |
| 8 vs. 1 | −22.41 | −93.11 to 48.30 | No | Ns | 0.8716 |
| 10 vs. 1 | −44.25 | −115.0 to 26.45 | No | Ns | 0.3474 |
| Solution | | | | | |
| 2 vs. 1 | −228.6 | −299.3 to −157.9 | Yes | **** | <0.0001 |
| 4 vs. 1 | −314.7 | −385.4 to −244.0 | Yes | **** | <0.0001 |
| 6 vs. 1 | −345.7 | −416.4 to −275.0 | Yes | **** | <0.0001 |
| 8 vs. 1 | −382.9 | −453.6 to −312.2 | Yes | **** | <0.0001 |
| 10 vs. 1 | −394.8 | −465.5 to −324.0 | Yes | **** | <0.0001 |

The fLuc expression was proportional to the concentration of Dox added to the external solution, and depended on aHL (FIGS. 3H-J). Liposomes produced lower amounts of fLuc than the same volume of TX/TL extract in bulk solution—likely due to the well-known property of stochastic loading of reagents into liposomes [De Souza, T. P. et al., Orig. Life Evol. Biosph. 42, 421-428 (2012) and De Souza, T. P. et al., J. Mol. Evol. 79, 179-192 (2014)] ($P<0.0001$ for factor of encapsulation in ANOVA with factors of time, encapsulation, and order; see Table 4 for full statistics).

TABLE 4

Statistics for FIGS. 3K-M: 3-way ANOVA with factors of "Time", "Encapsulation" and "Order".

| Source | Nparm | DF | Sum of Squares | F Ratio | Prob > F |
|---|---|---|---|---|---|
| Time | 1 | 1 | 3612860 | 3.7024 | 0.061 |
| Encapsulation | 1 | 1 | 20048169 | 20.5452 | <.0001 |
| Order | 2 | 2 | 218970231 | 112.1994 | <.0001 |

For the third-order reaction, the liposome encapsulation resulted in efficacy nearly equal to that of bulk solution ($P=0.1324$ for factor of encapsulation in ANOVA with factors of time and encapsulation; FIG. 3M; see Table 7 for full statistics), whereas for the first-order and second-order reactions the liposomes resulted in lower efficacy ($P<0.0001$ for factor of encapsulation in ANOVAs for both analyses, each with factors of time and encapsulation; FIGS. 3K and 3L; see Tables 5 and 6 for full statistics). Molecular crowding in liposomes thus may help facilitate higher-order reactions that require multiple chemical building blocks to be brought together, since the restricted movement of reagents increases the probability of the requisite multi-way interactions.

TABLE 5A

Statistics for FIG. 3K: 2-way ANOVA with factors of "Time" and "Encapsulation".

| Source of Variation | % of total variation | P value | P value summary | Significant? |
|---|---|---|---|---|
| Interaction | 1.308 | 0.2853 | Ns | No |
| Time | 13.82 | 0.0034 | ** | Yes |
| Encapsulation | 72.32 | <0.0001 | **** | Yes |

TABLE 5B

Sidak's multiple comparisons test after the ANOVA

| Solution - Liposome | Mean Diff. | 95% CI of diff. | Significant? | Summary | Adjusted P Value |
|---|---|---|---|---|---|
| 1 h | 2959 | 1474 to 4444 | Yes | *** | 0.0005 |
| 3 h | 3879 | 2394 to 5364 | Yes | **** | <0.0001 |

Table 6

TABLE 6A

Statistics for FIG. 3L: 2-way ANOVA with factors of "Time" and "Encapsulation".

| Source of Variation | % of total variation | P value | P value summary | Significant? |
|---|---|---|---|---|
| Interaction | 0.7342 | 0.5091 | Ns | No |
| Time | 4.334 | 0.1241 | Ns | No |
| Encapsulation | 75.91 | <0.0001 | **** | Yes |

TABLE 6B

Sidak's multiple comparisons test after the ANOVA

| Solution - Liposome | Mean Diff. | 95% CI of diff. | Significant? | Summary | Adjusted P Value |
|---|---|---|---|---|---|
| 1 h | 453.5 | 238.1 to 669.0 | Yes | *** | 0.0003 |
| 3 h | 372.3 | 156.9 to 587.8 | Yes | ** | 0.0017 |

Table 7

TABLE 7A

Statistics for FIG. 3M: 2-way ANOVA with factors of "Time" and "Encapsulation".

| Source of Variation | % of total variation | P value | P value summary | Significant? |
|---|---|---|---|---|
| Interaction | 4.032 | 0.4007 | Ns | No |
| Time | 18.41 | 0.0872 | Ns | No |
| Encapsulation | 13.84 | 0.1324 | Ns | No |

TABLE 7B

Sidak's multiple comparisons test after the ANOVA

| Solution - Liposome | Mean Diff. | 95% CI of diff. | Significant? | Summary | Adjusted P Value |
|---|---|---|---|---|---|
| 1 h | 70.26 | −31.80 to 172.3 | No | Ns | 0.1977 |
| 3 h | 21 | −81.06 to 123.1 | No | Ns | 0.8471 |

Figure 7A:
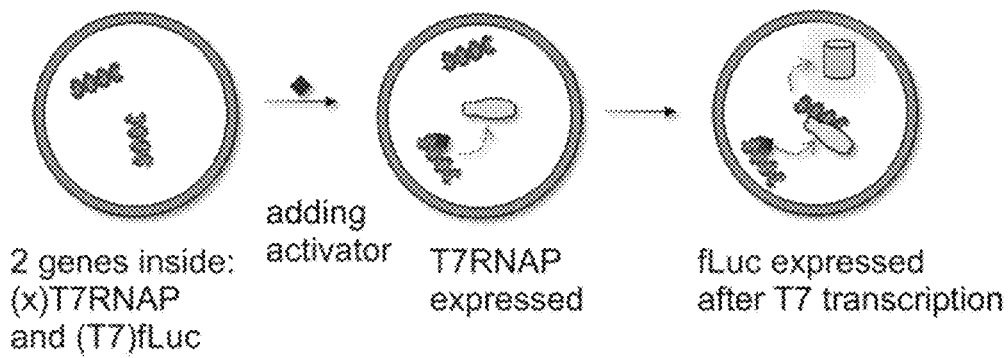
FIG. 7A-E provides schematic diagrams and graphs demonstrating activation of liposomally encapsulated cascaded genetic networks via membrane-permeant small molecules.

In another example, cascaded circuits were built using liposomes with *E. coli* TX/TL extract. The circuit constructed had the gene for fLuc (in single component form) under a T7 promoter (recognized by T7 RNA Polymerase, T7RNAP), with the gene for T7RNAP itself under the control of a membrane-permeable activator (FIG. 7A), here either theophylline (Theo, which activates an aptamer sequence in the 5'-UTR that un-masks a ribosome binding site and triggers protein production) or arabinose (Ara, which induces the PBAD promoter). These activators had been previously tested in phospholipid liposomes for the induction of single genes [Shin, J. et al., ACS Synth. Biol. 1, 29-41 (2012) and Lentini, R. et al., Nat. Commun. 5, 4012 (2014)].

Figure 7B:
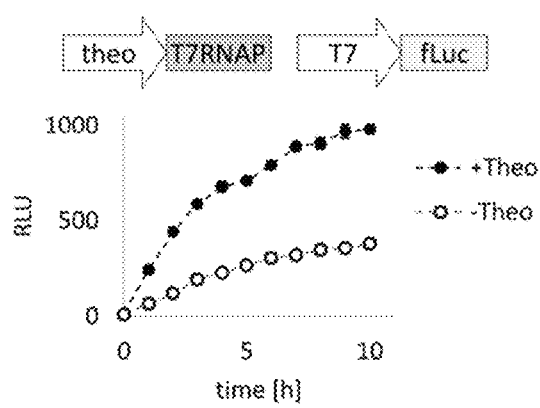
Figure 7C:
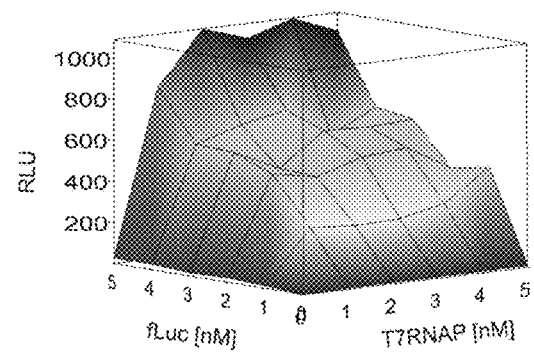

The theophylline system was observed to be leaky, as others have observed before [Lentini, R. et al., Nat. Commun. 5, 4012 (2014)] (expression for all time points after t=3 h was significantly different from that at t=0, P<0.0001 in Sidak's multiple comparison test, after ANOVA with factors of time and presence or absence of theophylline; FIGS. 7B and 7C; see Table 8 for full statistics).

Table 8

TABLE 8A

Statistics for FIG. 7B: 2-way ANOVA with factors of "Theophylline" and "Time".

| Source of Variation | % of total variation | P value | P value summary | Significant? |
|---|---|---|---|---|
| Interaction | 8.412 | <0.0001 | **** | Yes |
| Time | 44.57 | <0.0001 | **** | Yes |
| Theophylline | 45.6 | <0.0001 | **** | Yes |

TABLE 8B

Sidak's multiple comparisons test after the ANOVA

| | Mean Diff. | 95% CI of diff. | Significant? | Summary | Adjusted P Value |
|---|---|---|---|---|---|
| +Theo | | | | | |
| 1 vs. 0 | 226.3 | 138.7 to 313.9 | Yes | **** | <0.0001 |
| 2 vs. 0 | 425.5 | 337.9 to 513.1 | Yes | **** | <0.0001 |
| 3 vs. 0 | 571 | 483.4 to 658.6 | Yes | **** | <0.0001 |
| 4 vs. 0 | 661.8 | 574.2 to 749.4 | Yes | **** | <0.0001 |
| 5 vs. 0 | 693.7 | 606.1 to 781.3 | Yes | **** | <0.0001 |
| 6 vs. 0 | 774.6 | 687.0 to 862.2 | Yes | **** | <0.0001 |
| 7 vs. 0 | 872.3 | 784.7 to 959.9 | Yes | **** | <0.0001 |
| 8 vs. 0 | 889 | 801.4 to 976.6 | Yes | **** | <0.0001 |
| 9 vs. 0 | 953.3 | 865.7 to 1041 | Yes | **** | <0.0001 |
| 10 vs. 0 | 963.8 | 876.2 to 1051 | Yes | **** | <0.0001 |
| −Theo | | | | | |
| 1 vs. 0 | 55.64 | −31.96 to 143.2 | No | ns | 0.5177 |
| 2 vs. 0 | 109.1 | 21.53 to 196.7 | Yes | ** | 0.0059 |
| 3 vs. 0 | 181.2 | 93.57 to 268.8 | Yes | **** | <0.0001 |
| 4 vs. 0 | 217 | 129.4 to 304.6 | Yes | **** | <0.0001 |
| 5 vs. 0 | 256.2 | 168.6 to 343.8 | Yes | **** | <0.0001 |
| 6 vs. 0 | 294.4 | 206.8 to 382.0 | Yes | **** | <0.0001 |
| 7 vs. 0 | 309.6 | 222.0 to 397.2 | Yes | **** | <0.0001 |
| 8 vs. 0 | 337.4 | 249.8 to 425.0 | Yes | **** | <0.0001 |
| 9 vs. 0 | 345.4 | 257.8 to 433.0 | Yes | **** | <0.0001 |
| 10 vs. 0 | 368.8 | 281.2 to 456.4 | Yes | **** | <0.0001 |

Figure 7D:
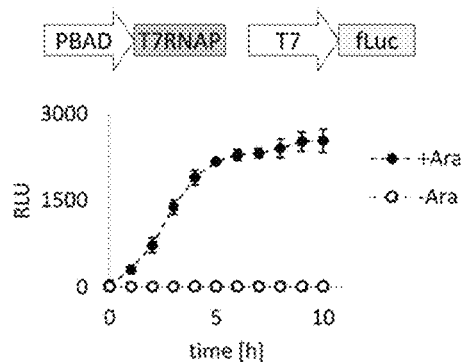
Figure 7E:
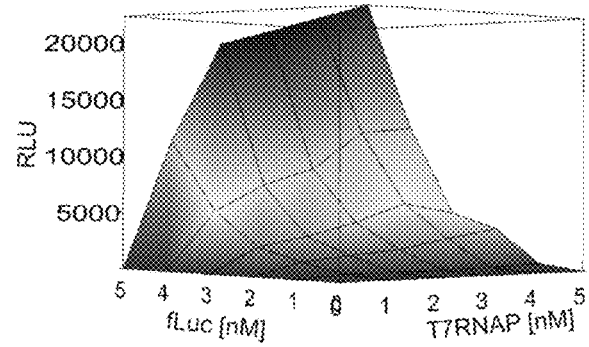

No measurable activation of PBAD in the absence of arabinose was found, suggesting that arabinose may be a useful external trigger for cascaded genetic circuits (expression for all time points was equal to that for t=0, P>0.9999 in Sidak's multiple comparison test, after ANOVA with factors of time and presence or absence of arabinose; FIGS. 7D and 7E; see Table 9 for full statistics).

Table 9

TABLE 9A

Statistics for FIG. 7D: 2-way ANOVA with factors of "Arabinose" and "Time".

| Source of Variation | % of total variation | P value | P value summary | Significant? |
|---|---|---|---|---|
| Interaction | 17.39 | <0.0001 | **** | Yes |
| Time | 17.5 | <0.0001 | **** | Yes |
| Arabinose | 63.1 | <0.0001 | **** | Yes |

TABLE 9B

Sidak's multiple comparisons test after the ANOVA

|  | Mean Diff. | 95% CI of diff. | Significant? | Summary | Adjusted P Value |
|---|---|---|---|---|---|
| +Ara |  |  |  |  |  |
| 1 vs. 0 | 253.7 | −99.71 to 607.1 | No | ns | 0.3454 |
| 2 vs. 0 | 675.2 | 321.8 to 1029 | Yes | **** | <0.0001 |
| 3 vs. 0 | 1332 | 978.8 to 1686 | Yes | **** | <0.0001 |
| 4 vs. 0 | 1838 | 1484 to 2191 | Yes | **** | <0.0001 |
| 5 vs. 0 | 2117 | 1764 to 2471 | Yes | **** | <0.0001 |
| 6 vs. 0 | 2232 | 1879 to 2586 | Yes | **** | <0.0001 |
| 7 vs. 0 | 2261 | 1908 to 2615 | Yes | **** | <0.0001 |
| 8 vs. 0 | 2344 | 1991 to 2698 | Yes | **** | <0.0001 |
| 9 vs. 0 | 2464 | 2110 to 2817 | Yes | **** | <0.0001 |
| 10 vs. 0 | 2480 | 2126 to 2833 | Yes | **** | <0.0001 |
| −Ara |  |  |  |  |  |
| 1 vs. 0 | 0.5058 | −352.9 to 353.9 | No | ns | >0.9999 |
| 2 vs. 0 | 1.534 | −351.9 to 354.9 | No | ns | >0.9999 |
| 3 vs. 0 | 2.061 | −351.4 to 355.5 | No | ns | >0.9999 |
| 4 vs. 0 | 2.881 | −350.5 to 356.3 | No | ns | >0.9999 |
| 5 vs. 0 | 3.41 | −350.0 to 356.8 | No | ns | >0.9999 |
| 6 vs. 0 | 2.614 | −350.8 to 356.0 | No | ns | >0.9999 |
| 7 vs. 0 | 3.177 | −350.2 to 356.6 | No | ns | >0.9999 |
| 8 vs. 0 | 3.376 | −350.0 to 356.8 | No | ns | >0.9999 |
| 9 vs. 0 | 4.785 | −348.6 to 358.2 | No | ns | >0.9999 |
| 10 vs. 0 | 4.89 | −348.5 to 358.3 | No | ns | >0.9999 |

Indeed, researchers using theophylline have observed the need for screening their genes against putative aptamer sequences [Lentini, R. et al., Nat. Commun. 5, 4012 (2014)], to avoid naturally-occurring aptamers interacting with theophylline enough to interfere with translation and produce truncated proteins. Arabinose avoided this problem entirely; furthermore, the PBAD promoter is used in a great variety of commercially available bacterial expression vectors, many of which could be directly utilized in SMCs. Thus, arabinose was demonstrated to be a permeable activator that can be used in liposomal genetically cascaded circuits.

Figure 8A:
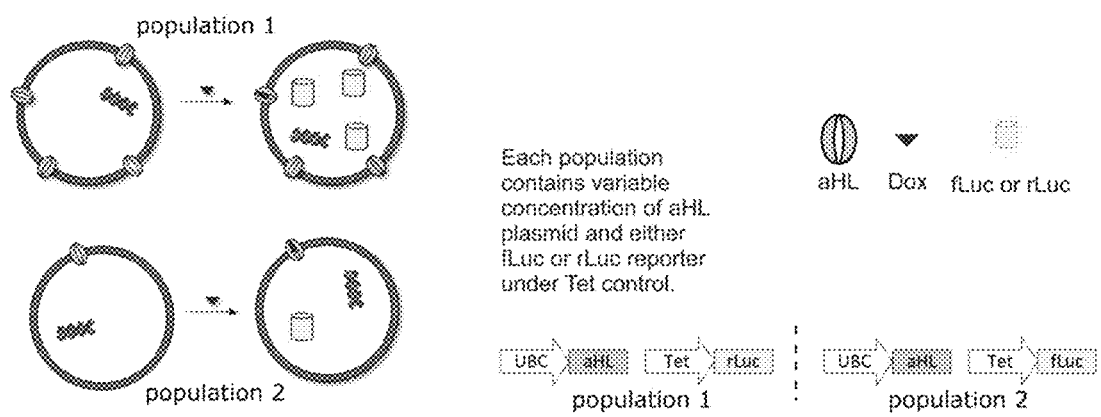
FIG. 8A-E provides schematic diagrams and graphs demonstrating multiple liposome populations operating in parallel without cross-talk.
Figure 8B:
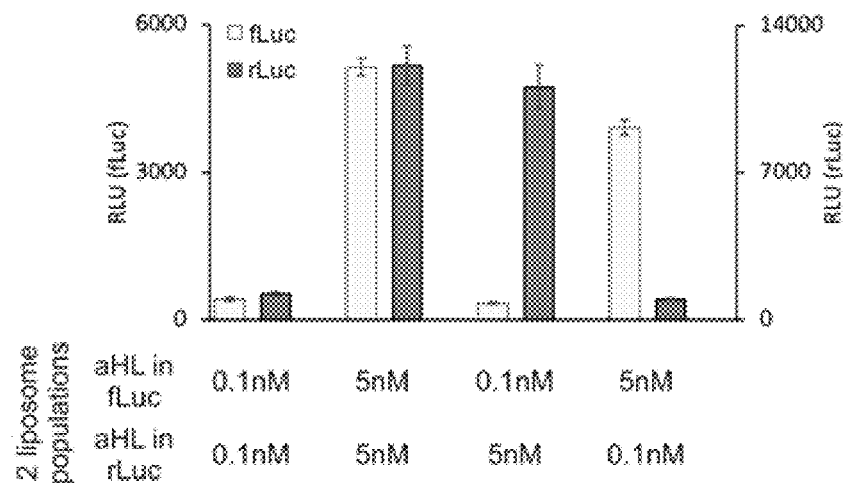
Figure 8C:
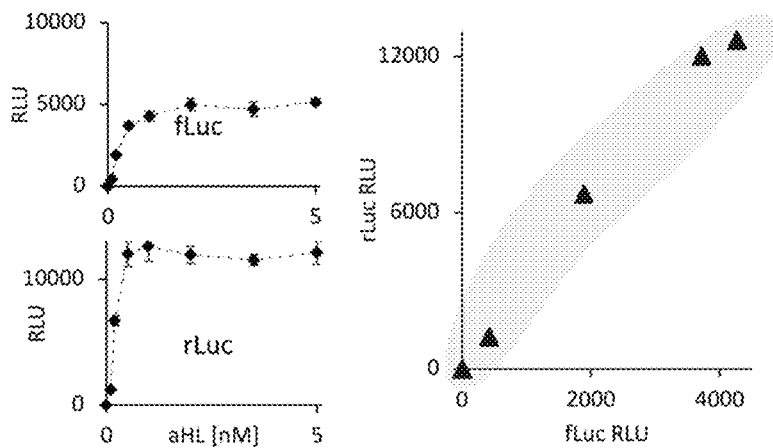
Figure 8D:
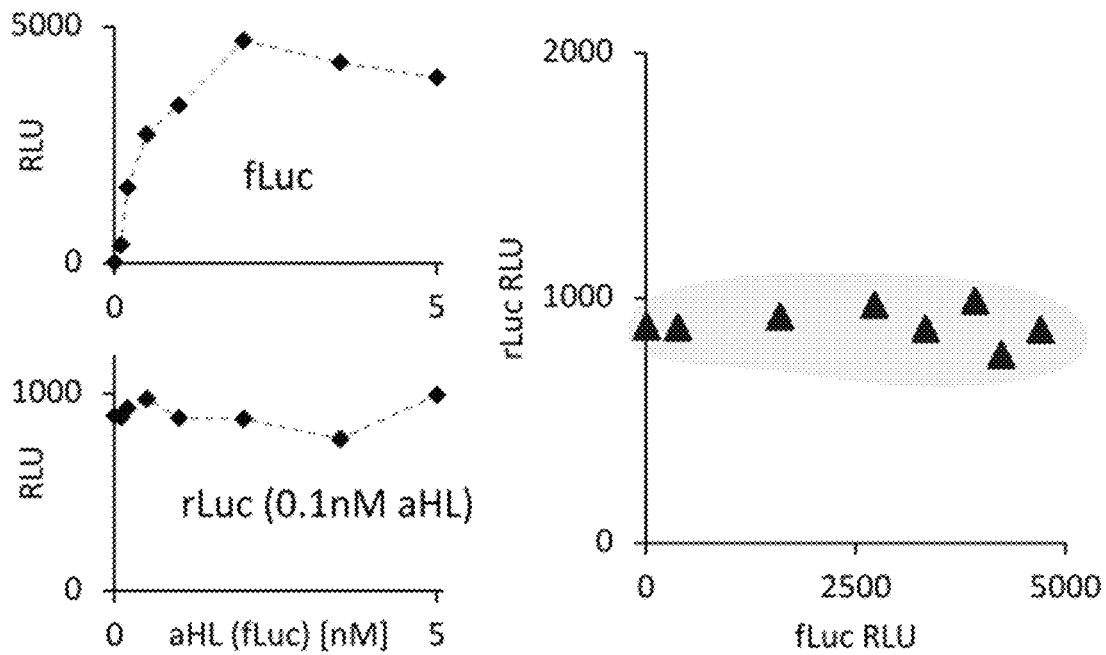
Figure 8E:
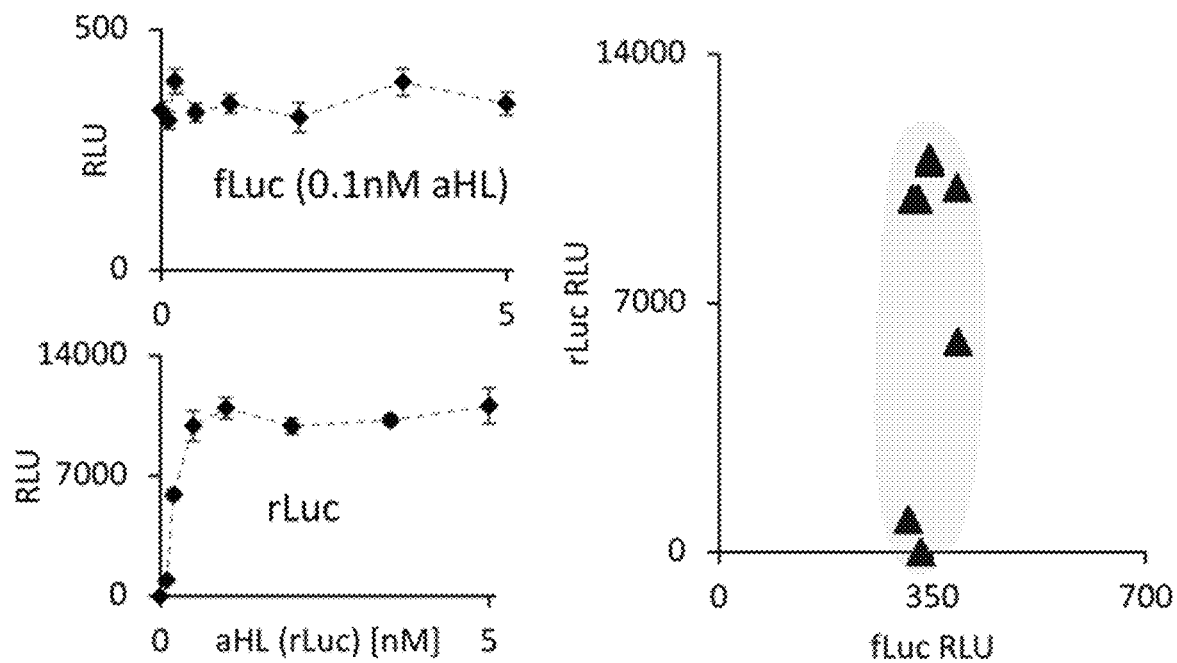

Two populations of liposomes carrying mammalian TX/TL extract and the same amount of Dox-inducible luciferase DNA (either Renilla or Firefly luciferase) were built, but the amount of alpha-hemolysin DNA was varied to result in high-aHL and low-aHL SMC populations (FIG. 8A). High-aHL and low-aHL SMCs responded to the membrane-impermeable Dox in the external solution, doing so proportionally to their own aHL concentration (FIG. 8B). No evidence was found that doxycycline acting upon one liposome population affected expression of luciferase in the other population: specifically, there was no significant difference in fLuc expression in high-aHL fLuc liposomes when the rLuc liposomes were high-aHL vs. low-aHL, and the same held for the other combinations (FIG. 8B; Sidak's multiple comparisons test after ANOVA with factors of luciferase type and alpha-hemolysin combination; see Table 10 for full statistics). That is, luciferase expression from each liposome population depended only on the amount of aHL DNA present in that population, and not on that of the other population (FIGS. 8C-8E).

Table 10

TABLE 10A

Statistics for FIG. 8B: 2-way ANOVA with factors of "Firefly or Renilla" and "alpha-Hemolysin Combination".

| Source of Variation | % of total variation | P value | P value summary | Significant? |
|---|---|---|---|---|
| Interaction | 34.06 | <0.0001 | **** | Yes |
| alpha-Hemolysin Combination | 43.87 | <0.0001 | **** | Yes |
| Firefly or Renilla | 18.41 | <0.0001 | **** | Yes |

TABLE 10B

Sidak's multiple comparisons test after the ANOVA. The four combinations of alpha-hemolysin (aHL) compared in this table correspond to the four clusters (of two bars each) in FIG. 8B. The concentrations of aHL DNA used to construct each liposome population are as follows:

| aHL combination | aHL in Firefly Luciferase liposomes | aHL in Renilla Luciferase liposomes |
|---|---|---|
| A | 0.1 nM | 0.1 nM |
| B | 5 nM | 5 nM |
| C | 0.1 nM | 5 nM |
| D | 5 nM | 0.1 nM |

|  | Mean Diff. | 95% CI of diff. | Significant? | Summary | Adjusted P Value |
|---|---|---|---|---|---|
| Firefly luciferase expression |  |  |  |  |  |
| B vs. A | 4730 | 2699 to 6761 | Yes | **** | <0.0001 |
| C vs. A | −80.77 | −2112 to 1951 | No | Ns | >0.9999 |
| D vs. A | 3498 | 1466 to 5529 | Yes | *** | 0.0003 |
| C vs. B | −4811 | −6842 to −2780 | Yes | **** | <0.0001 |
| D vs. B | −1233 | −3264 to 798.7 | No | Ns | 0.45 |
| D vs. C | 3578 | 1547 to 5610 | Yes | *** | 0.0002 |
| Renilla luciferase expression |  |  |  |  |  |
| B vs. A | 10890 | 8859 to 12921 | Yes | **** | <0.0001 |
| C vs. A | 9855 | 7824 to 11886 | Yes | **** | <0.0001 |
| D vs. A | −246.6 | −2278 to 1785 | No | Ns | 0.9996 |
| C vs. B | −1035 | −3066 to 996.4 | No | Ns | 0.6416 |
| D vs. B | −11137 | −13168 to −9105 | Yes | **** | <0.0001 |
| D vs. C | −10102 | −12133 to −8070 | Yes | **** | <0.0001 |

This experiment thus not only verified the independent operation of multiple non-interacting liposomes, but also verified that multiple liposome populations can be programmed in advance to have varying response levels to a given trigger, and then to be triggered and operate simultaneously but independently in the same external solution.

Figure 9A:
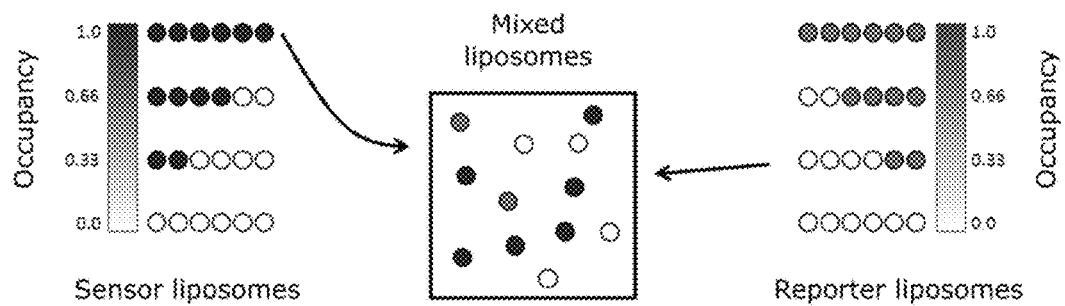
FIG. 9A-F shows schematic diagrams and graphs of results from multiple liposome populations operating in parallel with controlled communication between them.
Figure 9B:
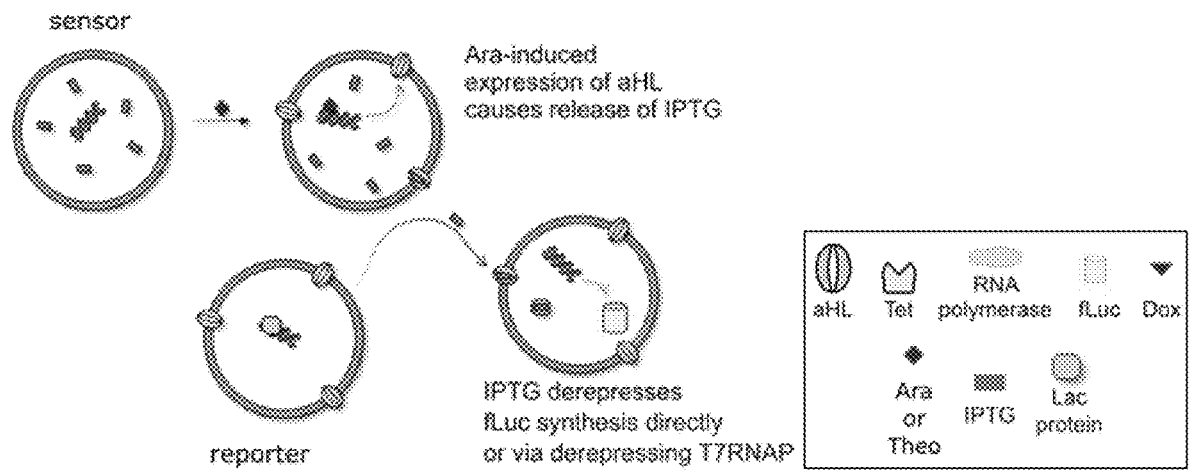
Figure 9C:
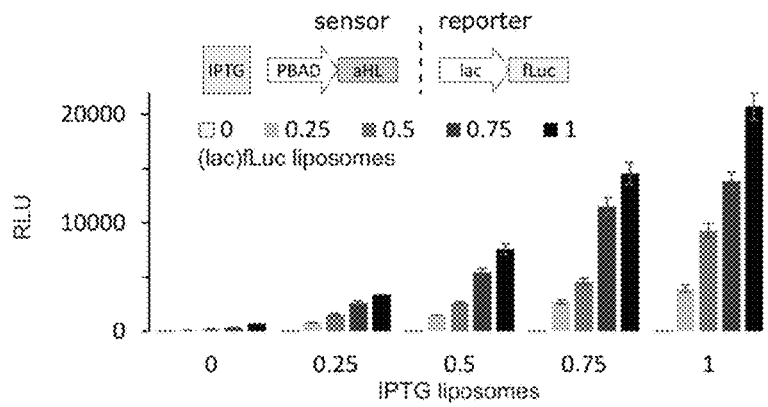
Figure 9D:
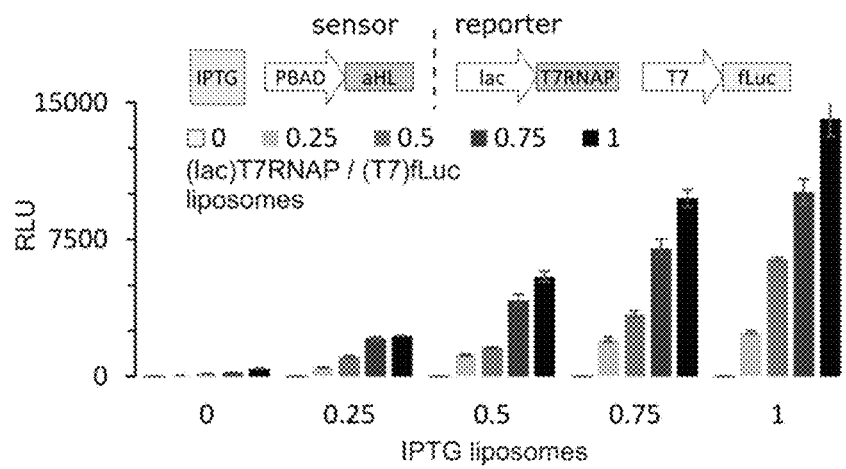
Figure 9E:
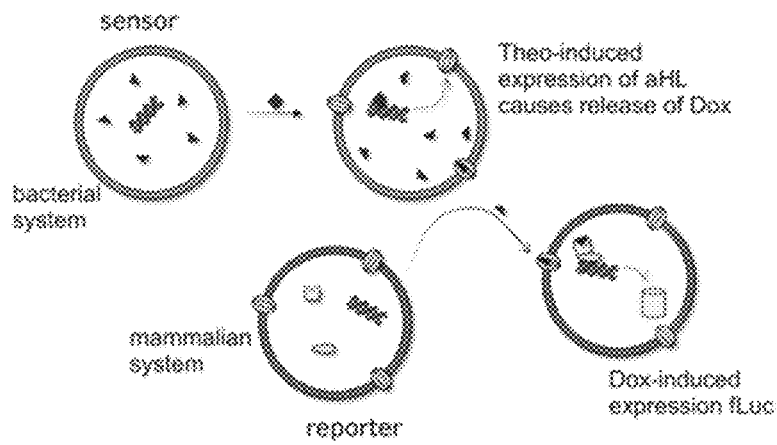
Figure 9F:
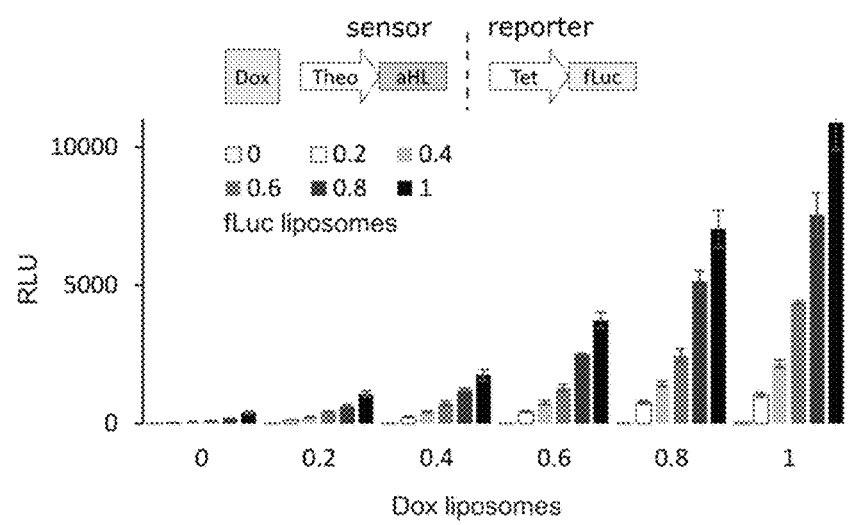

Two-component serial circuits were built by mixing together two populations of liposomes, a "sensor" that senses an external small molecule cue and a "reporter" that receives a message from the sensor population and produces an output; the occupancy of each population was varied to achieve a different overall ratio of the two components (FIG. 9A). The first version was built with bacterial TX/TL extract (FIG. 9B). The sensor liposomes contained IPTG (a small, non-membrane-permeable activator that induces the Lac promoter) and the arabinose-inducible gene for aHL; these liposomes thus sensed arabinose and released IPTG by expressing aHL channels. These were combined with reporter liposomes containing constitutively-expressed aHL, in which fLuc was under the control of the Lac promoter— either directly (fLuc under Lac promoter) or indirectly (T7RNAP under the Lac promoter and fLuc under T7 promoter)—and it was found that multi-component compartmentalized genetic circuits thus constructed were able to operate as coherent wholes (FIGS. 9C and 9D). Both systems were tested with multiple dilutions of sensor and reporter liposomes, and similar dose-response curves from titration of either species of liposome were observed (FIGS. 9C and 9D). Using this modular architecture, a genetic circuit was constructed that combines both bacterial and mammalian components (FIG. 9E). The sensor liposome in this case responded to theophylline and released doxycycline. Dox, in turn, activated fLuc expression in reporter liposomes built with mammalian components. As before, it was demonstrated that the multi-compartment genetic cascade could function as designed, with fLuc expression dose-response curves similar upon titrating either sensor or reporter liposome concentration (FIG. 9F). Thus, multi-component genetic circuits with radically different chemical micro-environments (e.g., made from bacterial vs. mammalian cell extracts) can be assembled into coherent networks.

Figure 10A:
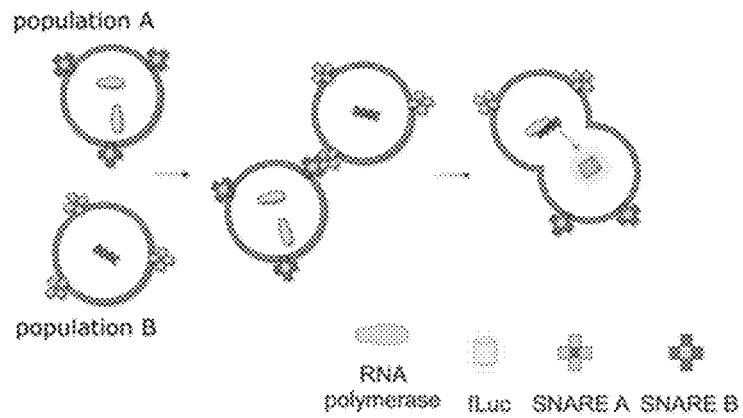
FIG. 10A-E provides schematic diagrams and graphs illustrating selective fusion of liposomes containing complementary genetic cascades.
Figure 10B:
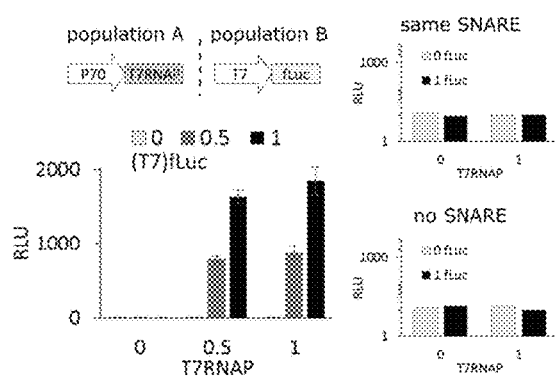
Figure 10C:
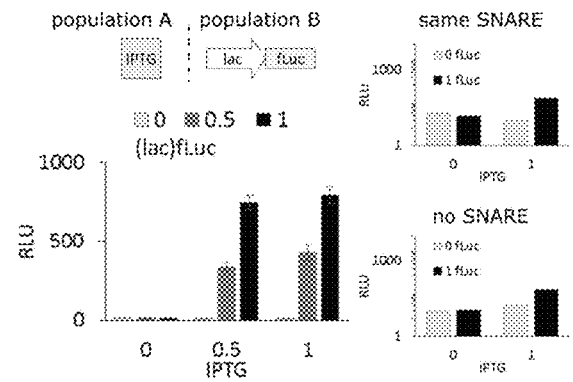
Figure 10D:
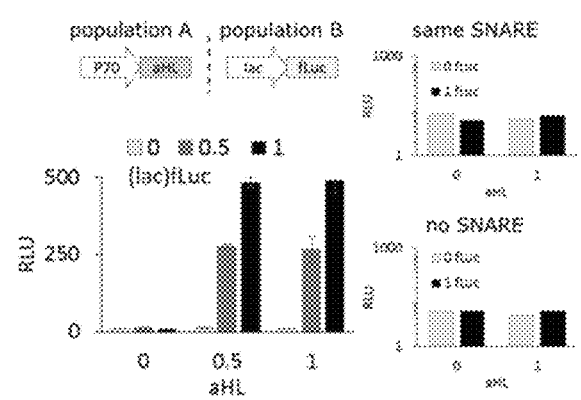
Figure 10E:
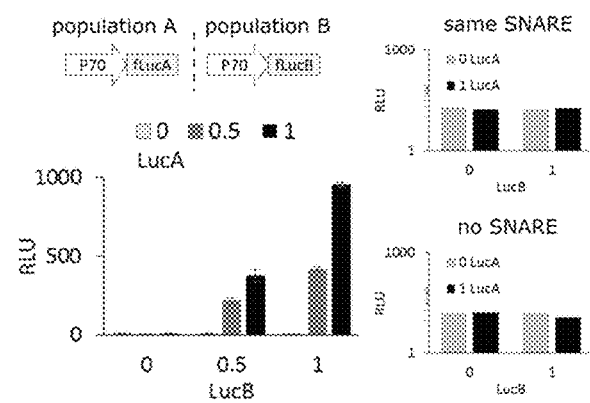

In another study, liposomes were programmed to be fused together (FIG. 10A). Liposome fusion was implemented using SNARE/coiled-coil hybrid proteins, which can be generated in complementary pairs that are specific in their fusion properties [Meyenberg, K. et al., Chem. Commun. 47, 9405 (2011) and Robson Marsden, H. et al., Biomater. Sci. 1, 1046 (2013)]. Then, by packaging into separate populations of SNARE-fusable liposomes, complementary circuit elements could be fused together: the gene for T7RNAP and a T7-driven fLuc (FIG. 10B); a non-membrane permeant small molecule trigger (IPTG) and an IPTG-triggered (lac-promoter driven) fLuc (FIG. 10C); genes for a membrane pore (aHL) and a lac-promoter driven fLuc (FIG. 10D, in an IPTG-containing ambient); or two different genes encoding for parts of split luciferase (FIG. 10E, using the same fLucA and fLucB as in FIG. 3B). In all cases, production of the final output of the genetic cascade was observed only when the two liposome populations were equipped with SNAREs, and only when they were a SNARE cognate pair (P<0.0001 for factor of SNARE compatibility, ANOVA with factors of mechanism, occupancy, and SNARE compatibility; see Table 11 for full statistics). By titrating the fraction of occupied liposome within each population independently (as in FIG. 9A), it is possible to tune the overall production of the final output, as well as the degree of modulation by environment. Liposomes undergoing SNARE-mediated fusion will form large aggregates made from multiple starter liposomes; this does not affect the results in FIG. 10, but might reduce the molecular crowding effects observed in FIG. 3.

TABLE 11

Statistics for FIG. 10: 3-way ANOVA with factors of Mechanism", "Occupancy", and "SNARE compatibility" (i.e., whether the SNARE protein mimics are complementary, equal, or not present).

| Source | Nparm | DF | Sum of Squares | F Ratio | Prob > F |
|---|---|---|---|---|---|
| Mechanism | 3 | 3 | 3636024.4 | 8.1956 | <.0001 |
| Occupancy | 2 | 2 | 7325476.5 | 24.7675 | <.0001 |
| SNARE compatibility | 2 | 2 | 5040146 | 17.0407 | <.0001 |

Expression of Enzymatic Reporter Proteins in Synthetic Minimal Cells

Experimental procedures included a focus on enzymatic reporters to measure protein expression because such reporters can be quantitatively detected at very low concentrations, and with linear ranges that extend over several orders of magnitude [Naylor, L. H., (1999) Biochem. Pharmacol. 58, 749-757; Hakkila, K., et al., (2002) Anal. Biochem. 301, 235-242; and Choy, g. et al. (200) Biotechniques 35, 1022-1030]. Firefly luciferase (fLuc), Renilla luciferase (rLuc), NANOLUC® luciferase (see Hall, M. P. et al., (2012) ACS Chem. Biol. 7, 1848-1857), beta lactamase, beta galactosidase, and chloramphenicol acyltransferase were each expressed in liposomes of the invention, using the constitutively active P70 bacterial promoter (see FIG. 25). The enzymatic activity of the reporters was assayed as a proxy for protein concentration, using multiple batch reactions run in parallel and collected at different time points. All five enzymatic reporters expressed well in synthetic minimal cells.

The full list of all tested enzymatic reporter proteins, corresponding small molecule substrates, and expression profiles in cell-free bacterial system under T7 promoter is shown in FIG. 25. In addition to the luciferase activity luminescence assays, the identity of expressed firefly luciferase protein was confirmed using Western Blot analysis, FIG. 28.

Optimization of Sequences for the Theophylline Riboswitch

It has been previously noted that putative ribosome binding sites inside the gene of interest might bypass the theophylline aptamer, resulting in expression of truncated genes independently of the theophylline riboswitch activity [see Lentini, R. et al., (2014) Nat. Commun. 5, 4012]. The sequence of [P70][Theo][T7RNAP] was screened for putative RBSs, using the sequence composition and spacing rules elucidated by Lentini, R. et al., (2013) ACS Synthetic Biology 2(9), 482-9. The [T7][fLuc] reporter was used to validate that T7RNAP expression was indeed under the control of the theophylline riboswitch (see FIG. 7B). The amount of "leakage" seen was comparable to previously reported levels in Lentini, R. et al, (2014) Nat. Commun. 5, 4012.

Encapsulation Efficiency and Size Distribution

The efficiency of solute encapsulation inside POPC liposomes of a given radius r (nm) at a given concentration c (mM) can be estimated using the formula below, which has been empirically confirmed by encapsulation experiments:

$$\% \text{ internal volume} = \text{vol\_liposome} * \text{liposomes\_ml} * 10^{-19}$$

Where:

$\text{vol\_liposome} = (4/3)*PI*(r^3)$ is the volume of the lumen of a single liposome, in $nm^3$;

$\text{liposomes\_ml} = \text{surface\_area\_ml}/\text{area\_liposome}$ is the number of liposomes per 1 mL;

$$\text{surface\_area\_ml} = (c*10^{-6})*((760*10^{21})/0.9*N_A)/2.5)/2$$

is the surface area of liposomes per 1 mL of solution of a given c (nM), with POPC MW=760 and length of the lipid bilayer approximated to 2.5 nm; $N_A$ is Avogadro's number; and $\text{area\_liposome} = 4*PI*(r^2)$ is the surface area of the liposome outer leaflet, in $nm^2$.

These calculations were made with the assumption that liposome is negligible, so the inner and outer leaflet contain an equal number of lipids and have equal surface area. The thickness of the bilayer was approximated at 2.5 nm [see: Lewis, B. & Engelman, D. M. (1983) J. Mol. Boil 166, 211-217]. The addition of cholesterol increases bilayer thickness up to 30%, thus affecting the encapsulation rate [see Nezil, F. A. & Bloom, M. (1992) Biophys. J. 61, 1176-1183], but it was not possible to reliably estimate the influence of cholesterol on packing density and surface area of the liposomes.

According to this formula, a 25 mM solution of 200 nm POPC liposomes will contain ~14% of the total volume encapsulated inside liposomes. In reality, the encapsulation rate of liposomes used in the experiments was likely somewhat lower. This was due to factors like the presence of cholesterol in POPC membranes, and the fact that in liposomes extruded through a 200 nm filter the size distribution of liposomes varies greatly and is, on average, smaller than 200 nm [see Jousma, H. et al., (1987) Int. J. Pharm. 35, 263-274; Olson, F., et al., (1979) Biochim Biophys. Acta 557, 9-23; and Berger, N. et al., (2001) Int. J. Pharm. 223, 55-68]. The differences in yield of protein synthesis inside synthetic cells, explained by the difference in efficiency of encapsulating the TX/TL enzyme mix, have been previously observed.

Figure 26:
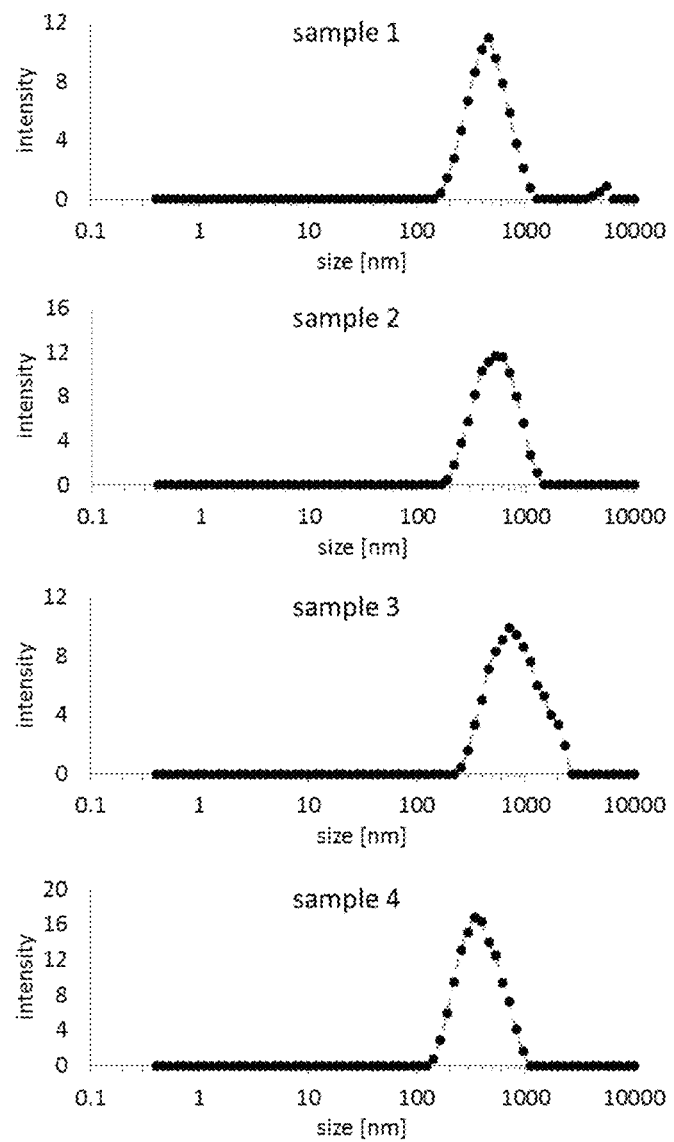
FIG. 26 provides graphs showing dynamic light scattering analysis of liposomes. Samples from separate encapsulation, extrusion and dialysis processes, prepared on different days were compared. The measurements were performed using a Malvern Zetasizer Nano instrument, and data was analyzed using Zetasizer Ver. 7.04. All measurements were performed at 25° C., at measurement angle 173° backscatter.

Dynamic light scattering (DLS) was used to analyze samples of liposomes prepared according to the protocol used in this work (see Materials and Methods herein and FIG. 26). The liposome sample size distribution was consistent between different preparations (samples from separate encapsulation, extrusion and dialysis processes, prepared on different days, are compared). The DLS experiments are very sensitive to fluorescent dyes present in the solution; therefore, thus those experiments were performed on samples not producing any fluorescent reporter protein. As used in equations set forth herein "^" preceding a number means the number is superscripted, and "*" means "multiplied by".

Efficiency of Small Molecule Activator Transfer

Figure 5A:
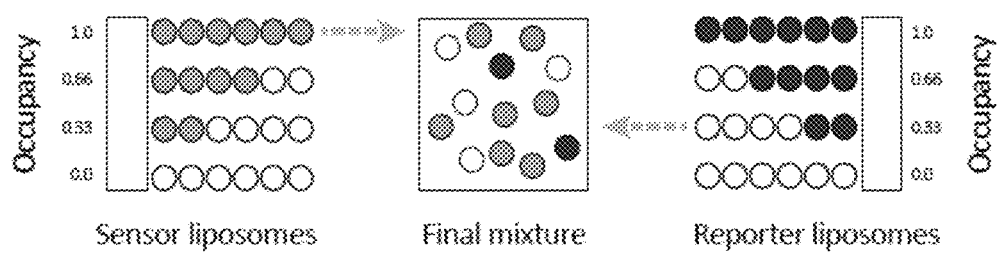
FIG. 5A-F provides schematic diagrams and graphs illustrating communication between genetic circuits operating in multiple liposome populations.

To assess the efficiency of IPTG activation between liposomes, estimations were made of the release of small molecules from liposomes through aHL channels. A sample of IPTG sensor liposomes was prepared as in experiments in FIG. 5C, but also containing 100 mM calcein—a fluorescent, non-membrane-permeable, small-molecule dye. Thus, the sensor liposomes contained both small molecules (IPTG and calcein) and the arabinose-inducible gene for aHL. These sensor liposomes were mixed 1:1 with reporter liposomes like those from FIG. 5C and the mixture was incubated with arabinose. After incubation, the luciferase activity from half the liposome mixture was measured and the other half of the liposome mixture was purified on a Sepharose 4B size exclusion column, measuring the total fluorescence of the collected unencapsulated fraction. The concentration of the unencapsulated calcein, calculated from the dye fluorescence, was 0.18 mM in the 2.1 ml of the free dye fraction collected from the purification column. This corresponds to a concentration of ~3.78 mM in the original 100 μL sample of mixed liposomes; this can serve as an estimate of the concentration of small molecules that easily and maximally permeate through the aHL pore (e.g., of IPTG). For reference, the initial concentration of IPTG and calcein in the liposome encapsulation mixture was 100 mM.

An additional validation of this estimate was performed for equilibrium IPTG concentration in the sensor-reporter mixture. A sample of reporter liposomes identical to those from FIG. 5C was prepared, and mixed with empty liposomes plus IPTG to the final concentration of 3.78 mM. From this mixture a final luciferase activity of 28868 RLU (average of 3 samples, S. E. M. 815 RLU) was recorded, which is comparable to the 20820 RLU recorded for the 1:1 mix of sensor and reporter liposomes in FIG. 5C.

Figure 38A:
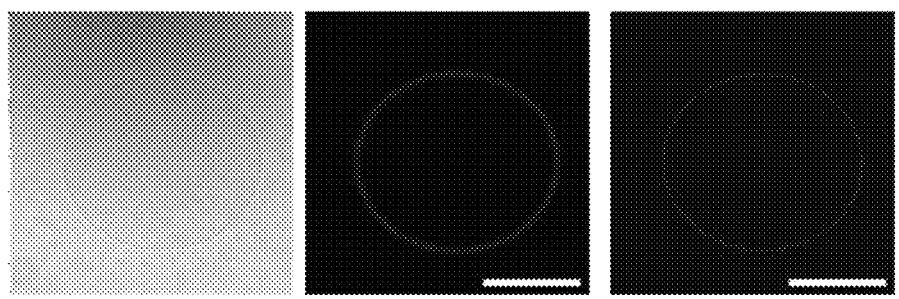
FIG. 38A-B provides photomicrographic images and a graph illustrating incorporation of alpha hemolysin protein into phospholipid bilayer membrane.
Figure 38B:
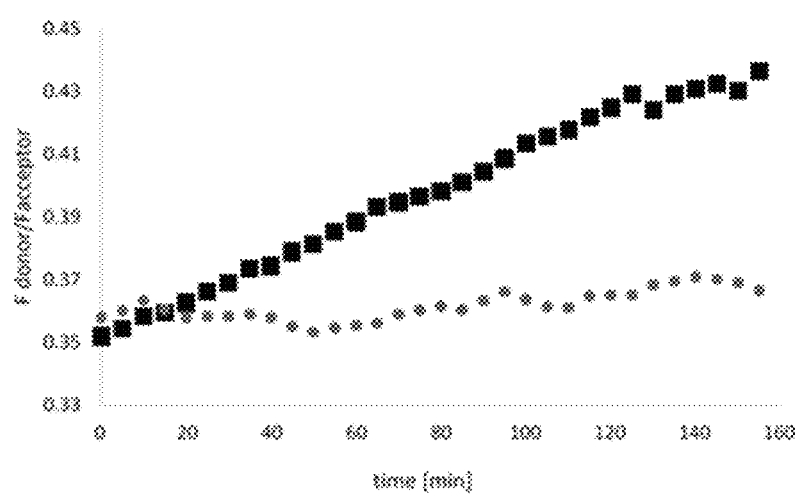

The insertion of the alpha hemolysin channel into the bilayer membrane of liposomes was also confirmed by two separate experiments. For the first experiment, the aHL was prepared as a fusion to the fluorescent protein mClover (see FIG. 38 description). The mClover-aHL fusion was expressed in large unilamellar vesicles prepared with LISSAMINE™ Rhodamine B (red fluorescent dye tethered to a phospholipid: 1,2-Dihexadecanoyl-sn-Glycero-3-Phosphoethanolamine, Triethylammonium Salt) in the phospholipid membrane. Direct confocal microscopy observation confirmed the co-localization of the green signal from the alpha hemolysin protein fusion with the red signal from the lipid-bound membrane dye (FIG. 38). For the second experiment, liposomes were prepared as described in the Materials and Methods section herein, with two membrane dyes capable of FRET (Fluorescence Resonance Energy Transfer): LISSAMINE™ Rhodamine B 1,2-Dihexadecanoyl-sn-Glycero-3-Phosphoethanolamine, Triethylammonium Salt and NBD-PE N-(7-Nitrobenz-2-Oxa-1,3-Diazol-4-yl)-1,2-Dihexadecanoyl-sn-Glycero-3-Phosphoethanolamine, Triethylammonium Salt. Alpha hemolysin protein was expressed inside liposomes, from a constitutive bacterial P70 promoter, using bacterial TX/TL extract. The decrease in the observed FRET signal (increase in donor fluorescence and decrease in receptor fluorescence) indicated changes in the surface area of the liposome. This technique has been previously used to see insertion of biomolecules into the bilayer membrane of liposomes [see Kamat, N. P. et al., (2015) Angew. Chemie—Int. Ed. 54, 11735-11739]. The observed increase of the membrane surface area is attributed to the insertion of the membrane protein into the bilayer. The negative control experiment, expressing firefly luciferase—a soluble protein with no known association to phospholipid membranes, results in no change of FRET signal over time.

Cascaded Circuits

Cascaded circuits, in which the product of one gene triggers the production of the next, are useful for a variety of reasons for signal amplification (i.e., a relatively small input signal can trigger a high output), for modularity (e.g., a variety of sensors can be connected to a given output), and to enable multi-node control at various points within the network (as in the configuration of natural signaling and metabolic pathways in cells, where many reagents must be regulated in timing and concentration, for efficient synthesis). Such cascaded circuits are widely employed in synthetic circuits for these reasons [see McAdams, H. H. & Arkin, A. (1998) Annu. Rev. Biophys. Biomol. Struct. 27, 199-224 and Purnick, P. E. M., & Weiss, R. (2009) Nat. Rev. Mol., Cell Biol. 10, 410-422]. Cascaded circuits were built in this experiment using liposomes with *E. coli* TX/TL extract. The circuit that was constructed had the gene for fLuc (in single component form) under a T7 promoter (recognized by T7 RNA Polymerase, T7RNAP), with the gene for T7RNAP itself under the control of a membrane-permeable activator (FIG. 7A), here. either theophylline (Theo, which activates an aptamer sequence in the 5'-UTR that un-masks a ribosome binding site and triggers protein production) or arabinose (Ara, which induces the PBAD promoter). These activators had been previously tested in phospholipid liposomes for the induction of single genes [see Lentini, R. et al., (2014) Nat. Commun. 5, 4012 and Shin, J. & Noireaux, V. (2012) ACS Synth. Biol. 1, 29-41].

The theophylline system was found to be leaky, as previously observed, (expression for all time points after t=3 h was significantly different from that at t=0, P<0.0001 in Sidak's multiple comparison test, after ANOVA with factors of time and presence or absence of theophylline; FIGS. 7B and 7C; see Table 8 for full statistics). No measurable activation of PBAD was found in the absence of arabinose, suggesting that arabinose may be a useful external trigger for cascaded genetic circuits (expression for all time points was equal to that for t=0, P>0.9999 in Sidak's multiple comparison test, after ANOVA with factors of time and presence or absence of arabinose; FIGS. 7D and 7E; see Table 9 for full statistics). Additionally, researchers using theophylline have observed the need for screening their genes against putative aptamer sequences, to avoid naturally-occurring aptamers interacting with theophylline enough to interfere with translation and produce truncated proteins. Arabinose avoided this problem entirely; furthermore, the PBAD promoter is used in a great variety of commercially available bacterial expression vectors, many of which can be directly utilized in synells, for example using methods described herein. Thus, the studies demonstrated the use of arabinose as a permeable activator for liposomal genetically cascaded circuits.

Direct Comparison of Bacterial and Mammalian Systems

Figure 29:
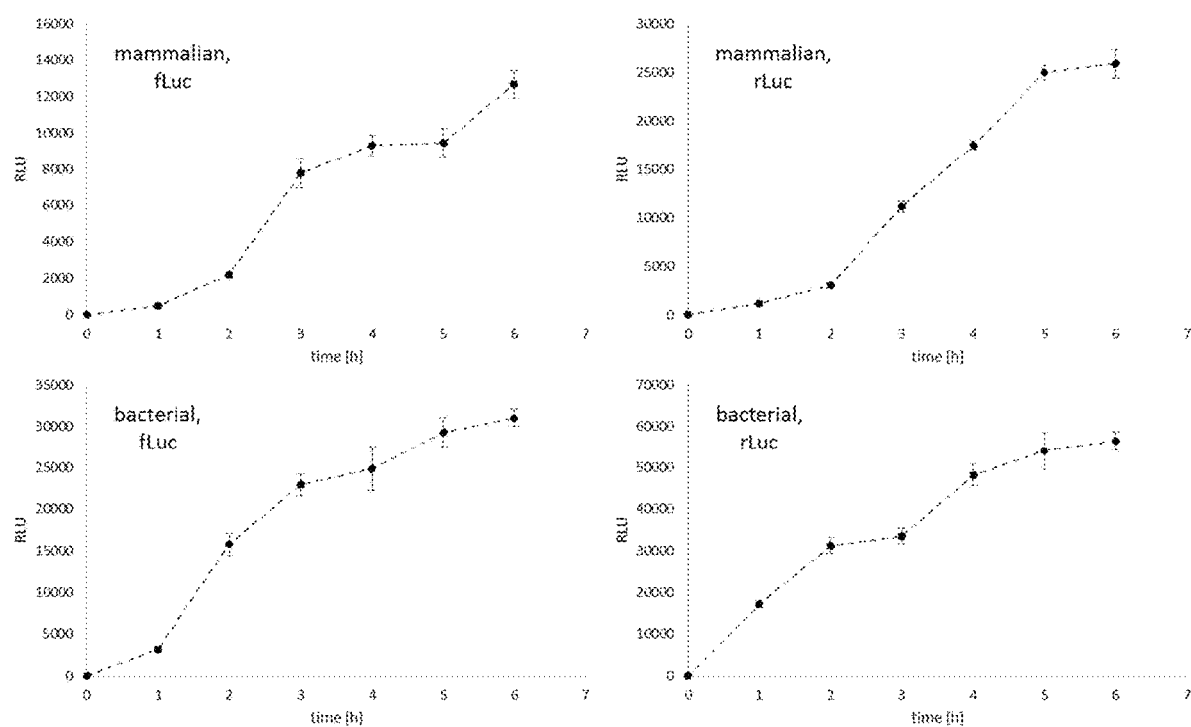
FIG. 29 provides graphs showing comparison of bacterial and mammalian TX/TL, for firefly and Renilla luciferases (fLuc and rLuc). Dotted lines are visual guides, not data fits. Error bars indicate S.E.M, n=4.

Synells containing mammalian and bacterial TX/TL, both systems expressing firefly luciferase, were compared side-by-side. The mammalian system was slower to reach maximum protein yield, and the total product yield was significantly lower, for the same volume and the same initial plasmid concentration (FIG. 29).

Typically, eukaryotic systems offer better folding and access to post-translational modifications, at the price of significantly lower yields. Prokaryotic systems generally allow for higher yields at lower cost. If multi-domain proteins, complex signaling cascades, or large proteins are needed, eukaryotic systems generally should be used. Folding of large fusion proteins may be much more efficient in eukaryotic systems. Also, eukaryotic systems typically offer a much wider range of post-translational modifications than prokaryotic extracts. Bacterial extract, most commonly prepared form *E. coli*, is robust to changes in reaction temperature and tolerant to chemical additives while offering high yield of simple, unmodified proteins. Additionally, the bacterial TX/TL extract is relatively easy and cheap to prepare [see for example: Sun Z. Z. et al., (2013) J. Vis. Exp. 1-15 and Caschera, F. & Noireauz, V. (2015) Metab. Eng. 27 29-37].

Mammalian cell-free TX/TL systems have been developed to synthesize long, complex proteins that require folding chaperones and post-translational modifications [Brödel, A. K. & Kubick, S. (2014) Pharm. Bioprocess. 2, 339-348]. Commercially available rabbit reticulocyte systems offer cap-independent translation and contain mammalian folding chaperones. The glycosylation of proteins is possible in this system upon addition of canine pancreatic microsomal membranes; this typically decreases the overall yield of protein synthesis. Human HeLa cell extract is also commercially available; it is used to express antibodies, as well as large and complex proteins and viruses [see Machida, K. et al., (2012) Protein Synthesis in vitro: Cell-Free Systems Derived from Human Cells, Cell-Free Protein Synthesis, Prof. Manish Biyani (Ed.), InTech, DOI: 10.5772/48563. Available from: www.intechopen.com/books/cell-free-protein-synthesis/protein-synthesis-in-vitro-cell-free-systems-derived-from-human-cells and Mikami, S. et al., (2008) Protein Expr. Purif. 62, 190-198].

In summary, here is a brief general comparison of bacterial and mammalian systems (information based on various sources; note that these are generalities, and these rules of thumb may not always hold in all conditions):

TABLE 12

Comparison of Bacterial and Mammalian Expression Systems

| | Bacterial | Mammalian |
|---|---|---|
| Protein yield | High yields | Low yields |
| Post-translational modifications | Very limited | Glycosylation possible, other modifications also possible |
| Cost of use | Low | High |
| Ease of use (tolerance to additives, temperature, etc.) | High: tolerance to extreme temperatures and small molecule additives | Low: narrower set of temperatures, sensitive to changes in conditions and composition of reaction mixture |

Confinement of Genetic Circuits in Liposomes

Figure 27A:
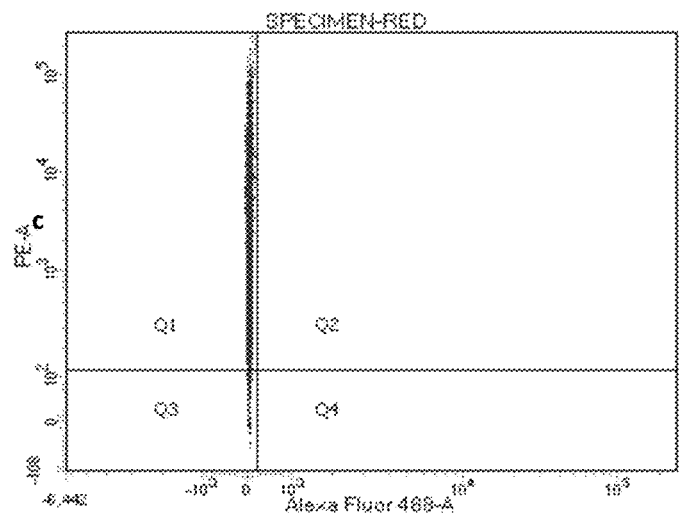
FIG. 27A-C shows results of control samples for flow cytometry of synthetic minimal cells (as in FIGS. 2C and 2D). All samples contained liposomes with cell-free TX/TL mixture and a plasmid for expressing GFP, encapsulated in liposomes labeled with rhodamine-bearing membrane dye (red) prepared as described in the Examples section, Materials and Methods, herein.
Figure 27B:
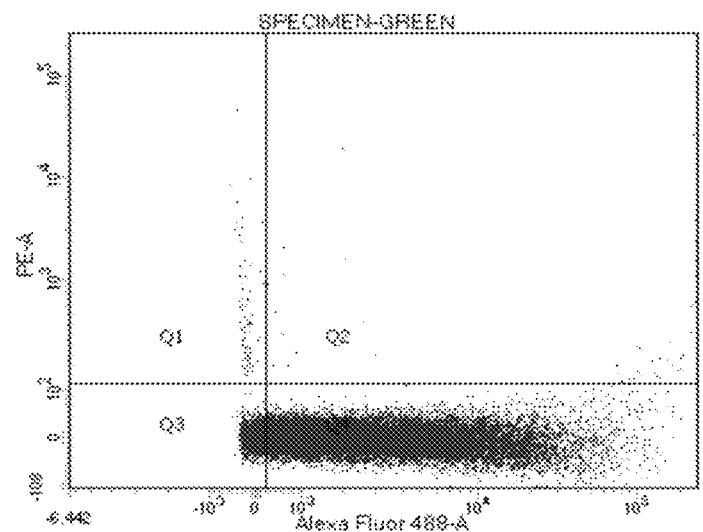
Figure 27C:
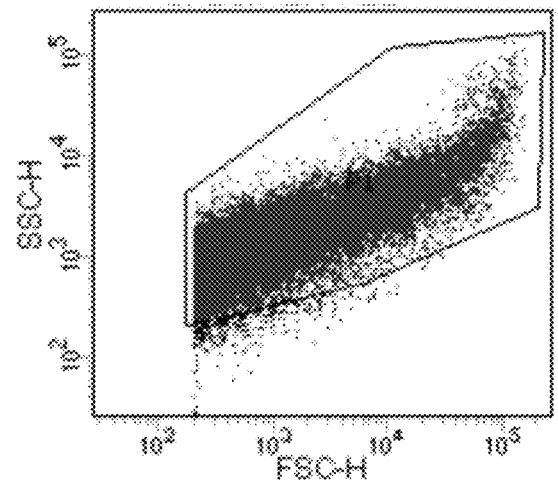
Figure 28:
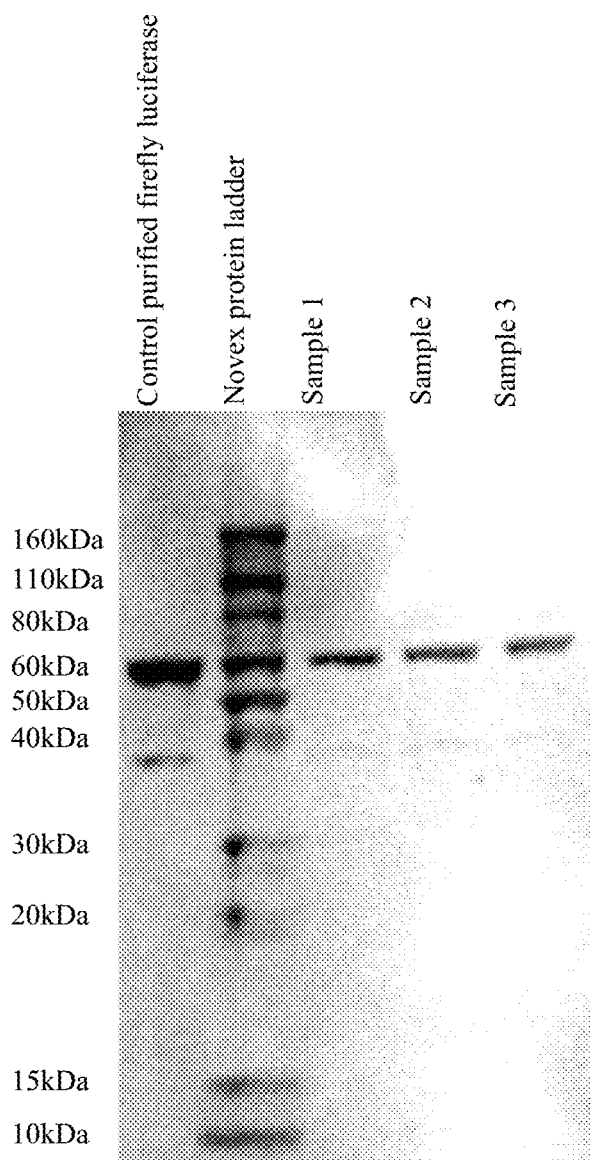
FIG. 28 is an image showing Western blot analysis of firefly luciferase expression. Protein chromatography was performed using Novex™ 14% Tris-Glycine Mini Protein Gels; primary antibody staining was performed with mouse monoclonal Anti-6×His tag antibodies (Abcam); and secondary staining was performed using WesternBreeze Chromogenic Kit, anti-mouse (Thermo Scientific). Sample 1: Firefly luciferase expression under T7 promoter in a bacterial TX/TL system. Sample 2: Firefly luciferase expression under the Tet promoter in a bacterial TX/TL system. Sample 3: Luciferase expression in a HeLa TX/TL system after transcription using HeLa nuclear extract. The sample used in this experiment is the same as in the 1:1 A:B ratio in FIG. 6F. Prior to loading of the gel, luciferase activity in aliquots of each sample was measured, and the obtained luminescence signal was used to approximately normalize the concentration (loading volume) of all samples. As a positive control, purified full-length recombinant firefly luciferase protein (Abcam) was used.

Before exploring the control of, and communication with, synells containing genetic cascades, studies were first performed to characterize the basic structural and functional properties of individual synells. To characterize the size and functionality of the prepared liposomes, liposome membranes were labeled with red dye (rhodamine functionalized with a lipid tail) and filled with cell-free transcription/translation (TX/TL) extract derived from HeLa cells [see: Weber, L. A., et al., (1975) Biochemistry 14, 5315-5321; Wimmer, E. (1991) Science 254,m 1647-51; Mikami, S et al., (2006) Protein Expr. Purif. 46, 348-57; and Mikami, S. et al., (2008) Protein Expr. Purif. 62, 190-198], as well as DNA encoding either GFP or split GFP. Structured illumination microscopy (SIM) images showed that GFP liposomes had a diameter between 100 nm and 1 μm (FIG. 2A), a measurement that was confirmed with dynamic light scattering (FIG. 26). Flow cytometry was used to quantify the functional expression of genes by synells; 68.4% of the GFP liposomes expressed fluorescence, along with 61.8% of those encapsulating split GFP (FIGS. 2B-2D; for control flow cytometry experiments, see FIG. 27). The enzymatic activity of several reporters was characterized in the prepared liposomes (FIG. 25) and a Western blot was used to provide an additional non-enzymatic characterization of luciferase expression (FIG. 28). The performance of mammalian (HeLa) and bacterial (*E. coli*) TX/TL systems in prepared liposomes was compared and the results indicated that the mammalian system to be slower and have a lower protein yield (FIG. 29).

Having established that the liposomes were of proper size and functionality, experiments were performed to verify that a well-known advantage of liposomal compartmentalization—facilitated reaction efficacy due to molecular confinement [since encapsulating reactants within a liposome facilitates their interaction due to the small volume; see Tan, C. et al. (2013) Nat. Nanotechnol. 8, 602-8; de Souza, T. P. et al. (2012) Orig. Life Evol. Biosph. 42, 421-428; de souza, T. P., et al., (2014) J. Mol. Evol. 79, 179-192; and Caschera, f. & Noireauz, V. (2014) Curr. Opin. Chem. Biol. 22, 85-91]—can help support multi-component genetic circuits as well as chemical reactions of higher order. Studies were carried out to compare cell-free transcription/translation (TX/TL) reactions that produce firefly luciferase (fLuc) from one, two, or three protein components, testing them in bulk solution vs. synells. In this experiment, HeLa cell extract constitutively expressing the Tet protein was used to mediate small-molecule induction of transcription of the one, two, or three fLuc components, as well as alpha-hemolysin (aHL), which serves as a pore to admit doxycycline (Dox) to trigger Tet function [see Noireaux, V. & Libchaber, A. (2004) Proc. Natl. Acad. Sci. U.S.A. 101, 17669-74; Stefureac, R. et al., (2006) Biochemistry 45, 9172-9179; and Gouaux, E., et al., (1997) Protein Sci. 6, 2631-2635]. The one-component luciferase was simply conventional monolithic fLuc (FIG. 3A); the two-component system (i.e., to explore 2nd-order reactions) comprised the two halves of split firefly luciferase, each attached to a coiled coil and a split intein fragment to bring the halves together and covalently bridge them (FIG. 3B) [see Selgrade, D. F., et al., (2013) J. Am. Chem Soc. 135(20):7713-9]; and the three-component system involved the halves of split firefly luciferase bearing coiled coils and split inteins, with the coiled coils targeting a third protein, a scaffold (FIG. 3C) [see Selgrade, D. F., et al., (2013) J. Am. Chem Soc. 135(20):7713-9].

Figures 11, 11A, 11C:
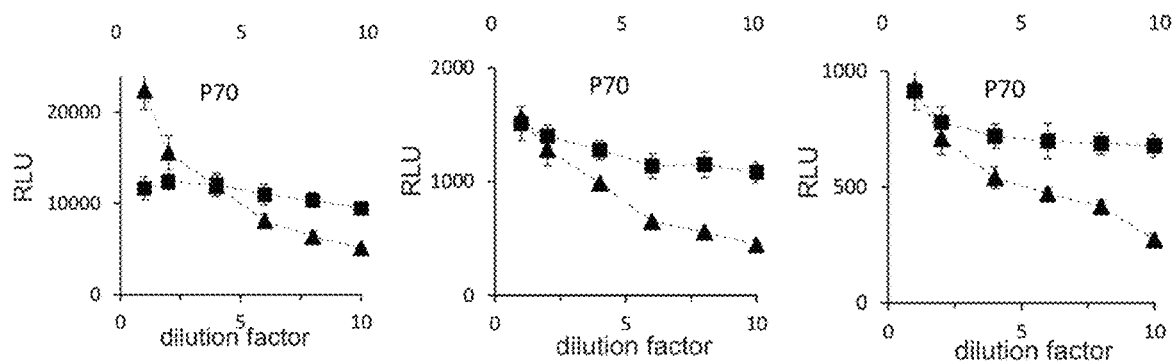
Figures 12A, 12B:
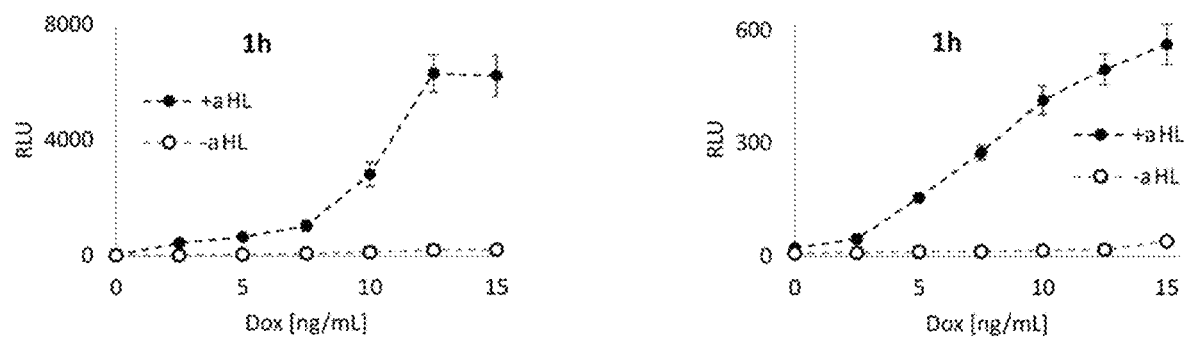
FIG. 12A-C provides graphs illustrating end-point expression of luciferase from each of the expression systems presented in FIG. 3, measured at end point 1 h, at 7 different concentrations of Dox. The dotted lines are visual guides, not fits.
Figure 12C:
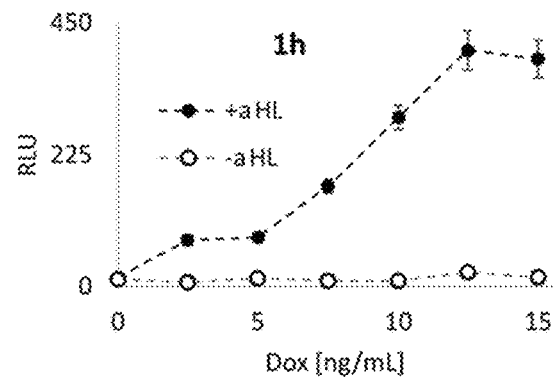
Figures 13A, 13B:
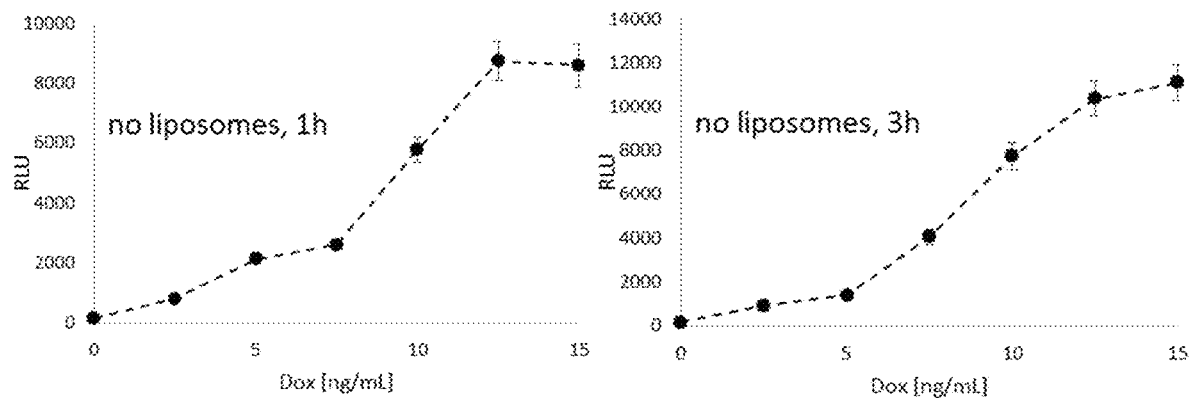
FIG. 13A-B provides graphs showing results of single-protein fLuc expression in solution, 5 nM plasmid.
Figures 14A, 14B:
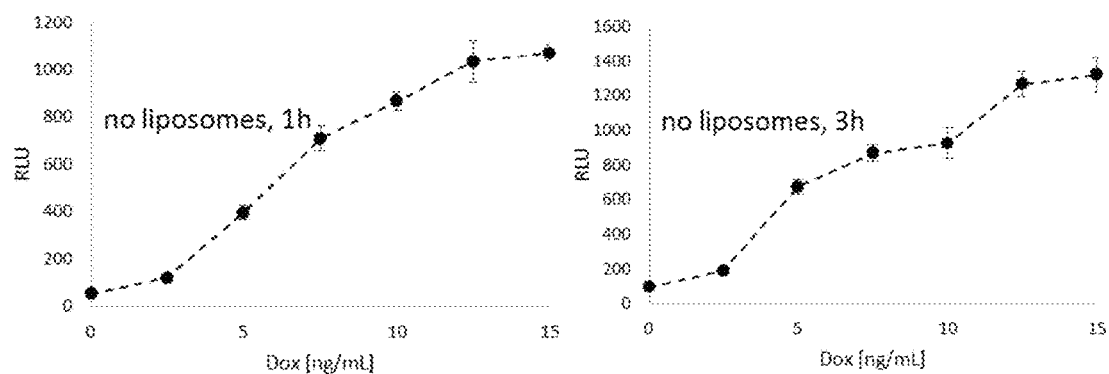
FIG. 14A-B provides graphs showing results of two-protein fLuc expression in solution, plasmids for fLucA and fLucB combined at 2.5 nM each.
Figures 15A, 15B:
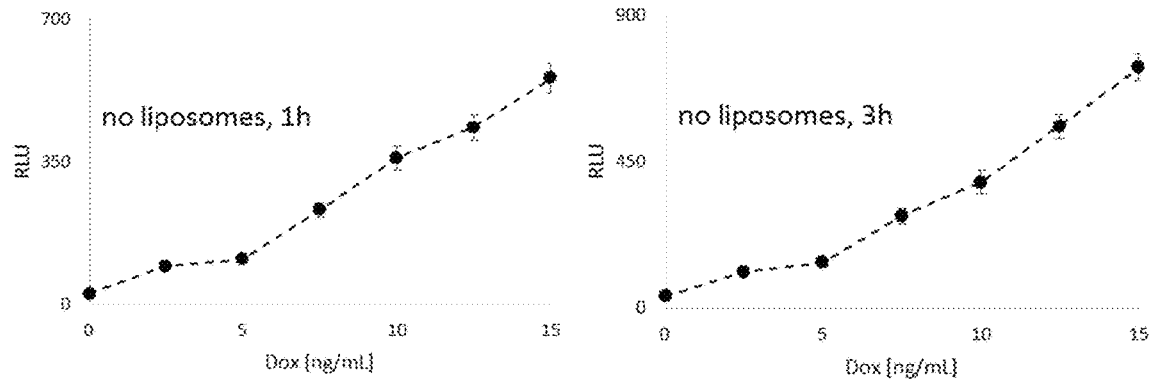
FIG. 15A-B provides graphs showing results of three-protein fLuc expression in solution; plasmids fLucC, fLucD, and Scaffold combined at 1.67 nM each.
Figure 18:
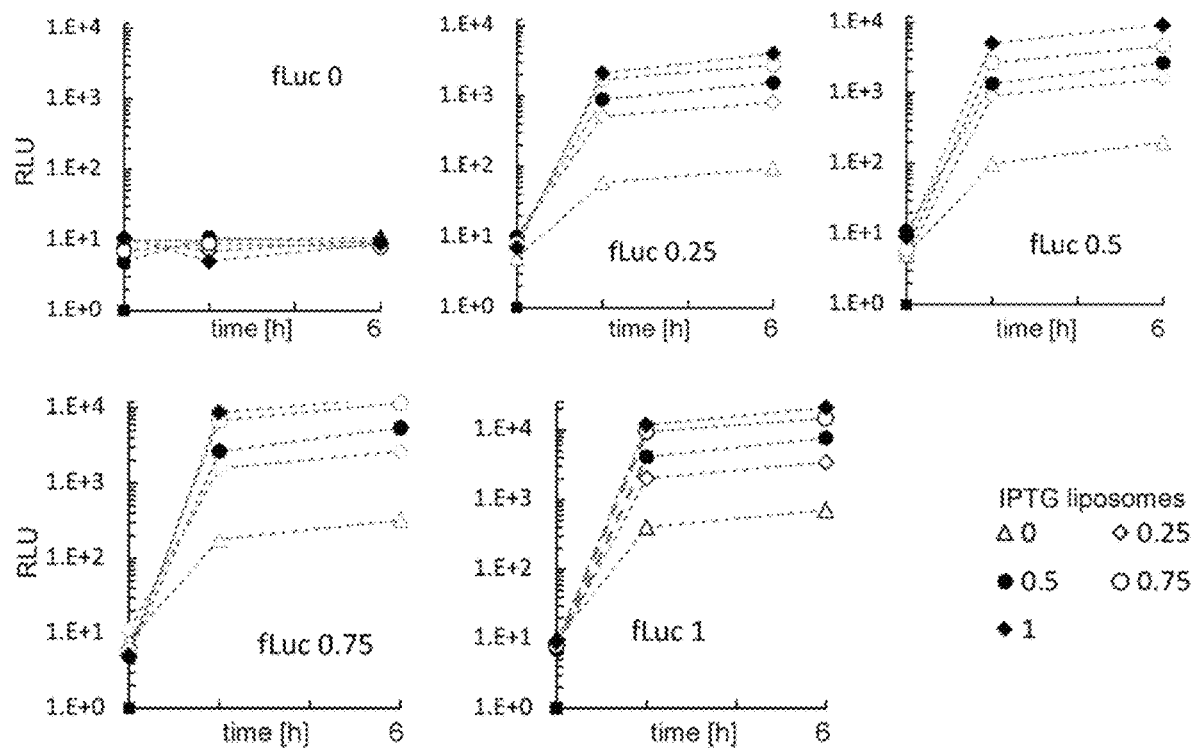
FIG. 18 provides graphs illustrating the time-course of expression of fLuc under lac promoter, with different ratios of liposomes. The Y-axis is relative light units (RLU) and the X-axis is time in hours.

For all three orders of luciferase-producing reactions, the effect of dilution on fLuc expression was weaker for liposomes than for bulk solution (FIGS. 3D-3F); $P<0.0001$ for interaction between factors of encapsulation and dilution factor; ANOVA with factors of encapsulation and dilution factor; see Tables 1-3 for full statistics and FIG. 11 for corresponding experiments under the control of a constitutive P70 promoter). As expected, fLuc expression was proportional to the concentration of Dox added to the external solution, and depended on aHL (FIG. 3G-3I show end-point expression after 3 h; see FIG. 12 for the corresponding expression at a 1 h end-point, and FIGS. 13-15 for the same reactions in bulk solution). Liposomes produced lower amounts of fLuc than the same volume of TX/TL extract in bulk solution—likely due to the well-known property of stochastic loading of reagents into liposomes [see: de Souza, T. P. et al. (2012) Orig. Life Evol. Biosph. 42, 421-428 and de Souza, T. P., et al., (2014) J. Mol. Evol. 79, 179-192] ($P<0.0001$ for factor of encapsulation in ANOVA with factors of time, encapsulation, and order; see Table 4 for full statistics). For the third-order reaction, it was found that liposome encapsulation resulted in efficacy nearly equal to that of bulk solution ($P=0.1324$ for factor of encapsulation in ANOVA with factors of time and encapsulation; FIG. 3L; see Table 7 for full statistics), whereas for the first-order and second-order reactions the liposomes resulted in lower efficacy ($P<0.0001$ for factor of encapsulation in ANOVAs for both analyses, each with factors of time and encapsulation; FIGS. 3J and 3K; see Tables 5 and 6 for full statistics). Molecular confinement in liposomes thus may help facilitate higher-order reactions that require multiple chemical building blocks to be brought together, since the restricted movement of reagents increases the probability of the requisite multi-way interactions.

Insulation of Genetic Circuits Operating in Parallel Liposome Populations

As a next step towards engineering sets of liposomes that can communicate with one another, studies were performed to determine whether prepared liposomes could be used to insulate multiple and potentially incompatible genetic circuits from each other, so that they could operate in the same bulk environment. This insulation would enable modular design; each circuit could be optimized independently and deployed in the same environment as other circuits without interference. These circuits could reuse the same parts (proteins, DNA) for different purposes in different liposomes, thereby circumventing one limitation of genetic circuits designed to all operate within the same living cell (where one must assume that all circuit elements might encounter each other and must therefore be inherently orthogonal). Different liposome populations could also contain chemical micro-environments that are not mutually compatible (e.g., bacterial and mammalian extracts, or mammalian transcriptional and mammalian translational machinery) there are numerous examples throughout chemistry of reactions being run under specialized, and thus often isolated, reaction conditions. First, studies were performed to assess whether multiple liposomal circuits could operate in parallel without crosstalk. To do this, populations of liposomes were created that could respond differently to the same external activator. Two populations of liposomes were built that each carried mammalian TX/TL extract and the same amount of Dox-inducible luciferase DNA (either Renilla or firefly luciferase), but varied the amount of alpha-hemolysin DNA to result in high-aHL and low-aHL synell populations (FIG. 4A). High-aHL and low-aHL synells responded to the non-membrane-permeable Dox in the external solution, doing so proportionally to their own aHL concentration (FIG. 4B). No evidence was observed indicating that doxycycline acting upon one liposome population affected expression of luciferase in the other population: specifically, there was no significant difference in fLuc expression in high-aHL fLuc liposomes when the rLuc liposomes were high-aHL vs. low-aHL, and the same held for the other combinations (FIG. 4B; Sidak's multiple comparisons test after ANOVA with factors of luciferase type and alpha-hemolysin combination; see Table 10 for full statistics, and FIGS. 16 and 17 for rLuc and fLuc expression data at different aHL plasmid concentrations, for two different time points). That is, luciferase expression from each liposome population depended only on the amount of aHL DNA present in that population, and not on that of the other population (FIG. 4C-4E). This experiment thus not only verified the independent operation of multiple non-interacting liposomes, but also verified that multiple liposome populations can be programmed in advance to have varying response levels to a given trigger, and subsequently in the same internal solution, triggered to function simultaneously.

Figure 5B:
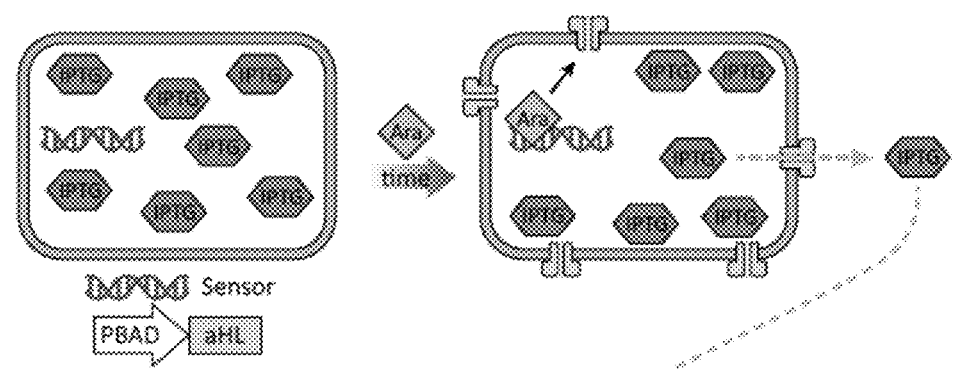
Figure 5C:
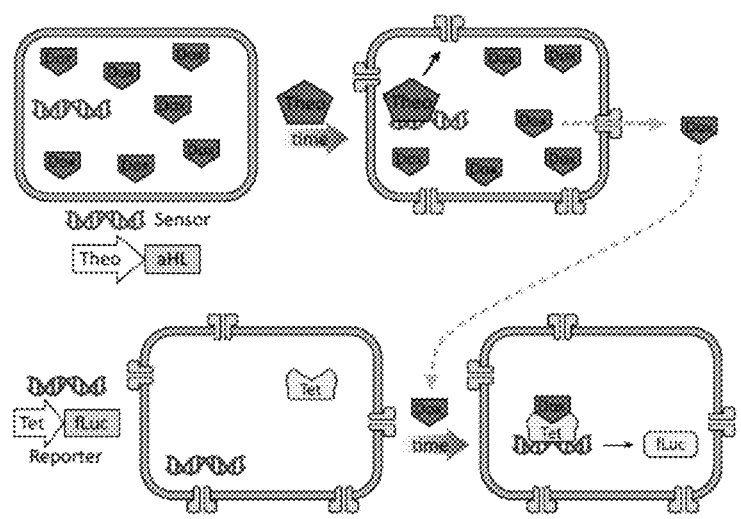
Figure 5D:
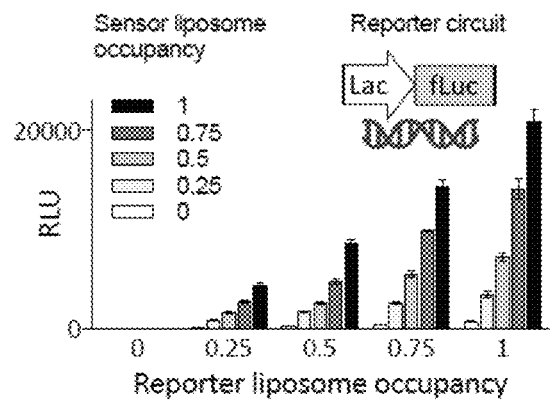
Figure 5E:
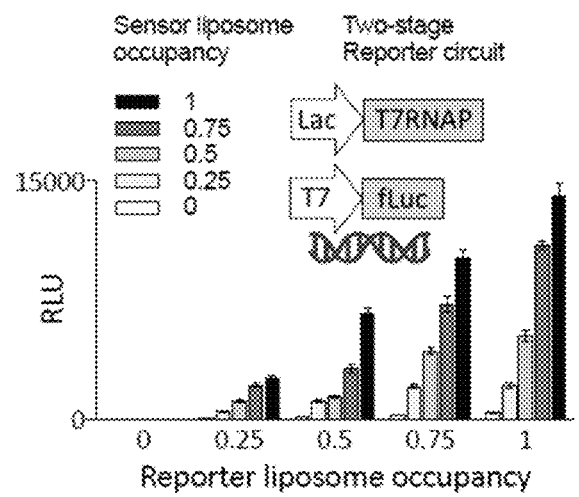
Figure 5F:
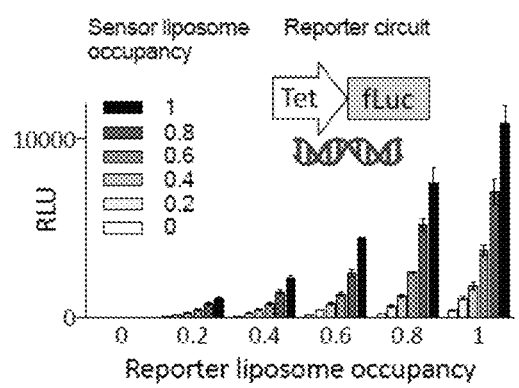
Figure 19:
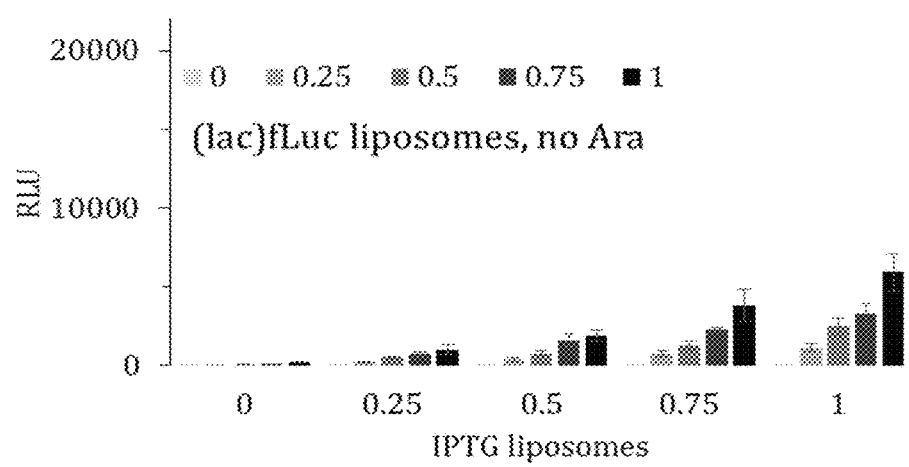
FIG. 19 provides a graph illustrating expression of fLuc under lac promoter in absence of arabinose. The Y-axis is relative light units (RLU) and the x axis is IPTG liposomes. The Y-axis scale is the same as in FIG. 9C.
Figure 20:
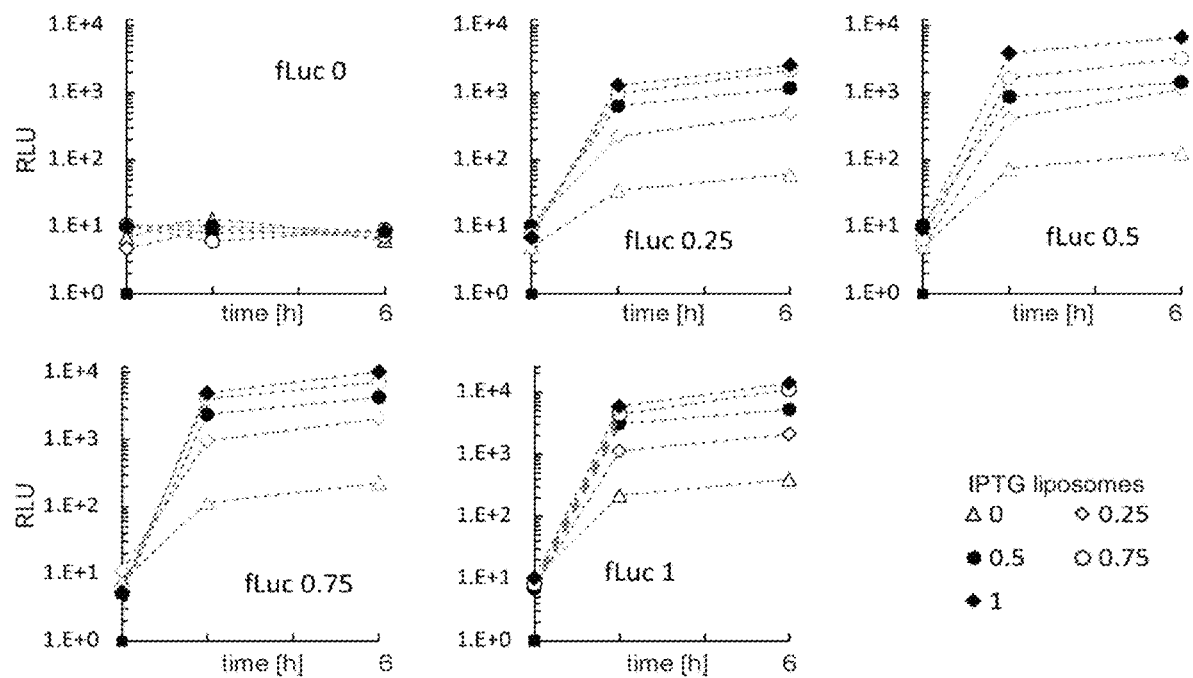
FIG. 20 provides graphs illustrating the time course of fLuc under T7 promoter, driven by T7RNAP under the lac promoter, with different ratios of liposomes. The Y-axis is relative light units (RLU) and the X-axis is time in hours.
Figure 21:
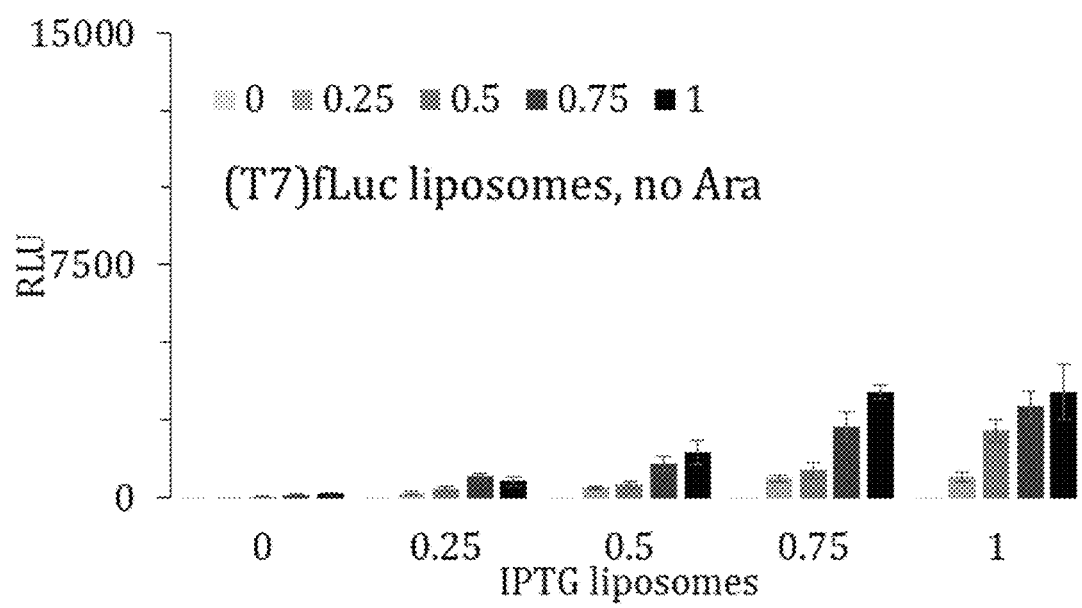
FIG. 21 provides a graph illustrating expression of fLuc under T7 promoter, driven by T7RNAP under the lac promoter, in the absence of Arabinose. The Y-axis is relative light units (RLU) and the x axis is IPTG liposomes. The Y-axis scale is the same as in FIG. 9D.
Figure 22:
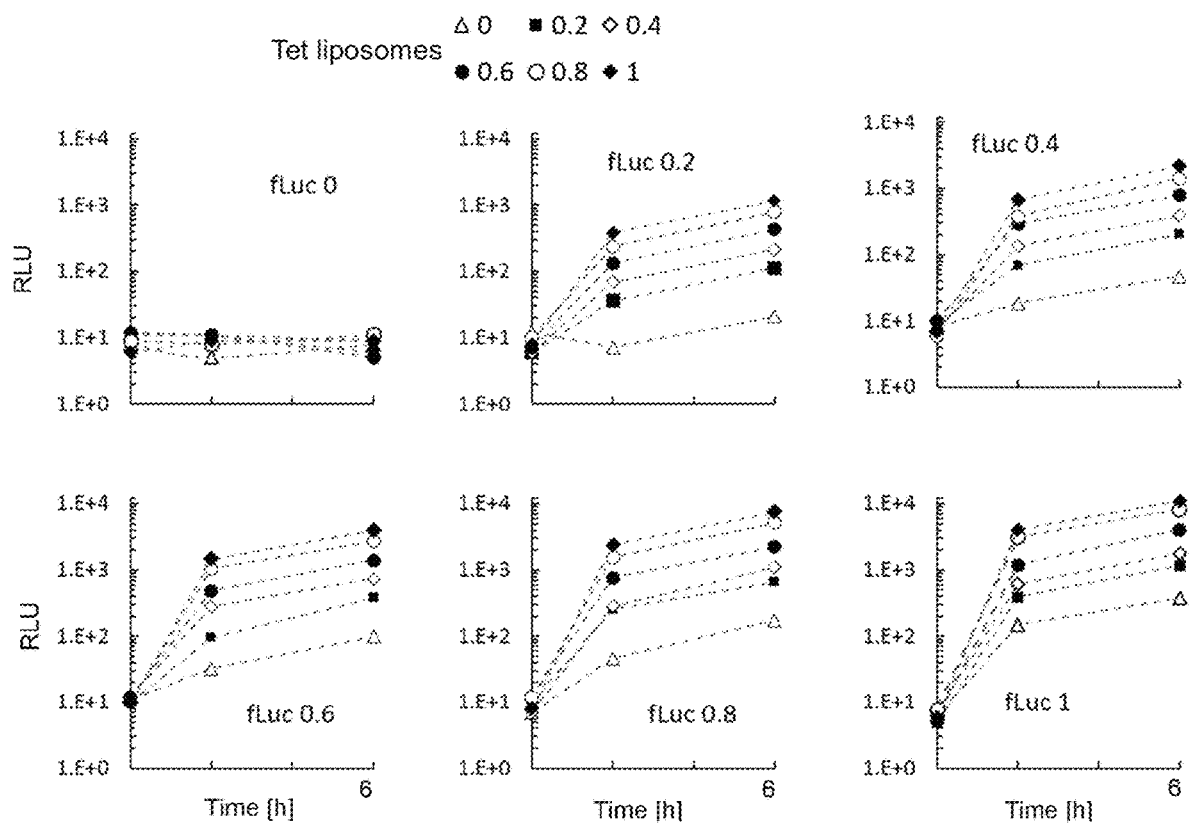
FIG. 22 provides graphs illustrating the time course of fLuc expression at different ratios of fLuc and Tet liposomes. The Y-axis is relative light units (RLU) and the X-axis is time in hours.
Figure 23:
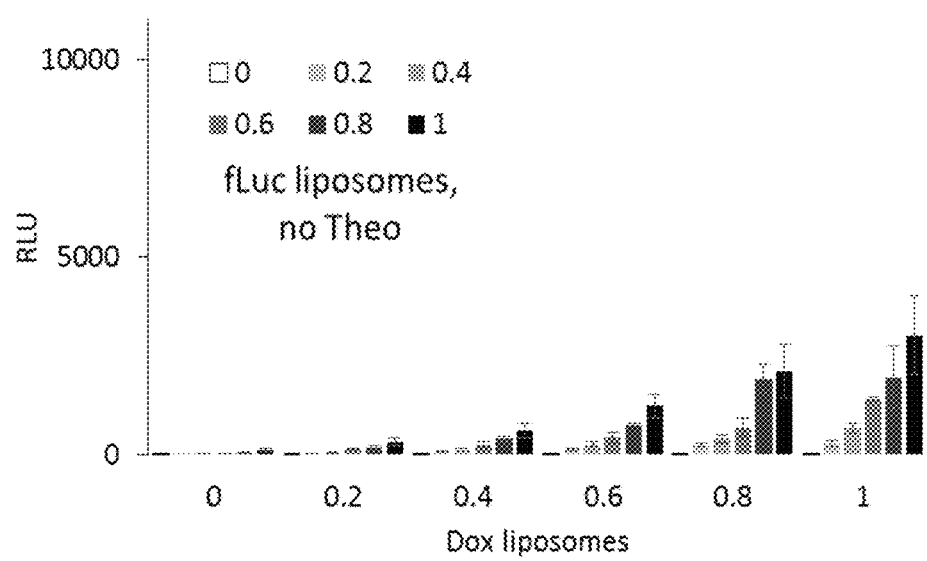
FIG. 23 provides a graph illustrating end-point data for fLuc expression without Theophylline. The Y-axis is relative light units (RLU) and the x axis is Dox liposomes. The Y-axis scale is the same as in FIG. 9F.
Figure 24A:
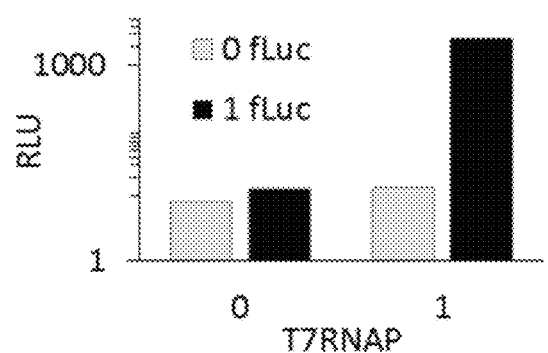
FIG. 24A-D provides graphs illustrating fusion of liposomes and subsequent merging of independent genetic circuits using SNARE protein mimics—with liposome pairs reversed compared to the experiments shown in FIG. 10. SNARE experiments were designed analogously to the results presented in FIG. 10: two populations of liposomes were prepared, each with one of the SNARE protein mimics (see FIG. 10A for the experimental setup). Equal volumes of each population were mixed, containing two different concentrations of the liposomes: 10 mM (1) or zero (0), resulting in 4 different ratios of liposomes tested. All samples were incubated for 6 h after mixing, then end-point fLuc luminescence was analyzed as described in Examples section.
Figure 24B:
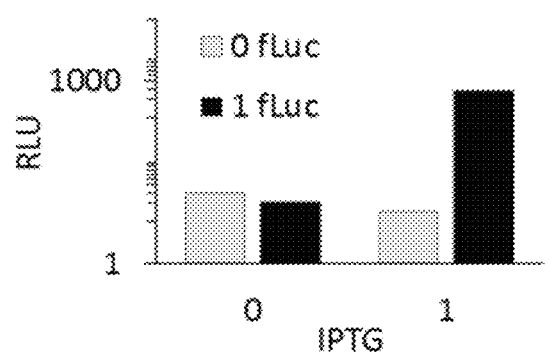
Figure 24C:
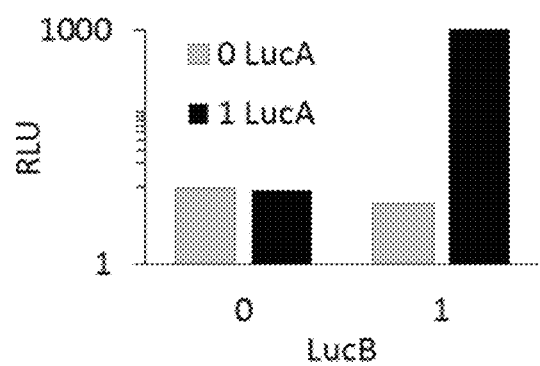
Figure 24D:
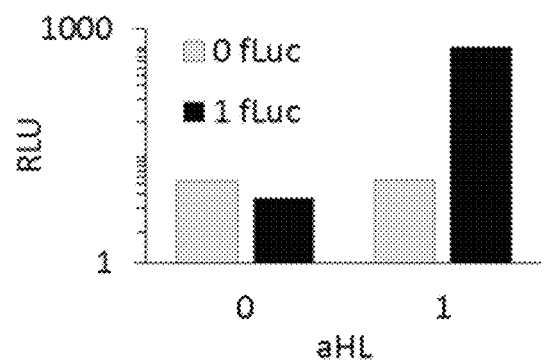
Figure 25A:
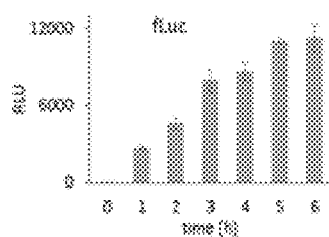
FIG. 25A-F provides graphs showing T7-driven expression of enzymatic reporter proteins in synthetic cells. For each system, the substrate for the enzyme is also shown.
Figure 25A:
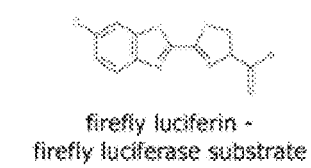
Figure 25B:
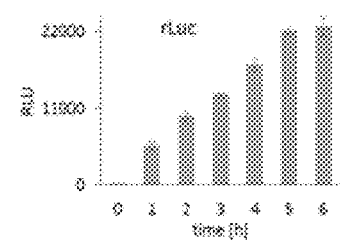
Figure 25B:
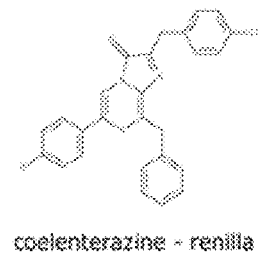
Figure 25C:
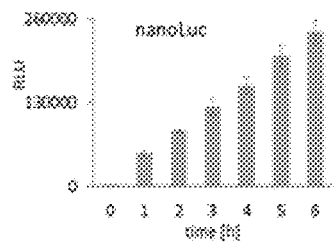
Figure 25C:
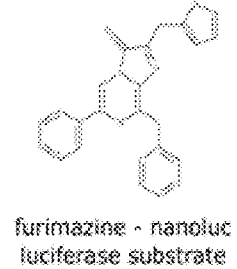
Figure 25D:
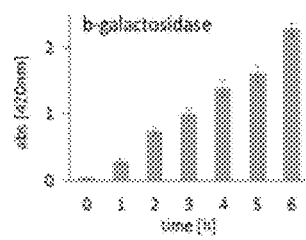
Figure 25D:
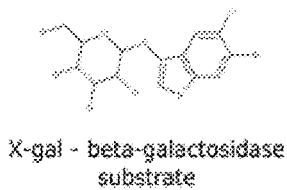
Figure 25E:
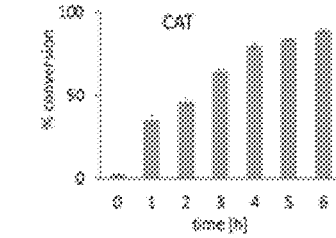
Figure 25E:
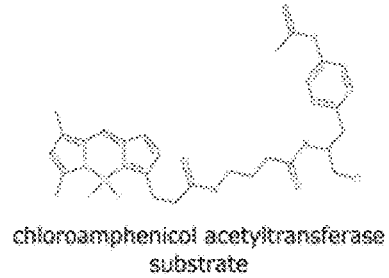
Figure 25F:
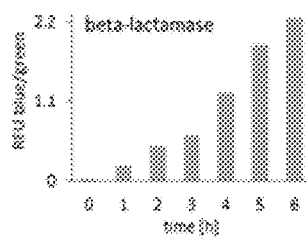
Figure 25F:
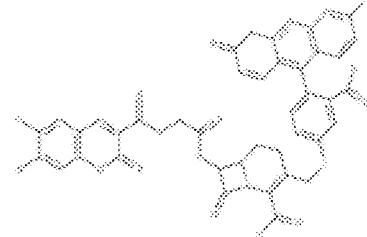
Figure 30:
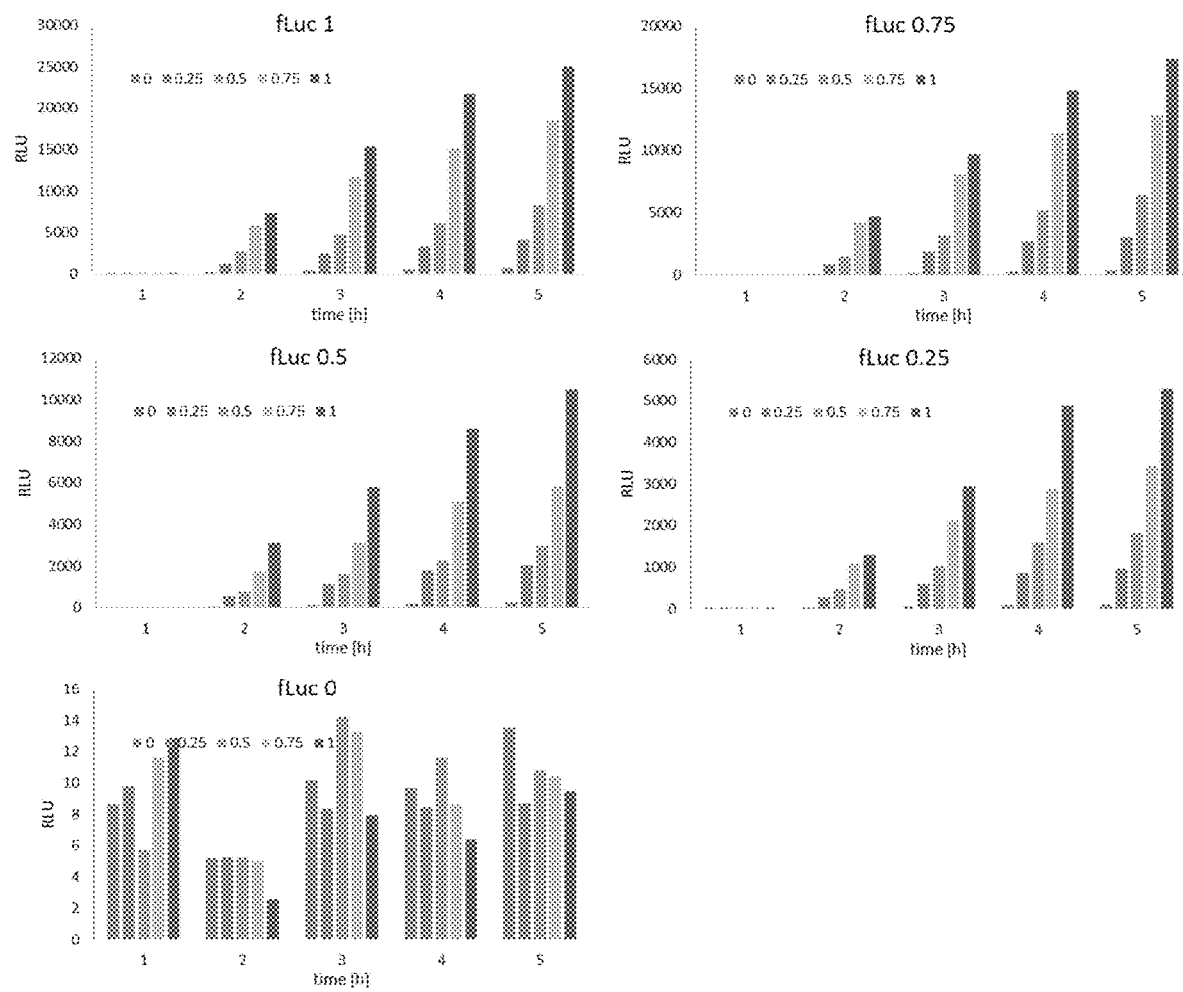
FIG. 30 provides graphs illustrating the time course of expression of fLuc under the lac promoter, with different ratios of liposomes (as in FIG. 5C). Occupancies are numerically defined as in the figure description for FIG. 5.
Figure 31:
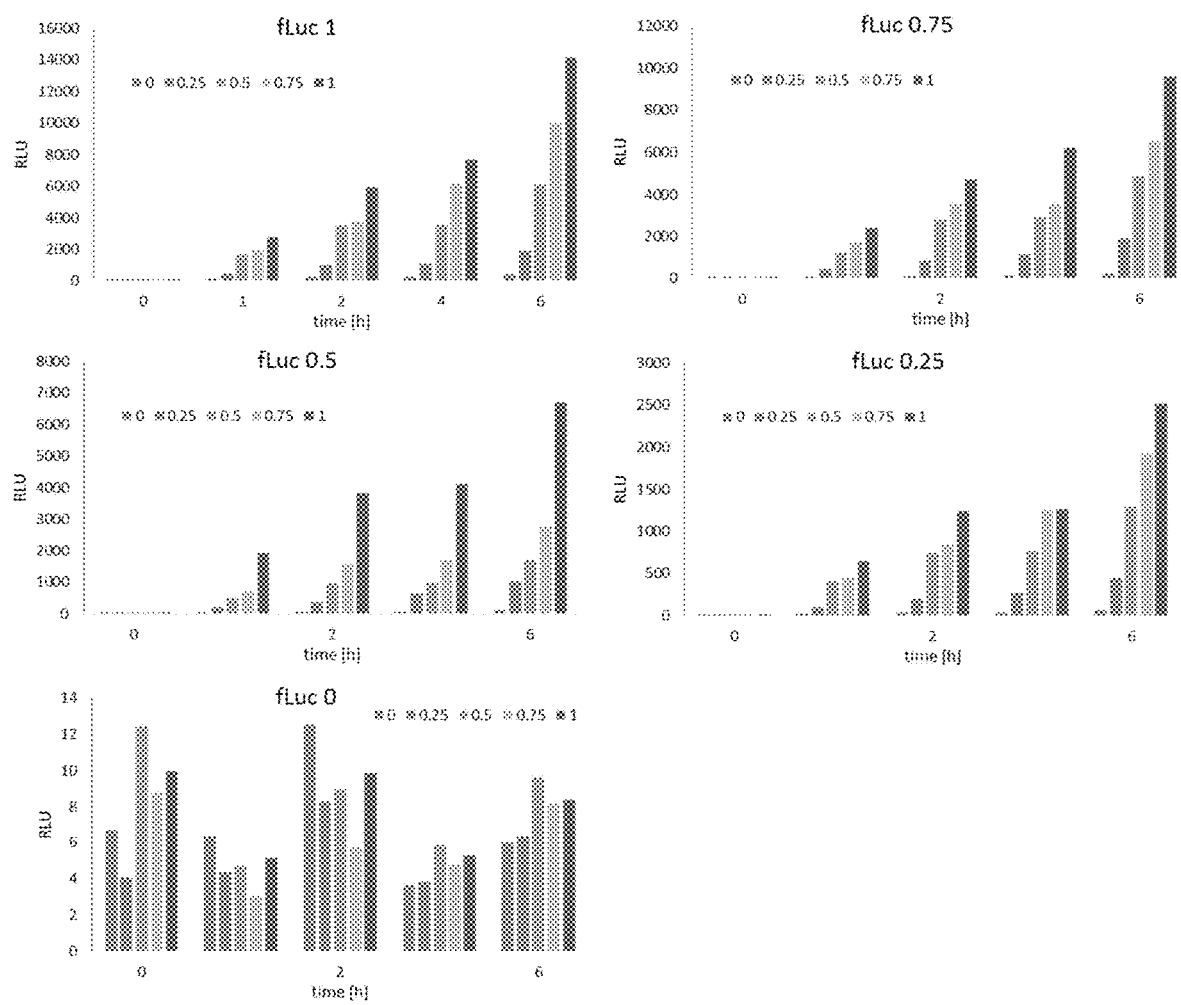
FIG. 31 provides graphs illustrating the time course of fLuc under T7 promoter, driven by T7RNAP under the lac promoter, with different ratios of liposomes (as in FIG. 5D). Occupancies are numerically defined as in the figure description for FIG. 5.
Figure 32:
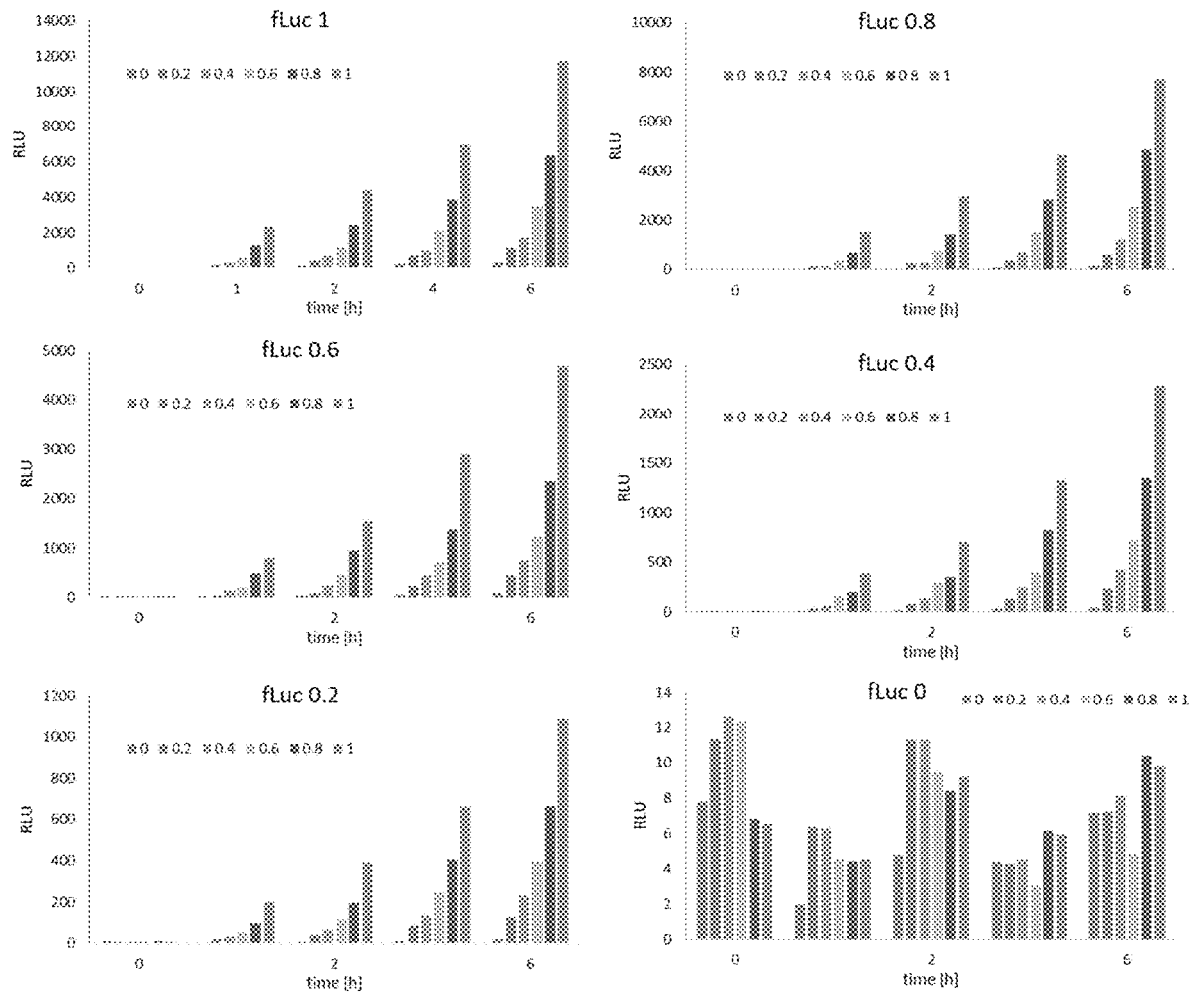
FIG. 32 provides graphs illustrating the time course of fLuc expression at different ratios of fLuc and Tet liposomes (as in FIG. 5F). Occupancies are numerically defined as in the figure description for FIG. 5.

Communication Between Genetic Circuits Operating in Multiple Liposome Populations Having established that genetic circuits in separate populations of liposomes could operate independently, experiments were performed to begin to create controlled communication pathways between populations of synells. In this way, a compartmentalized genetic circuit could be created—which as noted above may need to be separated from others for reasons of control fidelity, toxicity, or reagent tunability—and connect it to other compartmentalized circuits. While previous works have emphasized the importance of modularity in genetic circuits, the experiments described herein were designed for a novel approach to the problem by physically separating circuit elements into different liposomes. Two-component circuits were built by mixing together two populations of liposomes, a "sensor" that senses an external small molecule cue and a "reporter" that receives a message from the sensor population and produces an output; the occupancy of each population could be varied to achieve a different overall ratio of the two components (FIG. 5A; see FIG. 2 for additional characterization of the membrane-permeable small molecules used throughout this figure, and Tables 8 and 9 for the associated statistics). The first version was built with bacterial TX/TL extract (FIG. 5B). The sensor liposomes contained IPTG (a small, non-membrane-permeable activator that induces the lac promoter) and the arabinose-inducible gene for aHL (arabinose, which unlike IPTG, is membrane-permeable); these liposomes thus sensed arabinose and released IPTG by expressing aHL channels. This version was combined with reporter liposomes containing constitutively expressed aHL, in which fLuc was under the control of the lac promoter— either directly (fLuc under lac promoter) or indirectly (T7RNAP under the lac promoter and fLuc under T7 promoter)—and it was found that multi-component compartmentalized genetic circuits thus constructed were able to operate as coherent wholes. Both systems were tested with multiple dilutions of sensor and reporter liposomes, and found similar dose-response curves from titration of either species of liposome (FIGS. 5C and 5D; bars in these panels represent final time points of 6 h; for the complete time series that includes the data in FIG. 5C, see FIG. 30; for the end-point expression of the circuit in FIG. 5C without arabinose triggering, see FIG. 19; for the complete time series that includes the data in FIG. 5D, see FIG. 31; for the end-point expression of the circuit in FIG. 5D without arabinose triggering, see FIG. 21). Using this modular architecture, a genetic circuit was constructed that combined both bacterial and mammalian components (FIG. 5E). The sensor liposome in this case responded to theophylline (membrane permeable) to release doxycycline (non-membrane-permeable). Dox, in turn, activated fLuc expression in reporter liposomes built with mammalian components. As before, the results showed that the multicompartment genetic cascade could function as designed, with fLuc expression dose-response curves similar upon titrating either sensor or reporter liposome concentration (FIG. 5F; bars in this panel represent final time points of 6 h; for the complete time series that includes the data in FIG. 5F, see FIG. 32; for the end-point expression of the circuit in FIG. 5F without theophylline triggering, see FIG. 23). Thus, even multi-component genetic circuits with different chemical microenvironments (e.g., made from bacterial vs. mammalian cell extracts) could be assembled into coherent networks comprising multiple modules.

Fusion of Complementary Genetic Circuits

Figure 33:
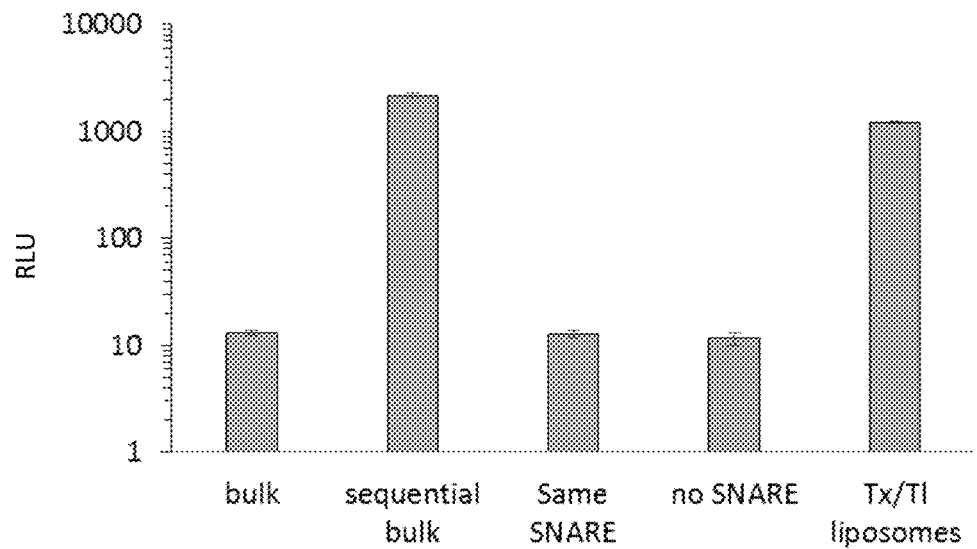
FIG. 33 provides a graph showing results from cell-free transcription and translation in mammalian cell-free systems. From left to right, the bars correspond to: Bulk: cell-free TX and TL systems, same as used in experiments presented in FIG. 6F, but mixed in one tube instead of encapsulating in separate liposomes, and incubated for 24 hours at 37° C. Sequential bulk: the TX reaction incubated for 12 hours, then mixed with equal volume of the TL mixture, incubated for another 12 hours (like experiment of FIG. 6F, but without liposome encapsulation). Same SNARE, no SNARE and TX/TL liposomes are the same data as presented on FIG. 6F, shown here again for reference.

Finally, having established that it is possible to maintain liposomes in high-integrity states despite being mixed, studies were performed to engineer synells to fuse so that they could bring together two genetic cascades into the same environment in a programmable fashion. Two precursors might require synthesis in different milieus, but ultimately need to be reacted with one another. One prominent example is that of mammalian transcription and translation. Mixed mammalian transcription and translation cell-free extracts are not able to functionally result in transcription of DNA into RNA and then the translation of RNA into protein, perhaps because the micro-environments of the mammalian nucleus and cytoplasm are quite different, making their cell-free extracts incompatible (FIG. 33).

Rather than mixing the two cell-free extracts into a single non-functioning mixture, it might be preferred to use synells to compartmentalize the reactions. Once nuclear-extract synells have completed transcription, it might be desirable to fuse them with cytoplasmic-extract synells for translation to take place.

Figure 6A:
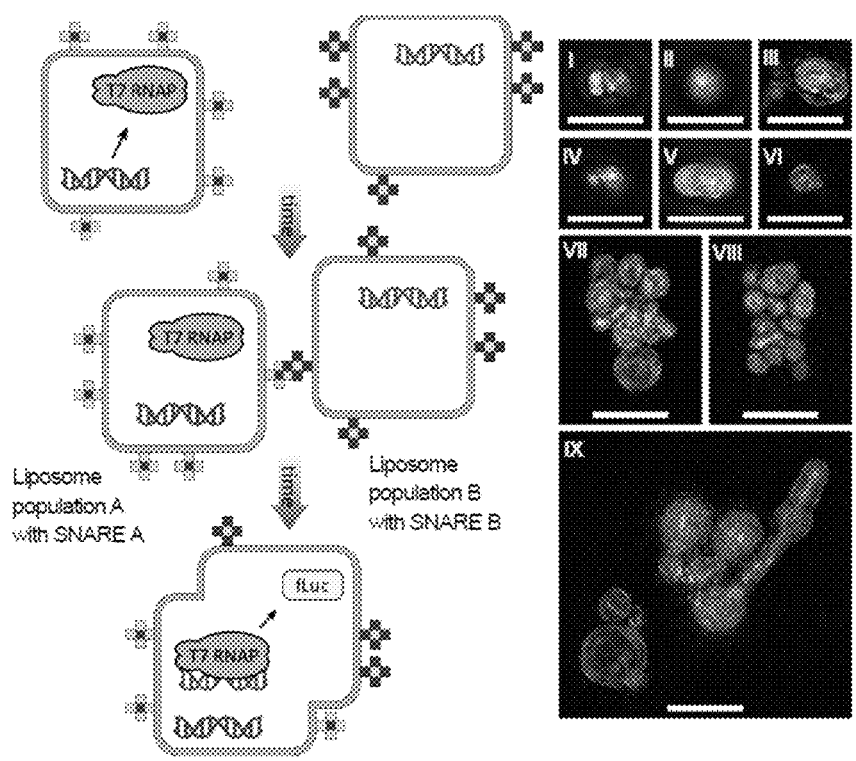
FIG. 6A-F provides schematic diagrams, photomicrographic images, and graphs Fusion of complementary genetic circuits.
Figure 6B:
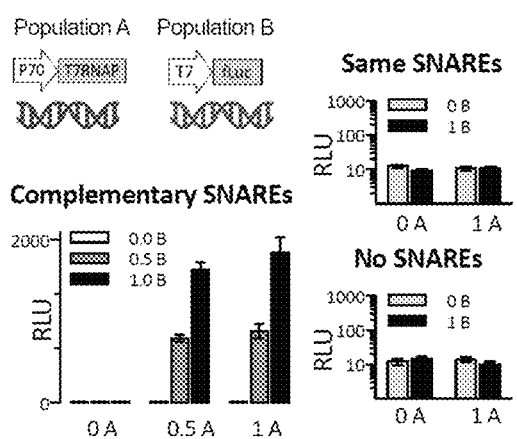
Figure 6C:
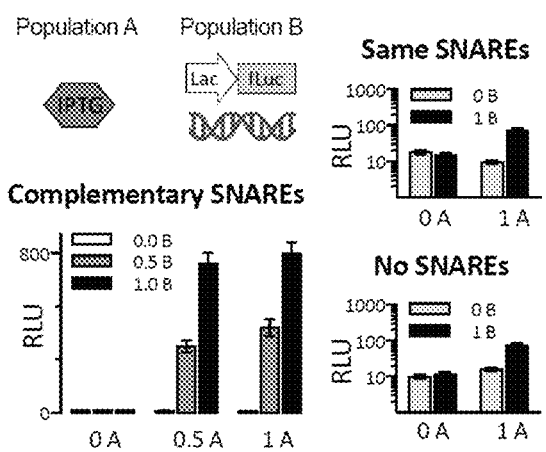
Figure 6D:
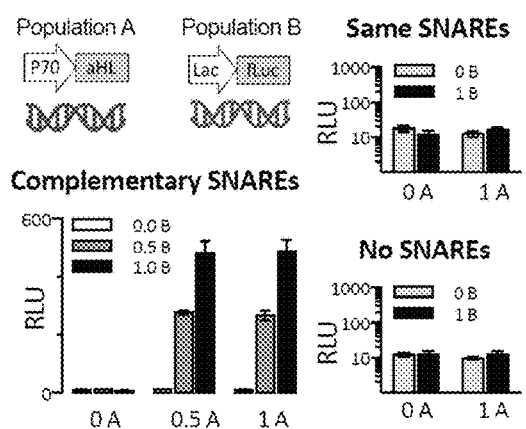
Figure 6E:
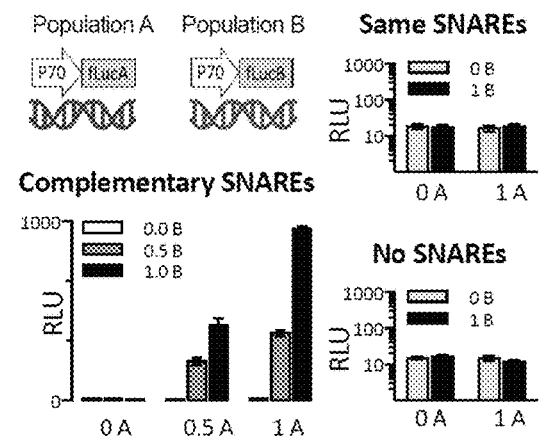
Figure 6F:
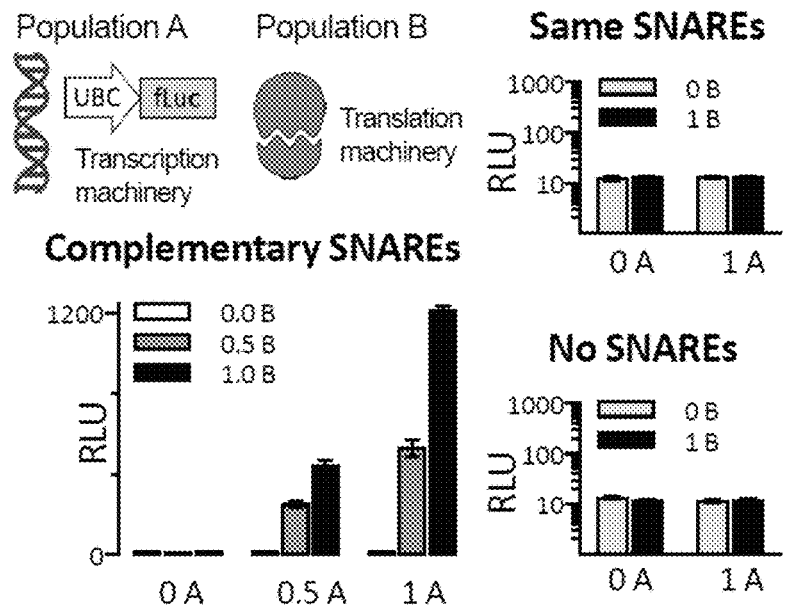
Figure 34:
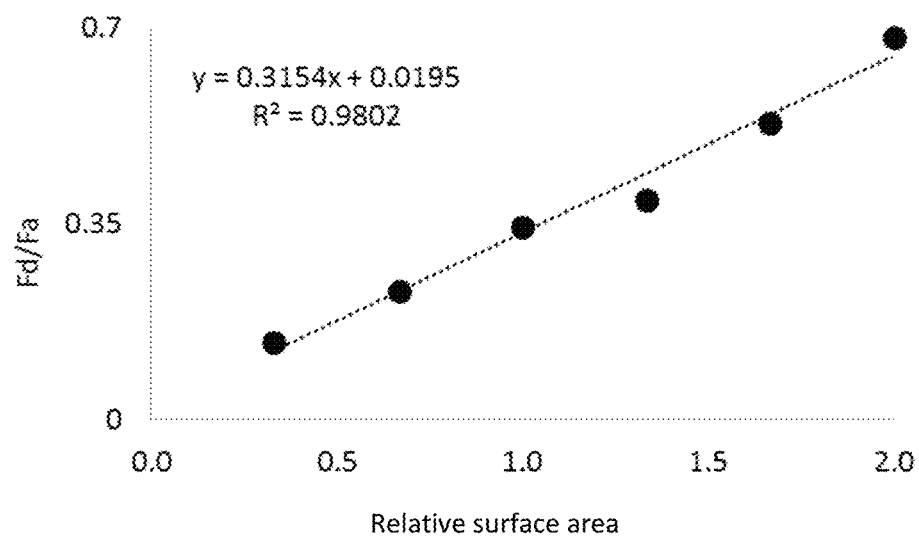
FIG. 34 provides a calibration curve for FRET response. The samples were prepared with varying ratios of the FRET dye pair lipids (LISSAMINE™ Rhodamine B 1,2-Dihexadecanoyl-sn-Glycero-3-Phosphoethanolamine, Triethylammonium Salt and NBD-PE (N-(7 Nitrobenz-2-Oxa-1,3-Diazol-4-ye-1,2-Dihexadecanoyl-sn-Glycero-3-Phosphoethanolamine, Triethylammonium Salt)) to the POPC:cholesterol lipid mix, in order to mimic surface area change in fusion experiments. Fd, fluorescence of donor; Fa, fluorescence of acceptor; the relative surface area of 1 is defined as the starting ratio of FRET dyes to lipids in the SNARE fusion experiment samples, and subsequent values of surface are obtained by scaling proportionally (increasing or decreasing) the concentration of FRET dyes in the membrane, as described previously in Chen, I. A. & Szostak, J. W. A (2004) Biophys. J. 87, 988-998 and Chen, I. A. et al., (2005) J. Am. Chem. Soc. 127, 13213-13219.
Figure 35:
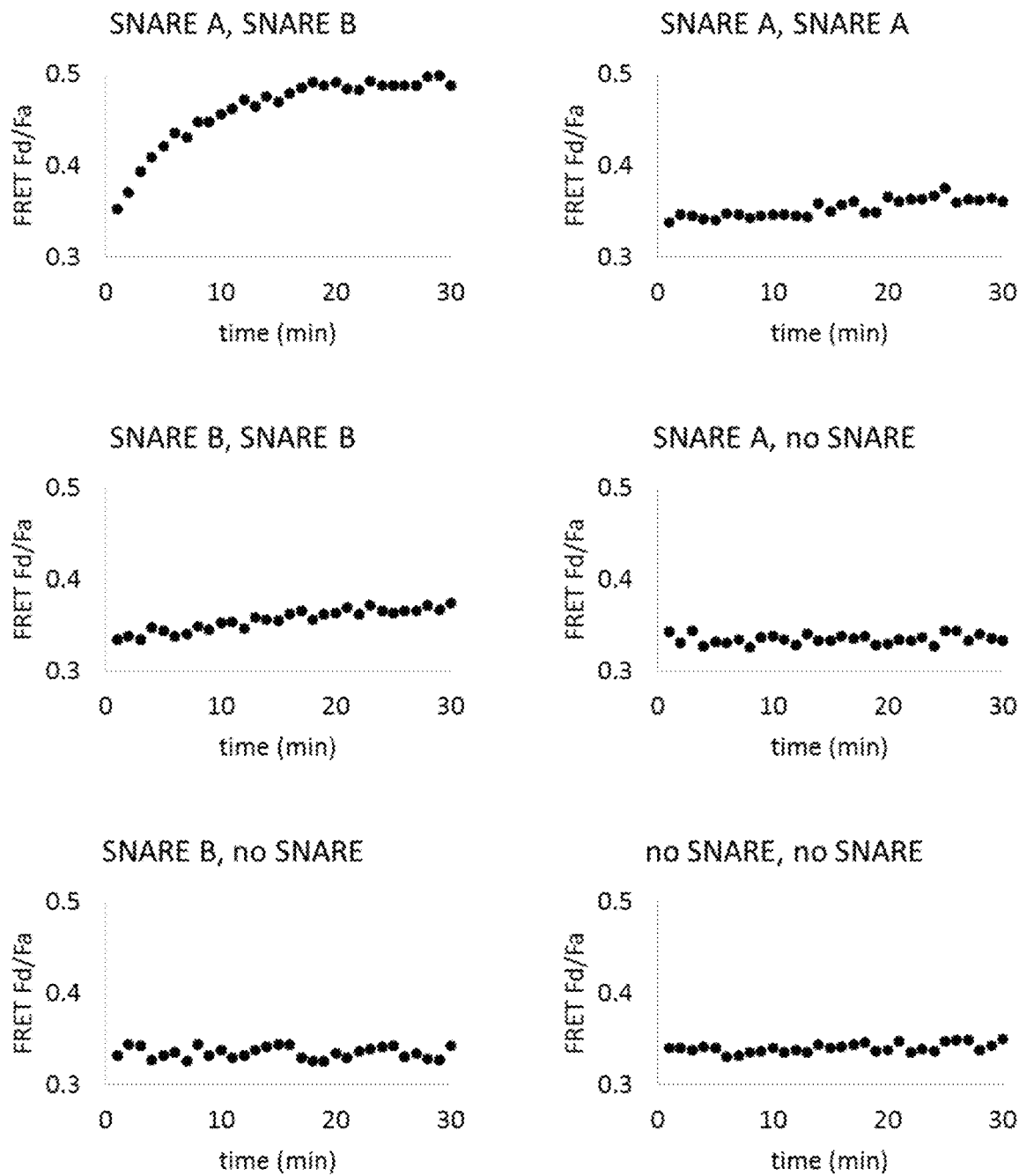
FIG. 35 provides graphs illustrating results from liposome fusion induced by SNARE protein mimics. The mixing of liposomes was measured with changes of FRET signal from the FRET donor and acceptor dyes in the liposomes, both to confirm mixing and as a way to estimate the time course of vesicle size increases due to fusion. Experimentation details are provided herein in Examples, Materials and Methods. The letters A and B represent a pair of SNAREs that bind to one another; when A is paired with A, or B with B, no binding or fusion happens.
Figure 36:
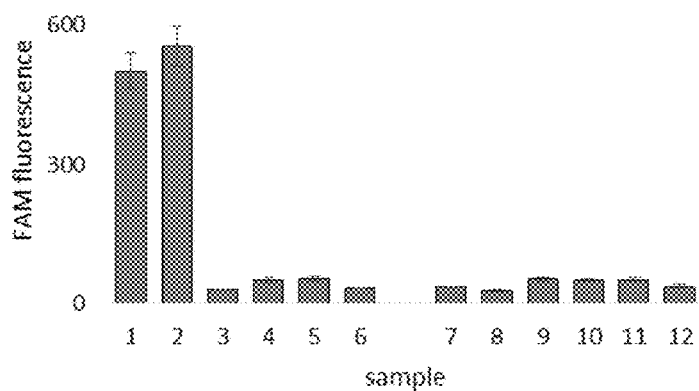
FIG. 36 provides a table and graph of de-quenching of a liposome-encapsulated molecular beacon upon SNARE mediated fusion with liposomes encapsulating a complementary target. Molecular beacon FAM-5'-gcgagctag-gaaacaccaaagatgatatttgacgc-3'-DABCYL (SEQ ID NO: 2), with SEQ ID NO: 1 being the sequence: gcgagctaggaaacac-caaagatgatatttgctcgc, was encapsulated in one population of liposomes ("probe" liposomes), and a complementary target ("positive target") or a non-complementary target ("negative target") were encapsulated in the other population of liposomes. Liposomes were prepared and purified according to the general procedures described in the Examples section, Material and Methods. Samples were then mixed, incubated for 30 min at room temperature, and fluorescence of the fluorescein (FAM) dye was measured. The increased fluorescence indicates de-quenched FAM probe as a result of hybridization of a molecular beacon to the target sequence, and thus mixing of the content of the liposomes upon SNARE-mediated fusion. Error bars indicate S.E.M. n=3.
Figure 37:
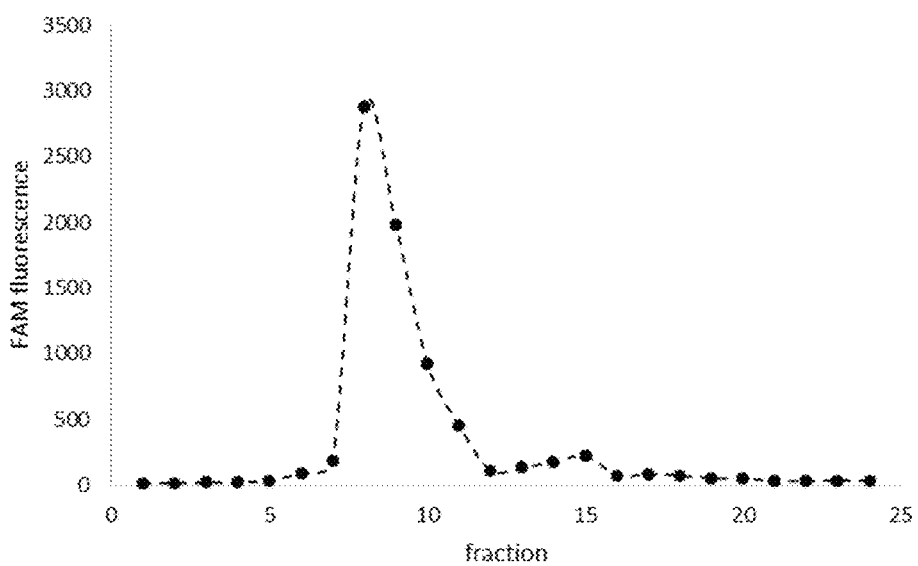
FIG. 37 provides a graph showing leakage of DNA oligonucleotide from liposomes after SNARE-induced fusion. The fluorescent oligonucleotide 5'-FAM-d(gcg cat tgg)-3' was encapsulated at 1 µM in both populations of liposomes containing SNARE A and SNARE B (a matched pair, as defined in FIG. 6A). The liposomes were extruded and purified as described in the Examples section, Materials and Methods, and fusion reactions were performed. After fusion and 1 h equilibration, the sample was purified on a Sepharose 4B size-exclusion column. The combined total free-molecule fraction fluorescence is about 8.2% of the total fluorescence measured from all liposome and free-molecule fractions (the liposome fraction was defined as the sum of fractions 6 to 12, and the free-molecule fraction as the sum of fractions 13 to 17).

Thus, experiments were performed in which liposomes capable of controlled fusion (FIG. 6A) were prepared. Unlike prior efforts to fuse liposomes of opposite charge to activate gene expression in liposomes, different method was utilized. A system described and demonstrated herein used a single kind of membrane composition (POPC cholesterol membranes, known to be a good environment for membrane channels like aHL), so to achieve fusion between liposomes SNARE/coiled-coil hybrid proteins (here called SNAREs for short) were used, which could be generated in complementary pairs that were specific in their fusion properties Neyenberg, K., et al., (2011) Chem. Commun. 47, 9405-9407 and Robson Marsden, et al., (2013) Biomater. Sci. 1, 1046-1054]. Thus, complementary circuit elements could be fused together by encapsulating them in separate populations of SNARE-fusable liposomes. Experiments were performed and confirmed that SNAREs were mediating liposome fusion, through SIM imaging (FIG. 6A), by observing Fluorescence Resonance Energy Transfer (FRET) signals from lipid dyes added to the liposome membranes (FRET signals showed that the fusion process takes place within minutes; see FIGS. 34 and 35) and by observing mixing of liposome content, reported as de-quenching of a molecular beacon encapsulated in one population of liposomes by a complementary target encapsulated in the other population (see FIG. 36). Large liposomes and also liposome aggregates (presumably in the process of fusing) of sizes on the order of 5-10 µm, were observed and a minimal amount of leakage from the liposomes during the process of fusion was measured (FIG. 37). Several combinations of complementary circuit elements were tried: the gene for T7RNAP and a T7-driven fLuc (FIG. 6B); a non-membrane permeable small molecule trigger (IPTG) and an IPTG-triggered (lac-promoter driven) fLuc (FIG. 6C); genes for a membrane pore (aHL) and a lac-promoter driven fLuc (FIG. 6D, in an IPTG-containing ambient); two different genes encoding for parts of split luciferase (FIG. 6E, using the same fLucA and fLucB as in FIG. 3B). For one final test, liposomes carrying mammalian nuclear (transcription) extract and the gene for fLuc, incubated for 12 hours, were then mixed with liposomes containing cytoplasmic (translation) extract, and further incubated for 12 hours (FIG. 6F). Production of fLuc protein was observed, even though a direct combination of transcriptional and translational machinery produced no fLuc above background levels (FIG. 33). Throughout all these cases, production of the final output of the genetic cascade was observed only when the two liposome populations were equipped with SNAREs, and only when they were a SNARE cognate pair ($P<0.0001$ for factor of SNARE compatibility, ANOVA with factors of mechanism, occupancy, and SNARE compatibility; see Table 13 for full statistics; for systems in this figure, switching which liposome contained which SNARE had no effect on the results, as shown in FIG. 24).

Table 13

TABLE 13

Statistics for FIG. 6: 3-way ANOVA with factors of "Mechanism", "Occupancy A", "Occupancy B", and "SNARE compatibility", (i.e., whether the SNARE protein mimics are complementary, equal, or not present).

| Source | Nparm | DF | Sum of Squares | F Ratio | Prob > F |
|---|---|---|---|---|---|
| Mechanism | 4 | 4 | 1878842.8 | 6.1006 | <.0001 |
| Occupancy A | 2 | 2 | 3944276.1 | 25.6142 | <.0001 |
| Occupancy B | 2 | 2 | 4663508.3 | 30.2849 | <.0001 |
| SNARE Type | 2 | 2 | 3745780.4 | 24.3251 | <.0001 |

Studies described herein were performed to assess a key issue in synthetic biology: the modularity of multi-component genetic circuits and cascades. The results have now shown that by encapsulating genetic circuits and cascades within synells (FIGS. 1A and 1B) and orchestrating the synells to either operate in parallel (FIG. 1C), communicate with one another (FIG. 1D), or fuse with one another in a controlled way (FIG. 1E), it is possible to create and utilize genetic cascades that take advantage of the modularity enabled by liposomal compartmentalization. The strategy of the experiments described below herein enabled genetic cascades to proceed in well-isolated environments while permitting the desired degree of control and communication. Examples of certain design strategies for constructing and utilizing such synell networks are provided herein, thus expanding the utility of liposome technology and improving the modularity of synthetic biology. Synell networks may support complex chemical reactions that would benefit from both the high-fidelity isolation of multiple reactions from one another, as well as controlled communication and regulatory signal exchange between those reactions. Shown herein, for example, are studies and results demonstrating successful controlled fusion of two populations of synells that contain mammalian transcriptional and mammalian translational machinery, respectively, which are normally incompatible when combined in the same compartment. Methods of the invention permit successful fusion that was not previously possible.

Liposomes are key in chemistry and chemical biology for compartmentalizing chemical reactions from one another, important for when reactions are incompatible or necessarily controlled in independent ways. In this disclosure these important features are shown in the context of genetic circuits, which are at the core of synthetic biology. As will be appreciated, the subject disclosure demonstrates that many key advantages of liposomal chemical compartmentalization can be seen in this context, enabling synthetic minimal cells (SMCs): for example, the well-known molecular crowding effect of liposomes carries over to multicomponent genetic circuits, facilitating three-way protein-protein interactions that are less likely to occur in bulk solution than lower-order reactions. Further, the disclosure demonstrates small-molecule triggering of genetic circuitry, both using cell-permeant and cell-impermeant activators (the latter requiring a pore, alpha-hemolysin). By titrating the amount of activator or the amount of pore, it has been shown that it was possible to regulate such circuits within both single and multiple populations of liposomes. (Arabinose, in particular, may emerge as a useful trigger for such cascades due to its remarkably low baseline.) Starting from these building blocks, communication between multiple independent SMCs was explored, with both permeable and impermeable actuators being delivered to or exchanged from SMCs carrying materials from even different domains of life. Finally, the use of SNARE mimics to fuse liposomes together was explored, enabling the direct reunion of separately synthesized reaction components into one environment. Scaled up, in the future such strategies could in principle support new kinds of combinatorial chemistry in which genetic circuits—rather than small molecules—are fused together.

In this way, a set of building blocks have been created that enable liposome-compartmentalized TX/TL systems equipped with well-defined genetic circuits, or SMCs, to be remotely activated, to communicate with each other, and to fuse when appropriate. In other words, SMCs enable a new level of modularity to be brought into synthetic biology. Modularity is key in engineering, because breaking a complex synthetic biology system into parts that can be independently controlled or regulated, without crosstalk, and that communicate only in well-defined ways, enables each part to be individually optimized while supporting their incorporation into an emergent whole. Technologies, methods, and compositions disclosed herein may enable a large number of different synthetic biology problems to be made modular, even those that involve genetic cascades that might interfere with each other (or even pose toxicity issues) if they were to all occur in one pot. Because embodiments of methods disclosed herein for compartmentalization are liposomal, there is no need for specialized hardware to mediate the communication and control of multiple interacting reaction systems. Precise temporal control of synell networks can also be further enhanced by using light to trigger optogenetic signaling cascades, which in turn can trigger downstream effects [see for example, Ingles-Prieto, A., et al., Nat. chem. Boil. 11, 952-954 and Boyden, E. S. (2011) F1000 biol. Rep. 3, 11.]. It has now also been shown herein that the molecular confinement of liposomes can facilitate multicomponent protein-protein interactions.

Certain embodiments of SMCs as disclosed herein, in addition to the power offered to synthetic biology, may also enable simulation of various complex behaviors that have been proposed as characteristics of early life forms. Controlled communication between cells, fusing genetic elements across cells, and assembling complex genetic cascades towards defined cellular behaviors are all traits that arose in the course of early evolution. Synthetic minimal cells have been widely used as models for studying the origin and earliest evolution of life. Hanczyc, M. M. et al., (2003) Science 302, 618-22; Adamala, K. et al., (2013) Nat. Chem. 5, 495-501; Szostak, J. W. et al., (2001) Nature 409, 387-390; Adamala, K. et al., (2014) Computational and Structural Biotechnology Journal 9(14); and Ruiz-Mirazo, K. et al., (2014) Chem. Rev. 114, 285-366. For example, it has previously been shown that liposomes encapsulating a simple catalyst can be used to model early Darwinian competition mechanisms [see: Adamala, K. et al., (2013) Nat. Chem. 5, 495-501]. Interacting encapsulated genetic circuits can enable the study of the more complex characteristics that have been proposed for the last universal common ancestor (LUCA) Glansdorff, N. et al., (2008) Biology Direct 3; Woese, C., (1998) Proc. Natl. Acad. Sci. U.S.A 95, 6854-6859; and Theobald, D. L., (2010) Nature 465, 219-222, perhaps helping reveal the dynamic and boundary conditions underlying the mechanism of Darwinian evolution.

Liposomes are important in chemistry and chemical biology for compartmentalizing chemical reactions that require different environments or act on different samples. In these examples presented herein, it has been demonstrated how synthetic minimal cells (synells)—liposomes containing genes as well as transcriptional and/or translational machinery—enable a great level of modularity for genetic circuit design and execution. It has also now been demonstrated that circuits could be designed to run in synell populations in the same container, independent of each other due to the insulation provided by the liposomal membrane. Genetic circuits were also prepared that could also be connected to communicate with one another through small molecule messengers. This communication was possible even across liposomes containing incompatible micro-environments, as was shown herein by constructing the first genetic circuit containing bacterial and mammalian cell-free extracts and genetic elements. In addition, studies described herein explored the use of SNARE mimics to fuse synells together, enabling the direct union of separately synthesized reaction components. Using this strategy, it was demonstrated that RNA encoding for firefly luciferase (fLuc) was able to be produced in one population of liposomes containing mammalian transcriptional extract, which upon fusion with liposomes containing mammalian translational extract resulted in protein production—an outcome that would not occur if the gene was simply added to a mixture of the two extracts.

EQUIVALENTS

It is to be understood that the methods and compositions that have been described above are merely illustrative applications of the principles of the invention. Numerous modifications may be made by those skilled in the art without departing from the scope of the invention.

Although the invention has been described in detail for the purpose of illustration, it is understood that such detail is solely for that purpose and variations can be made by those skilled in the art without departing from the spirit and scope of the invention which is defined by the following claims.

The contents of all literature references, publications, patents, and published patent applications cited throughout this application are incorporated herein by reference in their entirety.

We claim:

1. A first synthetic minimal cell (SMC) comprising at least two genes that are components of a first multi-gene genetic circuit, wherein an activity of a first of the at least two genes in the first SMC modulates an activity of at least one of: (1) one or more additional genes in the first SMC that are components of the first multi-gene genetic circuit and (2) one or more genes in a second SMC, wherein the one or more genes in the second SMC are independently selected and optionally are components of a second multi-gene genetic circuit.

2. The first SMC of claim 1, wherein the second SMC comprises an additional gene.

3. The first SMC of claim 1, wherein contacting the first SMC with an externally delivered agent modulates an activity of at least one gene of the first multi-gene genetic circuit, and optionally, wherein the activity of the first gene of the first SMC modulates an activity of one or more additional genes of: (1) the first multi-gene genetic circuit in the first SMC and (2) the one or more independently selected genes in the second SMC.

4. The first SMC of claim 3, wherein an activity of the first multi-gene circuit comprises expression of one or more polypeptides encoded by a gene of the first multi-gene circuit.

5. The first SMC of claim 1, further comprising one or more of (a) a bacterial extract sufficient for transcription/translation (TX/TL); and (b) a mammalian extract sufficient for transcription/translation (TX/TL).

6. The first SMC of claim 1, further comprising one or more expression vectors comprising one or more of the at least two genes.

7. The first SMC of claim 6, wherein the one or more expression vectors comprise one or more of: a promoter sequence and a polynucleotide sequence encoding a polypeptide.

8. The first SMC of claim 7, wherein the polynucleotide sequence encodes at least one of a membrane channel polypeptide and a detectable label polypeptide.

9. The first SMC of claim 1, further comprising a fusion-inducing polypeptide on the first SMC's exterior surface.

10. The first SMC of claim 1, wherein the first SMC is fused to at least one second SMC comprising at least one of an independently selected gene of an independently selected multi-gene genetic circuit.

11. A composition comprising a plurality of synthetic minimal cells (SMCs) each SMC comprising at least one gene of at least one multi-gene genetic circuit, wherein the at least one gene and the at least one multi-gene genetic circuit of each of the SMCs of the plurality of SMCs are independently selected, and wherein at least one SMC of the plurality of SMCs generates a gene product that alters generation of a gene product encoded in another SMC in the plurality of SMCs.

12. The composition of claim 11, wherein the SMCs in the plurality of SMCs each comprise the at least one gene of the same at least one multi-gene genetic circuit.

13. The composition of claim 11, wherein contacting an SMC of the plurality of SMCs with an externally delivered agent modulates an activity of the at least one gene of the at least one multi-gene genetic circuit of the contacted SMC.

14. The composition of claim 11, wherein at least one of the SMCs in the plurality of SMCs is fused to another of the SMCs in the plurality of SMCs.

15. The composition of claim 11, wherein an activity of one or more of the at least one multi-gene genetic circuits is modulated by an agent.

16. The composition of claim 11, wherein an activity of a first of the at least one gene of the at least one multi-gene genetic circuit of an SMC of the plurality of SMCs modulates an activity of one or more additional of the at least one gene of at least one of: (1) the at least one multi-gene genetic circuit of the SMC and (2) at least one of the independently selected multi-gene genetic circuit of another SMC of the plurality of SMCs.

17. The composition of claim 16, wherein the at least one independently selected multi-gene genetic circuit of (2) is different than the at least one multi-gene genetic circuit of (1).

18. The composition of claim 11, wherein the plurality of SMCs comprise one or more independently selected expression vectors.

19. A method of producing and collecting a polypeptide, the method comprising:
  (a) preparing a composition comprising a plurality of synthetic minimal cells (SMCs) each SMC comprising at least one gene of at least one multi-gene genetic circuit, wherein the at least one gene and the at least one multi-gene genetic circuit of each of the SMCs of the plurality of SMCs are independently selected, wherein at least one SMC of the plurality of SMCs generates a gene product that alters generation of a gene product encoded in another SMC in the plurality of SMCs;
  (b) determining the presence of a polypeptide expressed in the SMCs; and
  (c) collecting the determined polypeptide from the SMCs.

20. A method of modeling a biological process, the method comprising:
  (a) preparing a composition comprising a plurality of SMCs, each SMC comprising at least one gene of at least one multi-gene genetic circuit, wherein the at least one gene and the at least one multi-gene genetic circuit of each of the SMCs of the plurality of SMCs are independently selected, and wherein at least one SMC of the plurality of SMCs generates a gene product that alters generation of a gene product encoded in another SMC of the plurality of SMCs, and
  (b) assessing one or more characteristics of the plurality of SMCs.

21. A method of identifying an effect of a candidate compound on an activity of a first multi-gene genetic circuit, the method comprising,
  (a) preparing a first synthetic minimal cell (SMC) comprising at least two genes that are components of the first multi-gene genetic circuit, wherein an activity of a first of the at least two genes in the first SMC modulates an activity of at least one of: (1) one or more additional genes in the first SMC that are components of the first multi-gene genetic circuit and (2) one or more genes in a second SMC, wherein the one or more genes in the second SMC are independently selected and optionally are components of a second multi-gene genetic circuit;
  (b) contacting the prepared first SMC with a candidate compound;
  (c) identifying a change in an activity in the first multi-gene genetic circuits in the first SMC contacted with the candidate compound; and
  (d) comparing the identified activity change to the activity in a control SMC not contacted with the candidate compound; wherein a change in the activity in the contacted first SMC compared to the control SMC indicates an effect of the candidate compound on the activity of the first multi-gene genetic circuit.

22. A method of assessing a modulating effect of an activity of a first synthetic minimal cell (SMC on an activity of a third SMC, the method comprising,
  (a) preparing the first SMC comprising at least two genes that are components of a first multi-gene genetic circuit, wherein an activity of a first of the at least two genes in the first SMC modulates an activity of at least one of: (1) one or more additional genes in the first SMC that are components of the first multi-gene genetic circuit and (2) one or more genes in a second SMC, wherein the one or more genes in the second SMC are independently selected and optionally are components of a second multi-gene genetic circuit;
  (b) preparing a third SMC comprising one or more independently selected genes that are components of at least one independently selected multi-gene genetic circuit;
  (c) activating in the first SMC one of the at least two genes in the first multi-gene genetic circuit, wherein the first SMC is in the presence of the third SMC;
  (d) determining the presence or absence of a modulation effect on an activity of at least one of the one or more independently selected genes in the third SMC; and
  (e) assessing the modulation effect of the activity of the first SMC on the activity of the multi-gene genetic circuit of the third SMC.

23. A composition comprising a first synthetic minimal cell (SMC) comprising a first gene that is a component of a multi-gene genetic circuit and a second SMC comprising an independently selected second gene that is a component of the multi-gene genetic circuit.

* * * * *